United States Patent [19]

Iwaki et al.

[11] Patent Number: 5,143,643

[45] Date of Patent: Sep. 1, 1992

[54] OPTICALLY ACTIVE MESOMORPHIC COMPOUND

[75] Inventors: Takashi Iwaki; Kenji Shinjo; Akio Yoshida; Masataka Yamashita, all of Kanagawa; Kazuharu Katagiri, Tokyo; Chieko Hioki; Takeshi Togano, both of Kanagawa; Yoko Yamada; Masahiro Terada, both of Kanagawa, all of Japan

[73] Assignee: Canon Kabushiki Kaisha, Tokyo, Japan

[21] Appl. No.: 373,640

[22] Filed: Jul. 3, 1989

Related U.S. Application Data

[62] Division of Ser. No. 82,650, Aug. 7, 1987, abandoned.

[30] Foreign Application Priority Data

| Aug. 8, 1986 | [JP] | Japan | 61-186578 |
| Aug. 21, 1986 | [JP] | Japan | 61-193974 |
| Sep. 30, 1986 | [JP] | Japan | 61-230049 |
| Jul. 27, 1987 | [JP] | Japan | 62-188301 |
| Jul. 29, 1987 | [JP] | Japan | 62-187498 |
| Jul. 29, 1987 | [JP] | Japan | 62-187499 |
| Jul. 29, 1987 | [JP] | Japan | 62-187500 |

[51] Int. Cl.$^5$ ............ C09K 19/34; C09K 19/52; C09K 19/30; C09K 19/12
[52] U.S. Cl. ............ 252/299.61; 252/299.01; 252/299.63; 252/299.64; 252/299.65; 252/299.66; 252/299.67; 544/298; 544/335
[58] Field of Search ......... 252/299.01, 299.6, 299.61, 252/299.63, 299.64, 299.65, 299.66, 299.67, 299.68; 350/350.5; 544/298, 335; 359/103, 104

[56] References Cited

U.S. PATENT DOCUMENTS

| 4,556,727 | 12/1985 | Walba | 252/299.01 |
| 4,576,732 | 3/1986 | Tsugai et al. | 252/299.65 |
| 4,613,209 | 9/1986 | Goodby et al. | 252/350.5 |
| 4,725,688 | 2/1988 | Taguchi et al. | 252/299.01 |
| 4,744,918 | 5/1988 | Hepple et al. | 252/299.61 |
| 4,775,223 | 10/1988 | Yoshinaga et al. | 252/299.01 |
| 4,812,259 | 3/1989 | Yoshiraga et al. | 252/299.65 |
| 4,820,839 | 4/1989 | Krause et al. | 252/299.61 |
| 4,834,904 | 5/1989 | Krause et al. | 252/299.61 |
| 4,882,085 | 11/1989 | Yoshinaga | 252/299.61 |

FOREIGN PATENT DOCUMENTS

| 0034268 | 8/1981 | European Pat. Off. . |
| 0175591 | 3/1986 | European Pat. Off. . |
| 255219 | 2/1988 | European Pat. Off. ....... 252/299.61 |
| 3515373 | 11/1986 | Fed. Rep. of Germany ............ 252/299.61 |
| 88/41445 | 2/1988 | Japan . |
| 88/51377 | 3/1988 | Japan . |
| 88/60951 | 3/1988 | Japan . |
| 2181429 | 4/1987 | United Kingdom ........... 252/299.65 |
| 87/05012 | 8/1987 | World Int. Prop. O. . |

OTHER PUBLICATIONS

Chem. Abs., vol. 62, No. 2 (1965) 1159c-e.
J. Org. Chem., vol. 48, No. 17 (1983) 2789:92.

Primary Examiner—Robert L. Stoll
Assistant Examiner—Shean C. Wu
Attorney, Agent, or Firm—Fitzpatrick, Cella, Harper & Scinto

[57] ABSTRACT

An optically active mesomorphic compound represented by the formula (III) is obtained through an optically active compound represented by the formula (I) and then through a compound represented by the formula (II), respectively, shown below.

-continued

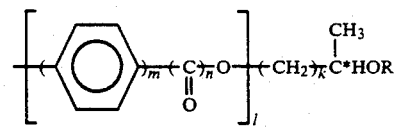

In the above formulas, R represents a linear, branched or cyclic saturated or unsaturated hydrocarbon group having 1-18 carbon atoms each capable of having a substituent, C* represents an asymmetric carbon atom, k is an integer of from 2 to 5, A is a releasable active group such as hydroxyl, l is 0 or 1, and when l is 1, m is 0, 1 or 2 and n is 0 or 1; $R^1$ represents an alkyl or alkoxy group having 1-18 carbon atoms;

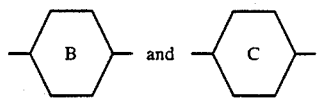

respectively denote

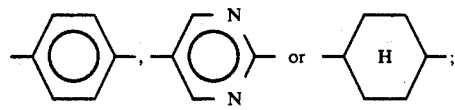

p, q and r are respectively 0 or 1 satisfying the relation of $p+q+r \geq 1$.

167 Claims, 4 Drawing Sheets

OPTICALLY ACTIVE MESOMORPHIC COMPOUND

This application is a division of application Ser. No. 082,650, filed Aug. 7, 1987 now abandoned.

FIELD OF THE INVENTION AND RELATED ART

The present invention relates to a mesomorphic compound intermediate susceptible of ready molecular structure modification and showing an optical activity, a mesomorphic compound derived therefrom, a liquid crystal composition containing the same and also a liquid crystal device using the liquid crystal composition.

There has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127-128. In this type of liquid crystal devices, the number of picture elements have been restricted, because there is a problem that a crosstalk phenomenon occurs when a device of a matrix electrode structure with a high density of picture elements is driven according to a multiplexing driving scheme. Further, their uses for display have been limited because of slow electric field response and poor visual angle characteristics.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4367924).

As the bistable liquid crystal, a ferroelectric crystal showing a chiral smectic C phase (SmC*) or H phase (SmH*) is generally used.

Such a ferroelectric liquid crystal has very rapid response speed on account of having spontaneous polarization, can also exhibit memorizable bistable state and further have excellent vision angle characteristic, and therefore it is suitable for a display of large capacity and large picture area.

The mesomorphic compound which is used for ferroelectric liquid crystal has an asymmetric carbon and therefore it can be used for optical devices as shown below other than the utilization for a ferroelectric liquid crystal in which its chiral smectic phase is used:

1) the device in which cholesteric-nematic phase transition effect is utilized in mesomorphic state (J. J. Wysoki, A. Adams, and W. Haas; Phys. Rev. Lett., 20, 1024 (1968));

2) the device in which White-Taylor type guest-host effect is utilized (D. L. White and G. N. Taylor; J. Appl. Phys., 45 4718 (1974));

3) the device in which a compound having cholesteric phase in mesomorphic state is fixed in matrix and utilized as notch filter or band path filter by utilizing its selective scattering characteristics (F. J. Kahn, Appl. Phys. Lett., 18, 231 (1971)), or the device in which the compound is utilized as a circular polarizing light beam splitter by utilizing the circular polarizing light characteristic (S. D. Jacobs, SPIE, 37, 98 (1981)); etc.

Although detailed descriptions of the individual systems are omitted here, all of them are important as display devices or modulating devices.

In the prior art, as the optically active intermediate for synthesis of functional materials necessary for optical devices characterized by having optical activity, 2-methylbutanol, sec-octyl alcohol, sec-butyl alcohol, p-(2-methylbutyl)benzoic acid chloride, sec-phenetyl alcohol, amino acid derivatives, camphor derivatives, and cholesterol derivatives have been known.

However, these compounds have the following drawbacks. Optically active chain hydrocarbon derivatives can be modified in structure with difficulty, and they are generally very expensive except for a particular class thereof. Amino acid derivatives are relatively inexpensive and also modified in structure with ease, but the hydrogen atom of amine has strong chemical activity to form hydrogen bond or cause chemical reaction readily, whereby the characteristics of the functional material are liable to be restricted. Camphor derivatives and cholesterol derivatives can be modified in structure with difficulty and also affect badly the characteristics of functional materials due to theri steric hindrances.

The drawbacks as mentioned above have been great restrictions in developments of various materials.

Further, U.S. patent application Ser. Nos. 776963, 893821 and 922308 disclose some lactic acid derivatives useful as mesomorphic compounds.

SUMMARY OF THE INVENTION

In view of the state of the art as described above, a principal object of the present invention is to provide an optically active compound which is not only useful as a suitable optically active intermediate but also useful for control of mesomorphic state, and also a liquid crystal composition containing the same.

More specifically, an object of the present invention is to provide a compound which can be combined with an intermediate for a functional material having appropriate intermolecular force and shape for forming liquid crystal, LB (Langmuir-Blodgett) film, bimolecular films, etc., without impairing an optical activity, and therefore susceptible of arbitrary molecular designing. Another object of the present invention is to provide a compound which undergoes great spontaneous polarization when used as a ferroelectric liquid crystal due to the presence of an oxygen atom adjacent to an asymmetric carbon atom.

Still another object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold, Z. Phys. Chem., 226, 146 (1964), and a liquid crystal composition containing at least one of such mesomorphic compounds.

A further object of the present invention is to provide a compound capable of easily controlling the hydrophobic group and being stably formed into a film when applied to the LB (Langmuir-Blodgett) film process for preparing built-up monomolecular films.

More specifically, the present invention provides an optically active compound represented by the following formula (I):

wherein R represents a linear, branched or cyclic saturated or unsaturated hydrocarbon group having 1–18 carbon atoms each capable of having a substituent, C* represents an asymmetric carbon atom, and k is an integer of from 2 to 5.

The present invention further provides an optically active compound represented by the following formula (II):

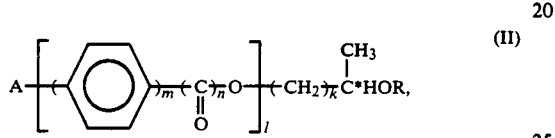

wherein R represents a linear, branched or cyclic saturated or unsaturated hydrocarbon group having 1–18 carbon atoms each capable of having a substituent, C* represents an asymmetric carbon atom, k is an intefer of from 2 to 5, l is 0 or 1, and when l is 1, m is 0, 1 or 2 and n is 0 or 1; and A is a hydroxyl, alkoxyl, acyloxy, tosyloxy or halogen radical.

The present invention further provides an optically active mesomorphic compound represented by the following formula (III):

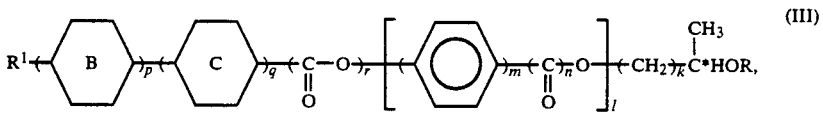

wherein R represents a linear, branched or cyclic saturated or unsaturated hydrocarbon group having 1–18 carbon atoms each capable of having a substituent, C* represents an asymmetric carbon atom, k is an integer of from 2 to 5, l is 0 or 1, and when l is 1, m is 0, 1 or 2 and n is 0 or 1; $R^1$ represents an alkyl or alkoxy group having 1–18 carbon atoms;

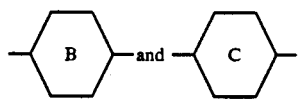

respectively denote

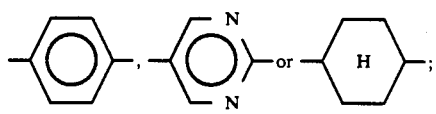

p, q and r are respectively 0 or 1 satisfying the relation of $q+1+r \geq 1$.

The present invention further provides a mesomorphic compound represented by the following formula (IV):

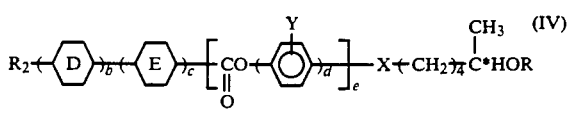

wherein R represents a linear, branched or cyclic saturated or unsaturated hydrocarbon group having 1–18 carbon atoms each capable of having a substituent; $R^2$ is an alkoxy, acyl, acyloxy, alkoxycarbonyl or alkoxycarbonyloxy group having 1–18 carbon atoms each capable of having a substituent; C* represents an asymmetric carbon atom;

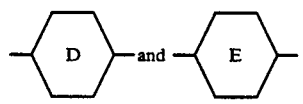

are respectively a 1,4-phenylene or pyrimidine-2,5-di-yl group each capable of having a substituent; b, c and d are respectively 0, 1 or 2; e is 0 or 1; X represents a single bond,

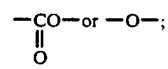

and Y represents a hydrogen atom, halogen atom, alkyl, alkoxy or cyano group.

In the above formulas (I)–(IV), the substituent for the group R may for example be a halogen atom or an alkoxy group. Further, in the formula (IV), the substituent for the group $R^2$ may for example be an alkyl group, a halogen atom or an alkoxy group; and the substituent for the groups —C— and —D— may for example be a halogen atom, alkyl group, alkoxy group or cyano group.

The present invention further provides a liquid crystal composition containing at least one compound represented by the formula (II), (III) or (IV) and also a liquid crystal device using the liquid crystal composition.

DETAILED DESCRIPTION OF THE INVENTION

Figure 1:
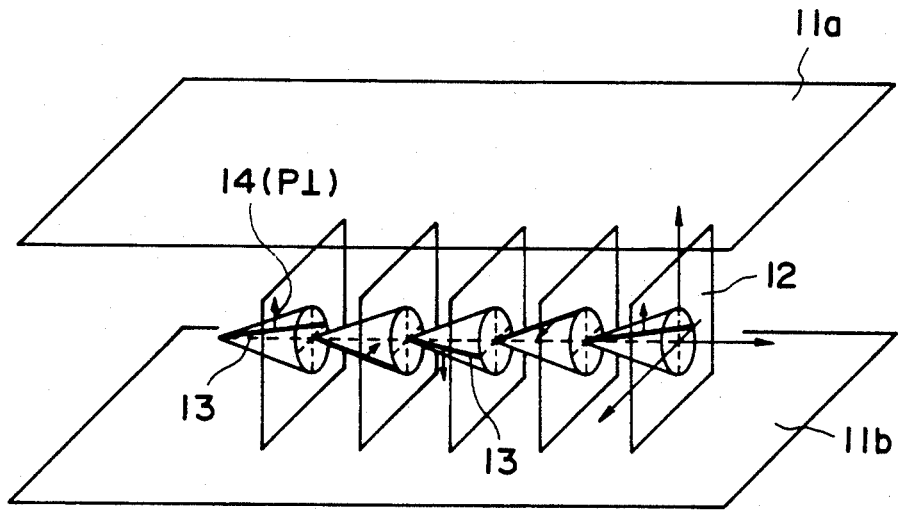
FIGS. 1 and 2 are perspective views representing schematically a liquid crystal device for multiplexing drive to be used in the present invention.

In the formula (I) representing the above optically active compound, R is a linear, branched or cyclic saturated or unsaturated hydrocarbon group having 1 to 18 carbon atoms. A group having 19 or more carbon atoms is not preferable because the viscosity or molar volume of the functional material finally made will be increased. Also, preferable number of carbon atoms in R is 4 to 16. Typical examples of R include linear alkyl group, branched alkyl group, cycloalkyl group, linear alkenyl group, branched alkenyl group, cycloalkenyl group, linear alkadienyl group, branched alkadienyl group, cycloalkadienyl group, linear alkatrienyl group, branched alkatrienyl group, linear alkynyl group, branched alkynyl group, and aralkyl group. For providing mesomorphic compounds as described below, alkyl groups are particularly preferred. C* represents an asymmetric carbon atom.

Further, the optically active compound represented by the formula (II) wherein A is OH of the present invention may be reacted with a various reagent to provide a mesomorphic compound or other functional compound.

An example class of the mesomorphic compound thus obtained comprises those represented by the above formula (III) which corresponds to a case where A in the formula (II) is

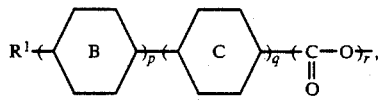

wherein $R^1$ represents an alkyl or alkoxy group having 1-18 carbon atoms;

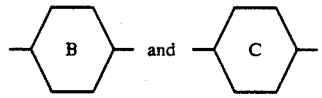

respectively denote

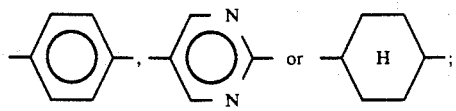

p, q and r are respectively 0 or 1 satisfying the relation of $p+q+r \geq 1$. In this case, the number of carbon atoms in the group R may preferably be 4-18, particularly 6-16.

In order to obtain other functional materials than the above, it is effective to react the compound according to the formula (II) where A is OH without impairing the optical activity with a functional material intermediate having an appropriate intermolecular force and shape and susceptible of molecular control. Examples of such intermediates of functional material effective for combination with the optically active compound according to the present invention include azo derivatives, azoxy derivatives, ring-assembly hydrocarbon derivatives, condensed polycyclic hydrocarbon derivatives, heterocyclic derivatives, condensed heterocyclic derivatives, and ring-assembly heterocyclic derivatives. More specifically, there are included azobenzene derivatives, azoxybenzene derivatives, biphenyl derivatives, terphenyl derivatives, phenylcyclohexane derivatives, benzoic acid derivatives pyrimidine derivatives, pyrazine derivatives, pyridine derivatives, stilbene derivatives, tolan derivatives, chalcone derivatives, bicyclohexane derivatives, and cinnamic acid derivatives.

Next, the process for producing the optically active alcohol represented by the formula (I) will be exemplified. The optically active alcohols may be prepared from or through lactic acid ester, 2-hydroxypropionic acid ester, 3-hydroxybutyric acid ester, 2-alkoxypropnaol, 3-alkoxybutanol or 4-alkoxypentanol according to the following reaction schemes. The formulas [Ia], [Ib], [Ic and [Id] in the following schemes correspond to the formula (I) above where k is 2, 3, 4 and 5, respectively.

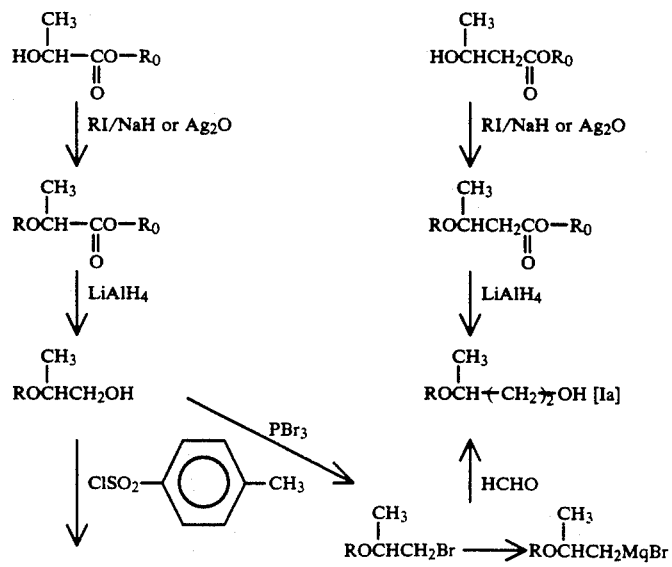

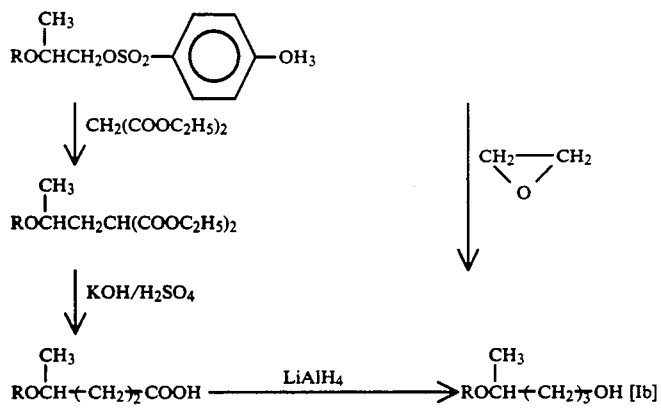
In the above schemes, $R_0$ represents a lower alkyl group, and R is the same as defined before.
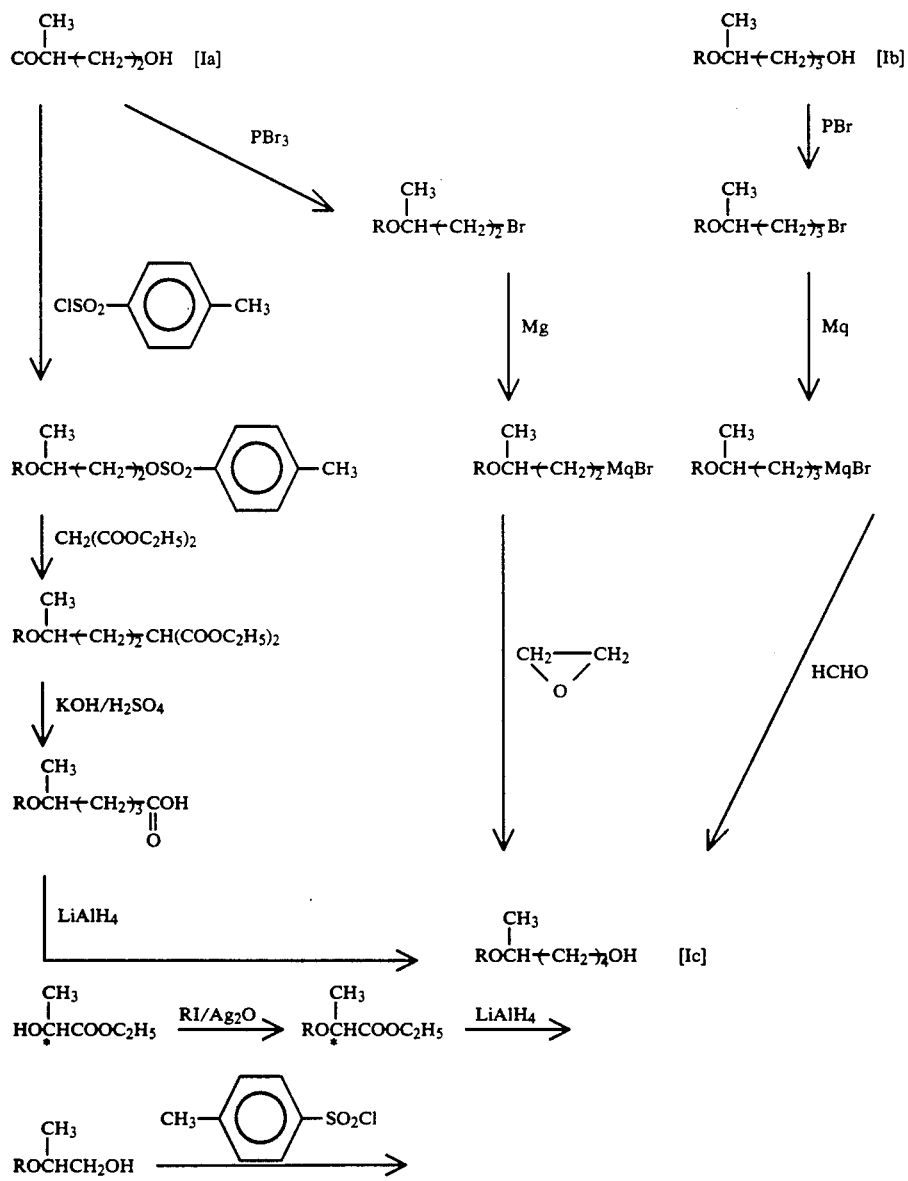

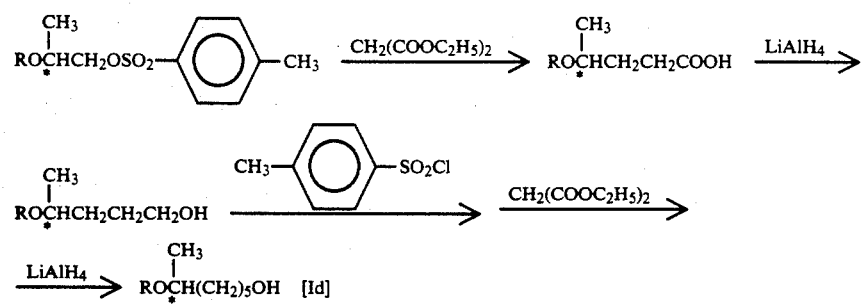

The RI in the above reaction scheme may be selected from a wide scope of iodides. Examples thereof include linear saturated hydrocarbon iodides such as iodobutane, iodopentane, iodohexane, iodoheptane, iodooctane, iodononane, iododecane, iodoundecane, iodododecane, iodotridecane, iodotetradecane, iodopentadecane, iodohexadecane, iodoheptadecane, iodooctadecane, iodononadecane, and iodocicosane; branched saturated hydrocarbon iodides such as 2-iodobutane, 2-iodo-2-methylpropane and 1-iodo-3-methylbutane; cyclic unsaturated hydrocarbon iodides such as iodobenzyl, iodophenacyl and 3-iodo-1-cyclohexane; and cyclic saturated hydrocarbon iodides such as iodocyclopentane, iodocyclohexane, i-iodo-3-methylcyclohexane, iodocycloheptane and iodocyclooctane.

An appropriate RI may be selected from the iodides as described above to obtain an optically active compound represented by the formula (I) with a different group R.

The optically active compounds represented by the formulas (II) and (III) according to the present invention may be obtained from the compound of the formula (I) thus prepared according to the following reaction schemes.

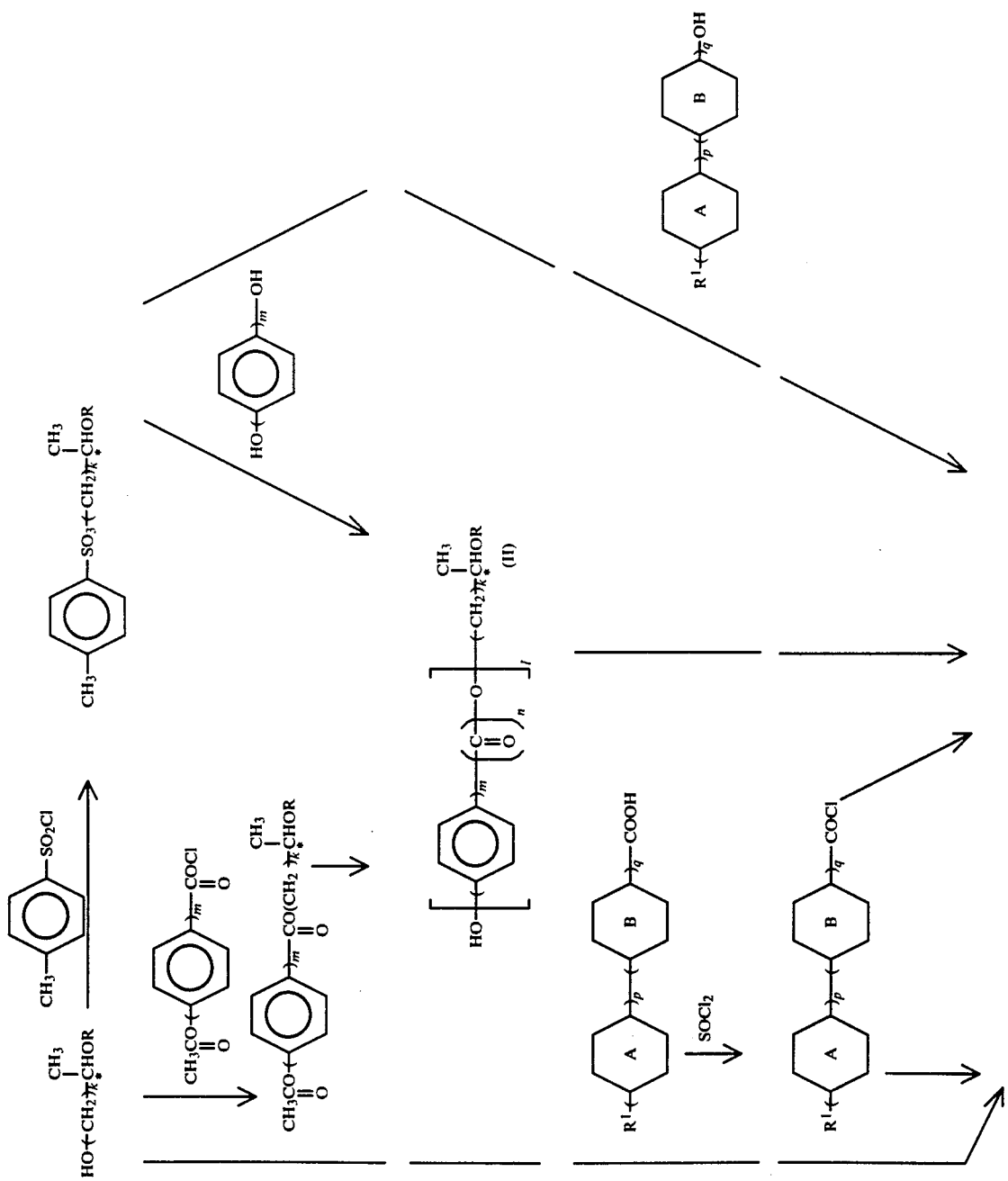

-continued $$R^1\underset{p}{\overline{\left(A\right)}}\underset{q}{\overline{\left(B\right)}}\left[\underset{}{CO}\atop{O}\right]_r\left[\underset{}{\bigcirc}\right]_m\left(\underset{O}{C=O}\right)_n\left[O-(CH_2)_k\overset{CH_3}{\underset{*}{C}}HOR\right]_l \quad (III)$$

In the above schemes, R, R[1], l, m, n, p, q, r and k are the same as defined before Tables 1 and 2 given below show examples of the mesomorphic compounds thus obtained In the Tables 1 and 2 are the description appearing hereinafter, the abbreviations used for describing phase transition characteristics represent the following:

Cryst.: crystalline phase,
Ch.: cholesteric phase,
Iso.: isotropic phase,
SmC*: chiral smectic phase,
SmA: smectic A phase,
SmB: smectic B phase,
SmC: smectic C phase,
N: nematic phase,
Sm1, Sm2, Sm3: smectic phase (unidentified).

TABLE 1

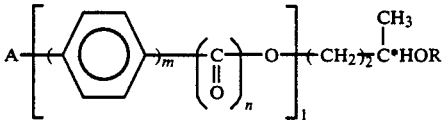
(IIIa)

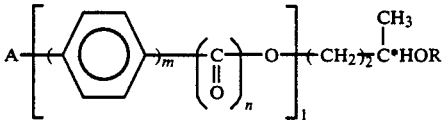

| Example | A = | l | m | n | R | Phase transition temperature (°C.) |
|---|---|---|---|---|---|---|
| 14 | 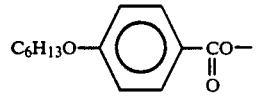 | 1 | 1 | 0 | $C_5H_{11}$ | 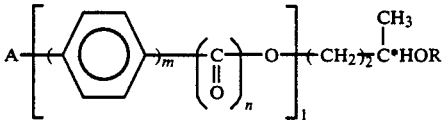 |
| 15 | 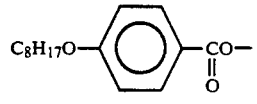 | 1 | 1 | 0 | $C_5H_{11}$ | 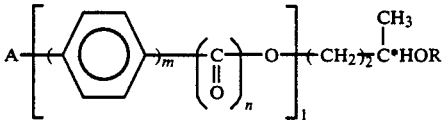 |
| 16 | 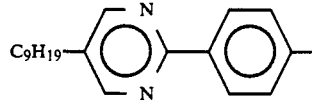 | 1 | 0 | 0 | $C_5H_{11}$ | 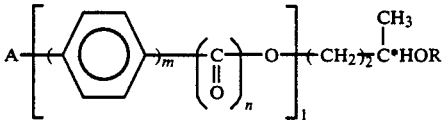 |
| 17 | 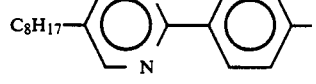 | 1 | 0 | 0 | $C_{12}H_{25}$ | 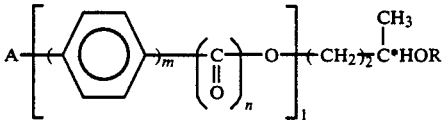 |
| 18 | 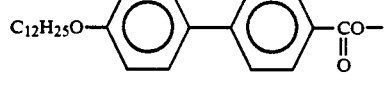 | | | 0 | $C_{12}H_{25}$ | 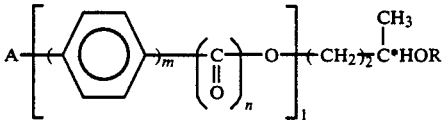 |
| 19 | 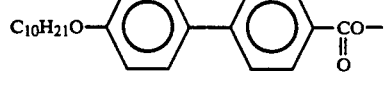 | 1 | 1 | 1 | $C_5H_{11}$ | 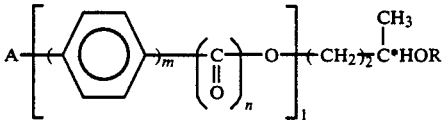 |
| 20 | 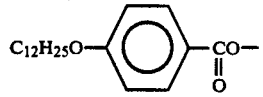 | 1 | 1 | 1 | $C_5H_{11}$ | 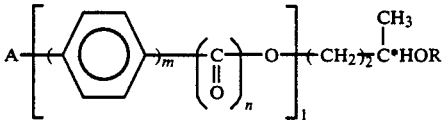 |
| — | 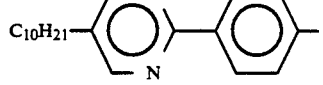 | 1 | 0 | 0 | $CH_3$ | (racemic mixture) |

TABLE 1-continued (IIIa)

$$A{-}{(\bigcirc)}_m{-}{(\underset{O}{\overset{\|}{C}})}_n{-}O{-}(CH_2)_2{-}\overset{CH_3}{\underset{}{C^*HOR}}]_l$$

| Example | $A = R^1{-}(B){-}_p(C){-}_q(\underset{O}{\overset{\|}{C}}{-}O)_r$ | l | m | n | R | Phase transition temperature (°C.) |
|---|---|---|---|---|---|---|
| — | $C_{10}H_{21}O{-}\bigcirc{-}\bigcirc{-}\underset{O}{\overset{\|}{C}}O{-}$ | 1 | 1 | 0 | $C_3H_7$ | Cryst. $\xrightleftharpoons[39]{73}$ SmC* $\xrightleftharpoons[134]{134}$<br>Sm3 $\xleftarrow{72}$<br>SmA $\xrightleftharpoons[156]{158}$ Iso. |

TABLE 2

[IIIb]

$$A{-}{(\bigcirc)}_m{-}{(\underset{O}{\overset{\|}{C}})}_n{-}O{-}(CH_2)_3{-}\overset{CH_3}{\underset{}{C^*HOR}}]_l$$

| Example | $A = R^1{-}(B){-}_p(C){-}_q(\underset{O}{\overset{\|}{C}}{-}O)_r$ | R | l | m | n | Phase transition temperature (°C.) |
|---|---|---|---|---|---|---|
| 22 | $C_8H_{17}{-}\text{pyrimidine}{-}\bigcirc{-}$ | $C_8H_{17}$ | 1 | 0 | 0 | Cryst. $\xrightleftharpoons[6.2]{30.3}$ Iso. $\xrightarrow{12.6}$ SmA |
| 23 | $C_{10}H_{21}{-}\text{pyrimidine}{-}\bigcirc{-}$ | $C_3H_7$ | 1 | 0 | 0 | Cryst. $\xrightleftharpoons[-2.0]{27.0}$ Iso. $\xrightarrow{25.0}$ SmC* |
| 24 | $C_9H_{19}{-}\text{pyrimidine}{-}\bigcirc{-}$ | $C_5H_{11}$ | 1 | 0 | 0 | Cryst. $\xrightleftharpoons[-22.7]{23.3}$ Iso. $\xrightarrow{23.3}$ SmA $\xrightarrow{-11}$ Sm3 |
| 25 | $C_{10}H_{21}O{-}\bigcirc{-}\bigcirc{-}$ | $C_8H_{17}$ | 1 | 0 | 1 | Cryst. $\xrightleftharpoons[26.2]{42.8}$ Iso. $\xrightarrow{32.9}$ SmA |
| 26 | $C_8H_{17}O{-}\bigcirc{-}\underset{O}{\overset{\|}{C}}O{-}$ | $C_5H_{11}$ | 1 | 1 | 0 | Cryst. $\xrightleftharpoons[-7.9]{41.6}$ Iso. $\xrightarrow{41.0}$ SmA $\xrightarrow{4.8}$ Sm3 |
| 27 | $C_{12}H_{25}O{-}\bigcirc{-}\underset{O}{\overset{\|}{C}}O{-}$ | $C_5H_{11}$ | 1 | 1 | 0 | Cryst. $\xrightleftharpoons[-5.9]{19.1}$ Sm3 $\xrightleftharpoons[15.9]{23.1}$ SmC* $\xrightleftharpoons[35.0]{38.4}$ SmA $\xrightleftharpoons[39.7]{41.3}$ Iso. |

TABLE 2-continued

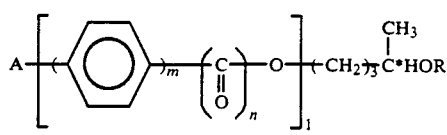
[IIIb]

| Example | A = R¹-(B)ₚ-(C)_q-(CO-O)ᵣ | R | l | m | n | Phase transition temperature (°C.) |
|---|---|---|---|---|---|---|
| 28 | C₁₀H₂₁O-⌬-⌬-CO-O- | C₅H₁₁ | 1 | 1 | 0 | Cryst. $\underset{25.8}{\overset{31.0}{\rightleftarrows}}$ Sm3 $\underset{78.5}{\overset{79.1}{\rightleftarrows}}$ SmC* $\underset{135.1}{\overset{135.5}{\rightleftarrows}}$ Ch. $\underset{147.2}{\overset{147.6}{\rightleftarrows}}$ Iso. |
| 29 | C₈H₁₇O-⌬-CO-O- | C₃H₇ | 1 | 1 | 1 | Cryst. $\underset{-9.5}{\overset{31.9}{\rightleftarrows}}$ SmA $\underset{36.5}{\overset{37.9}{\rightleftarrows}}$ Iso.; SmC* (14.5) |
| 30 | C₁₂H₂₅O-⌬-CO-O- | C₃H₇ | 1 | 1 | 1 | Cryst. $\underset{-1}{\overset{32.2}{\rightleftarrows}}$ SmC* $\underset{33.3}{\overset{33.8}{\rightleftarrows}}$ SmA $\underset{40.0}{\overset{41.0}{\rightleftarrows}}$ Iso. |
| 31 | C₈H₁₇O-⌬-⌬-CO-O- | C₃H₇ | 1 | 1 | 1 | Cryst. $\underset{49.2}{\overset{51.2}{\rightleftarrows}}$ Sm3 $\underset{78.6}{\overset{79.4}{\rightleftarrows}}$ SmC* $\underset{131.8}{\overset{132.4}{\rightleftarrows}}$ SmA $\underset{165.7}{\overset{167.1}{\rightleftarrows}}$ Iso. |
| — | C₆H₁₃-pyrimidinyl-⌬- | C₃H₇ | 1 | 0 | 0 | Cryst. $\underset{-8.0}{\overset{-1.2}{\rightleftarrows}}$ SmA $\underset{2.9}{\overset{4.2}{\rightleftarrows}}$ Ch. $\underset{7.1}{\overset{8.2}{\rightleftarrows}}$ Iso. |
| — | C₈H₁₇-pyrimidinyl-⌬- | C₅H₁₁ | 1 | 0 | 0 | Cryst. $\underset{1.32}{\overset{16.1}{\rightleftarrows}}$ SmA $\underset{21.6}{\overset{24.2}{\rightleftarrows}}$ Iso. |
| — | C₁₀H₂₁-pyrimidinyl-⌬- | C₅H₁₁ | 1 | 0 | 0 | Cryst. $\overset{31.5}{\rightarrow}$ Iso.; SmC* (27.0, 3.7) |
| 34 | C₁₂H₂₅-pyrimidinyl-⌬- | C₃H₇ | 1 | 0 | 0 | Cryst. $\overset{41.7}{\rightarrow}$ Iso.; SmC* (37.7, 22.9) |

In addition to those shown in Tables 1 and 2, the following compounds may be obtained in a similar manner as examples of the mesomorphic compounds represented by the formula (III).

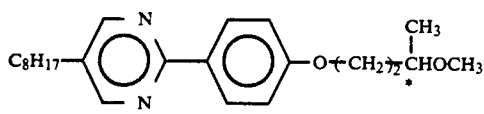
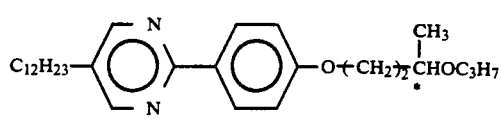

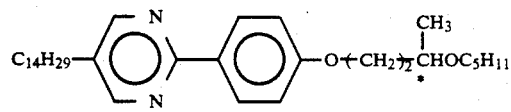
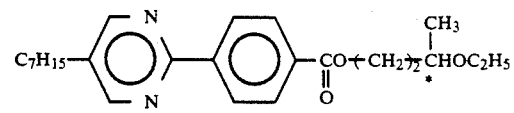
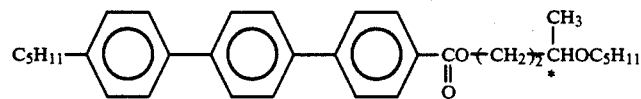
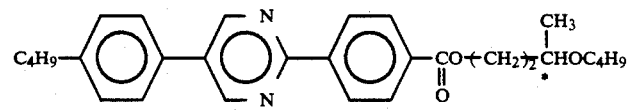
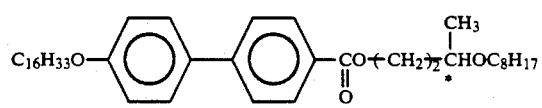
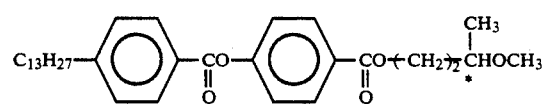
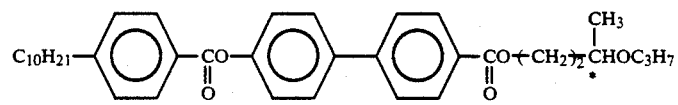
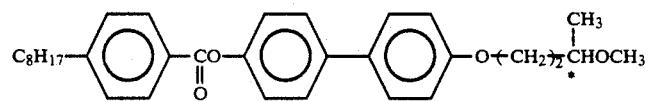
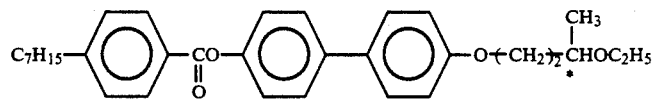
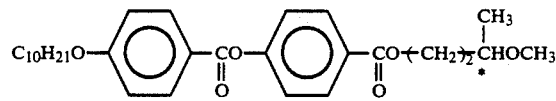
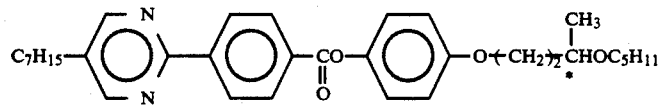
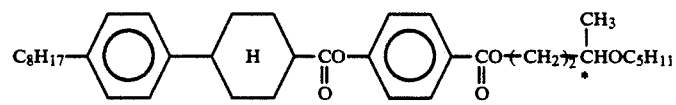
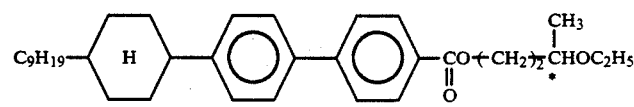

-continued
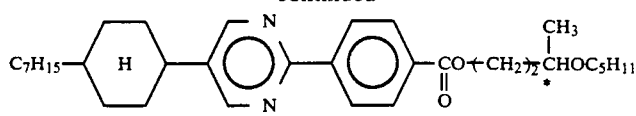
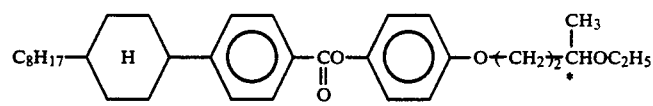
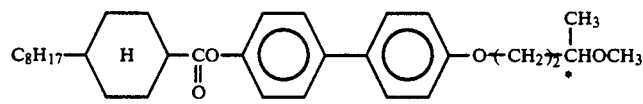
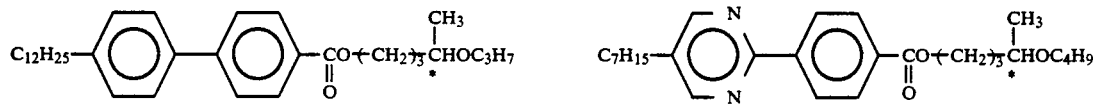
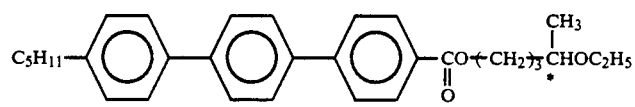
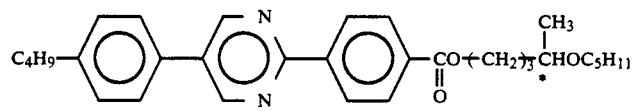
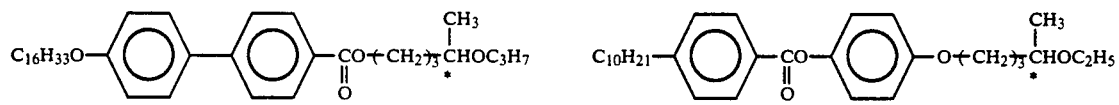
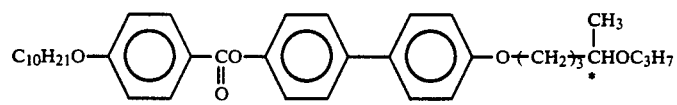
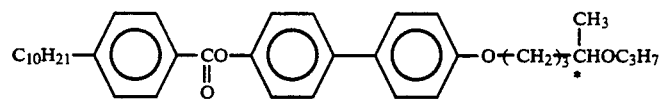
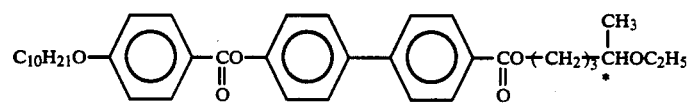
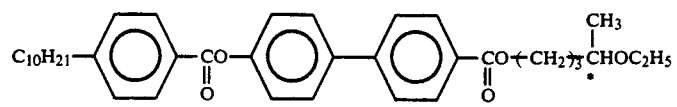

-continued
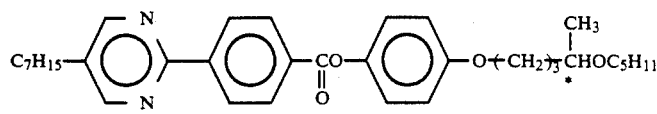
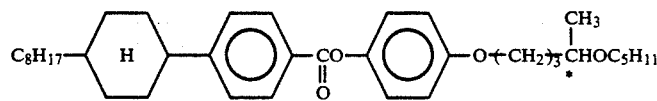
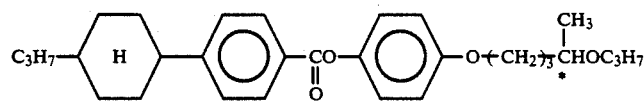
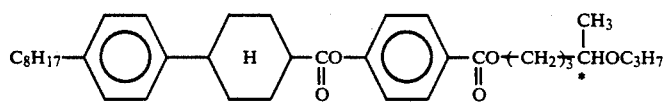
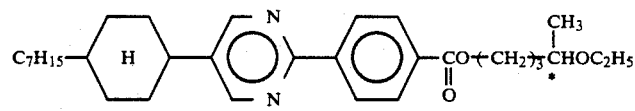
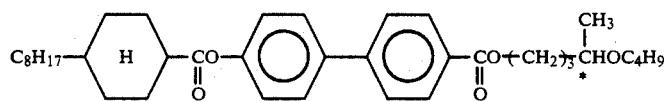
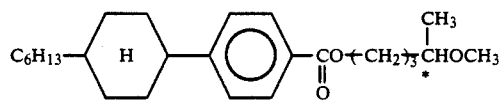
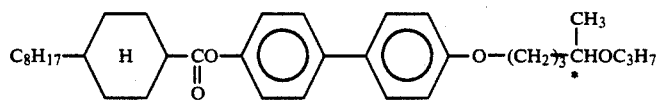
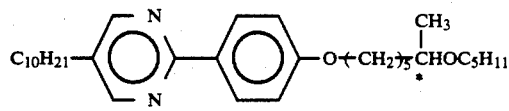
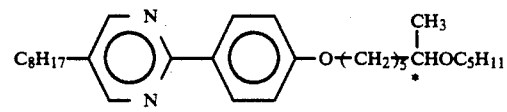
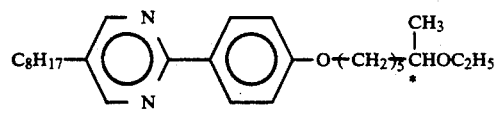
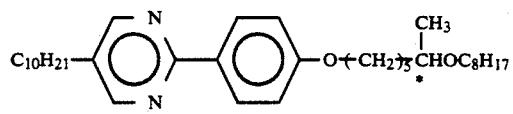
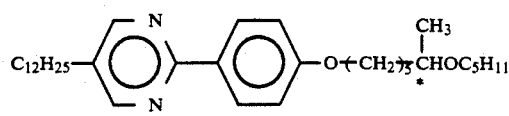
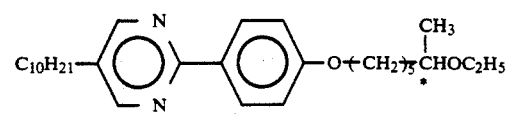

-continued
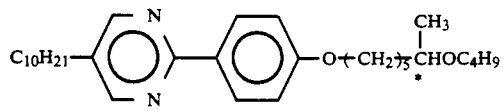 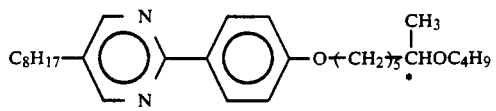
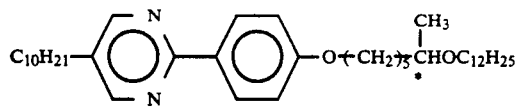 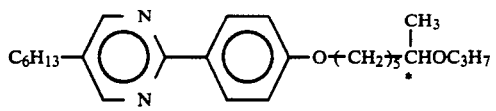
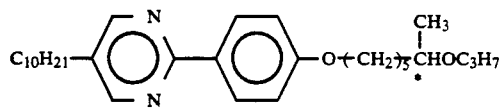 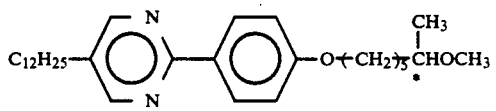
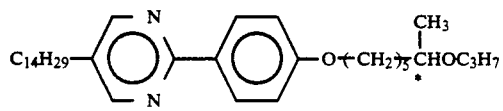 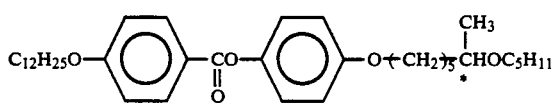
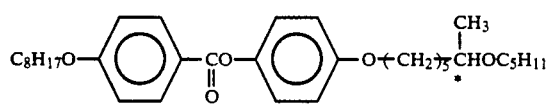 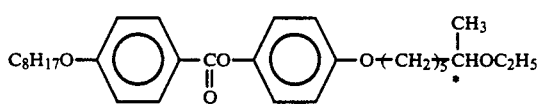
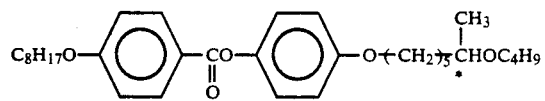 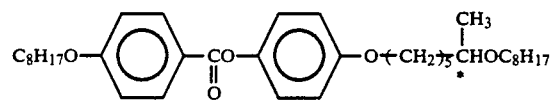
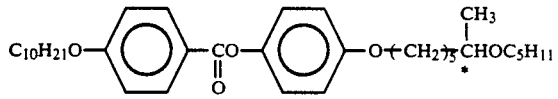 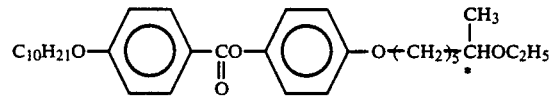
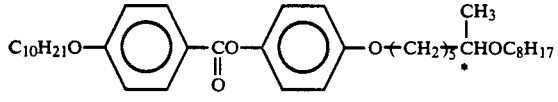 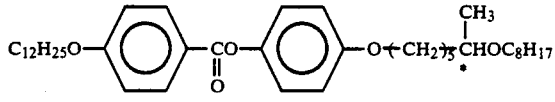
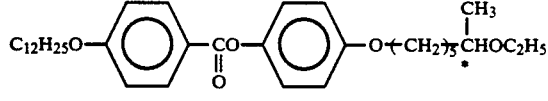 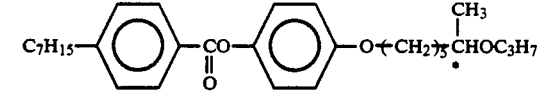
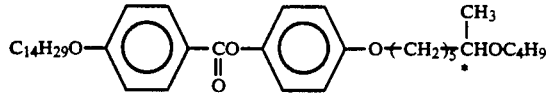 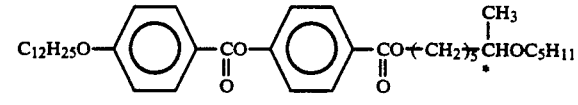
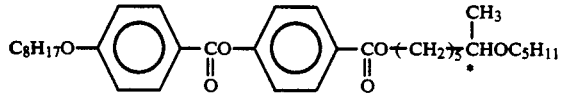 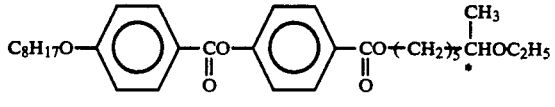
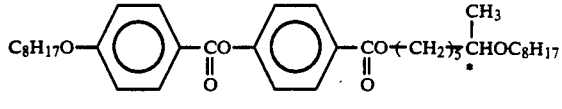 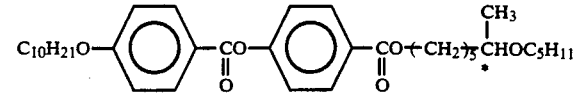

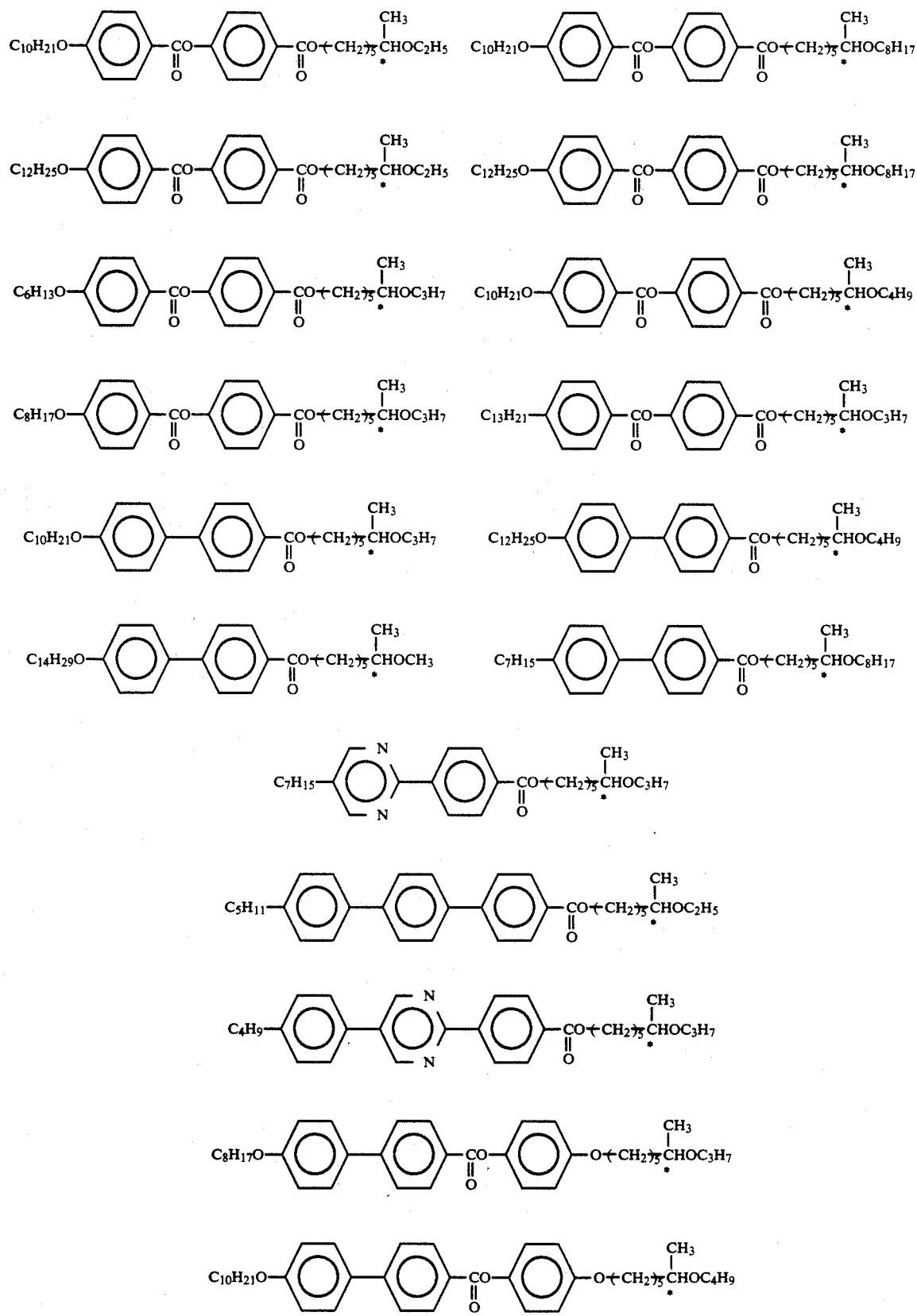

-continued
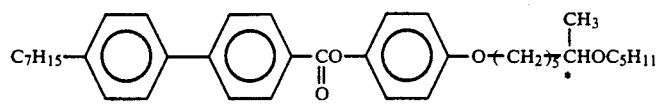
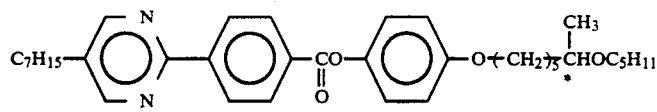
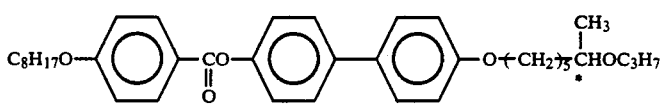
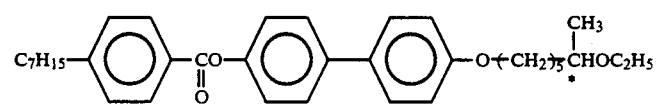
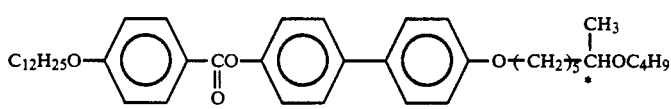
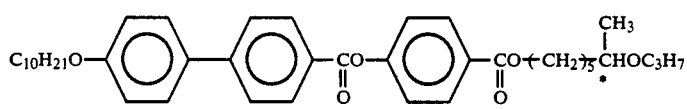
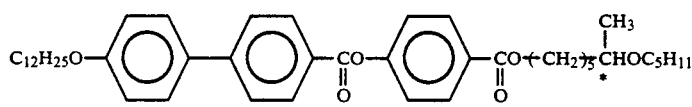
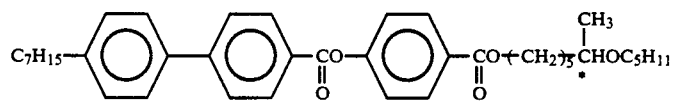
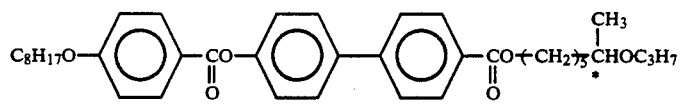
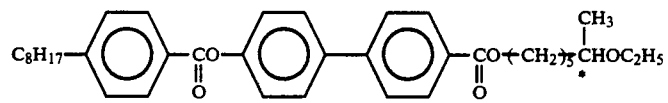
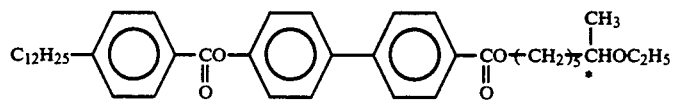
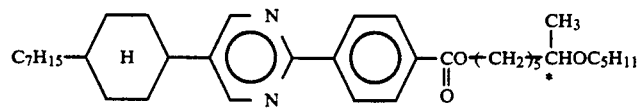

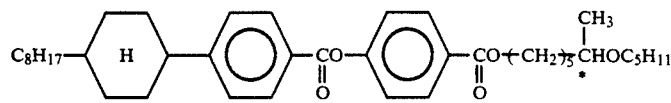
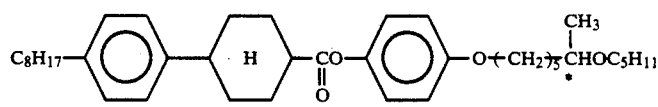
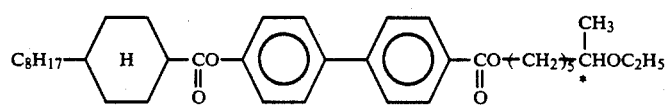
Examples of the mesomorphic compounds represented by the above formula (IV) are enumerated hereinbelow. Among them, some are also classified as examples of the mesomorphic compound represented by the formula (III) where k is 4.
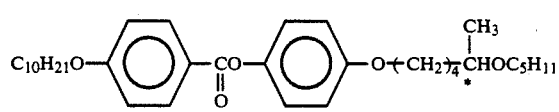 (Ex. 1)
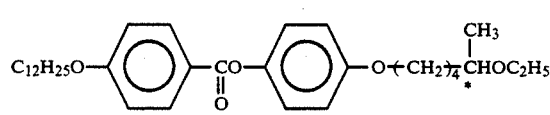 (Ex. 2)
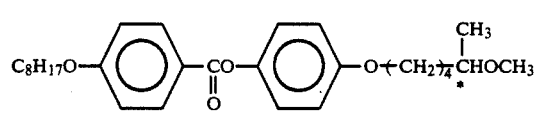 (Ex. 3)
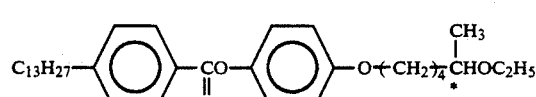 (Ex. 4)
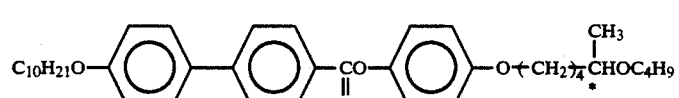 (Ex. 5)
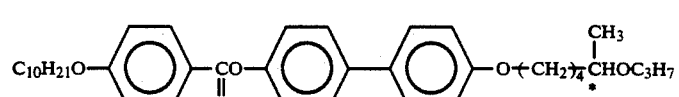 (Ex. 6)
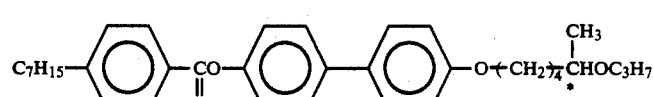 (Ex. 7)
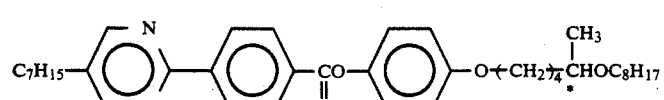 (Ex. 8)

-continued
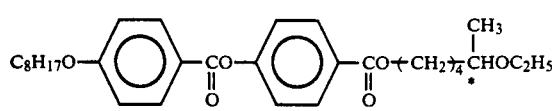 (Ex. 9)
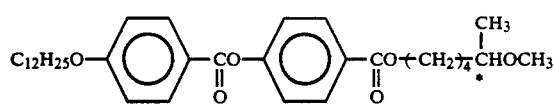 (Ex. 10)
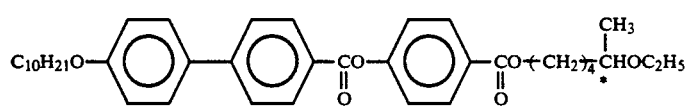 (Ex. 11)
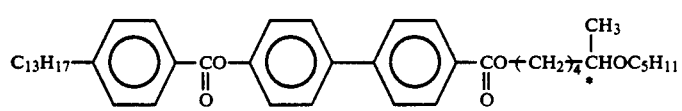 (Ex. 12)
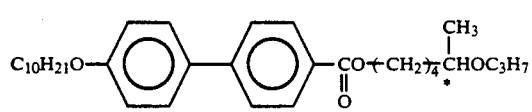 (Ex. 13)
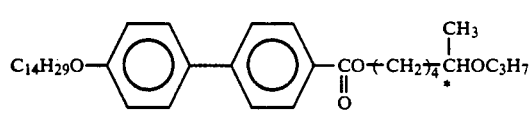 (Ex. 14)
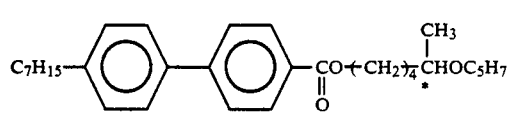 (Ex. 15)
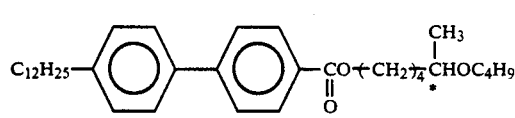 (Ex. 16)
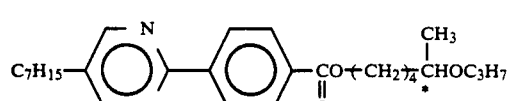 (Ex. 17)
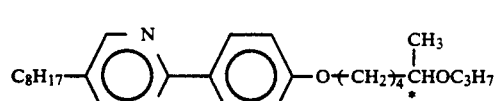 (Ex. 18)
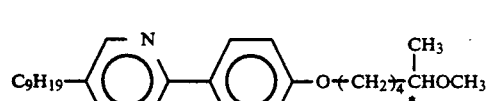 (Ex. 19)
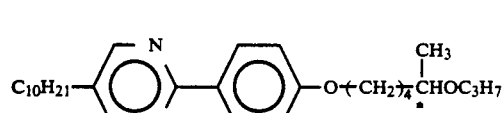 (Ex. 20)
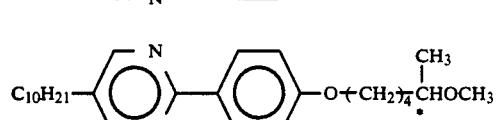 (Ex. 21)

-continued
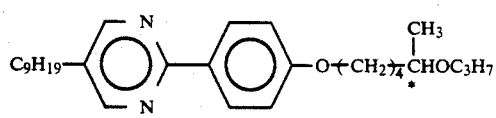 (Ex. 22)
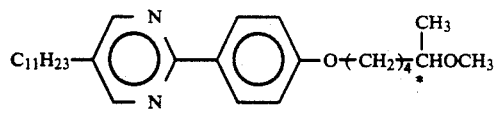 (Ex. 23)
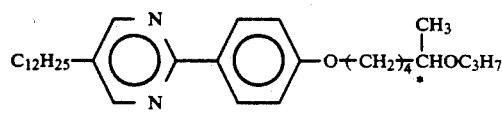 (Ex. 24)
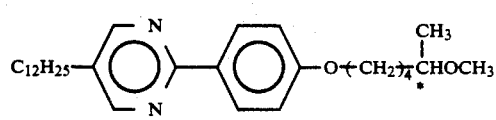 (Ex. 25)
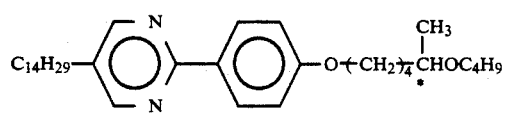 (Ex. 26)
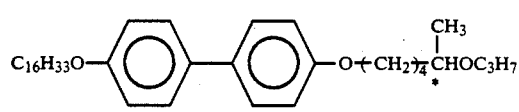 (Ex. 27)
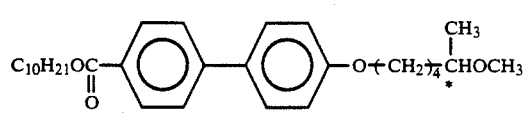 (Ex. 28)
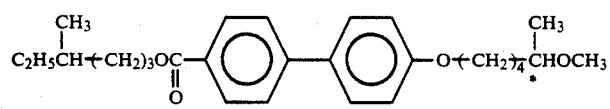 (Ex. 29)
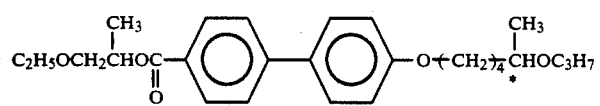 (Ex. 30)
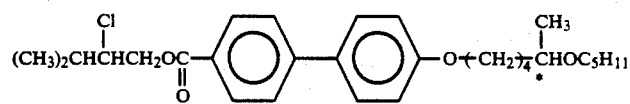 (Ex. 31)
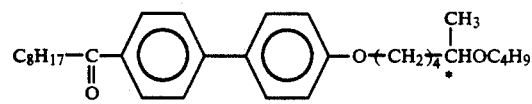 (Ex. 32)
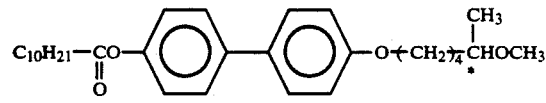 (Ex. 33)
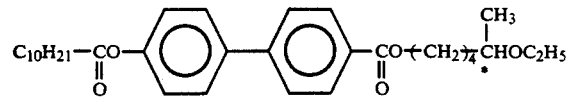 (Ex. 34)

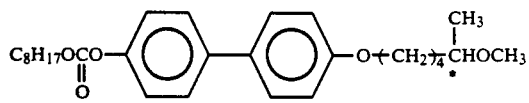 (Ex. 35)
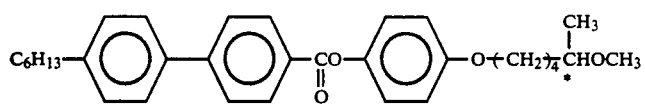 (Ex. 36)
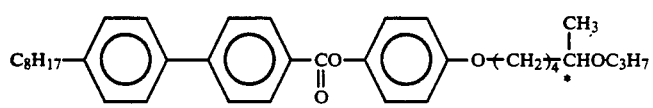 (Ex. 37)
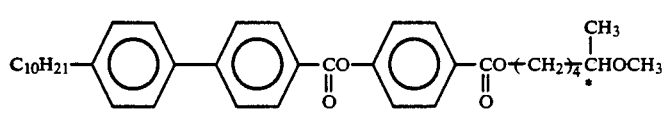 (Ex. 38)
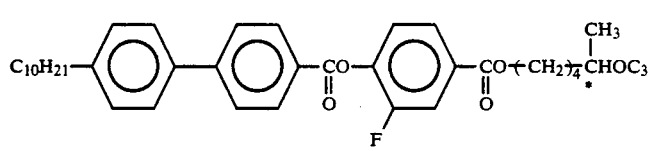 (Ex. 39)
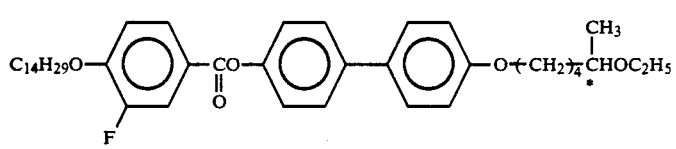 (Ex. 40)
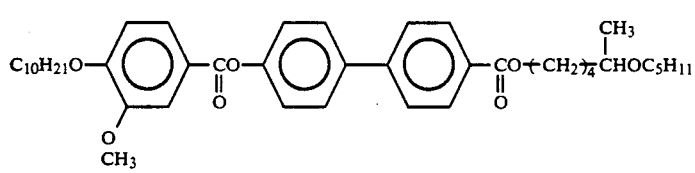 (Ex. 41)
The mesomorphic compounds represented by the formula (IV) may be prepared according to the following reaction schemes.
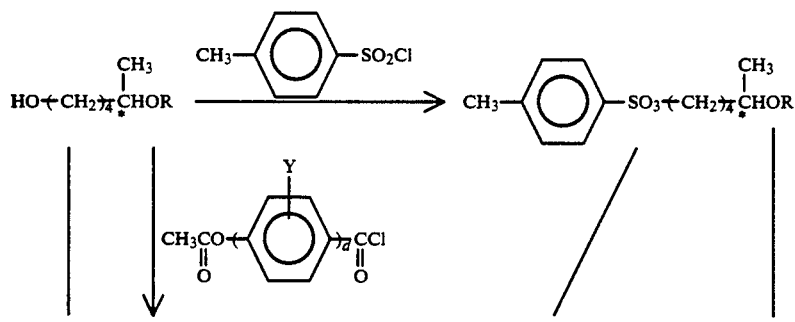

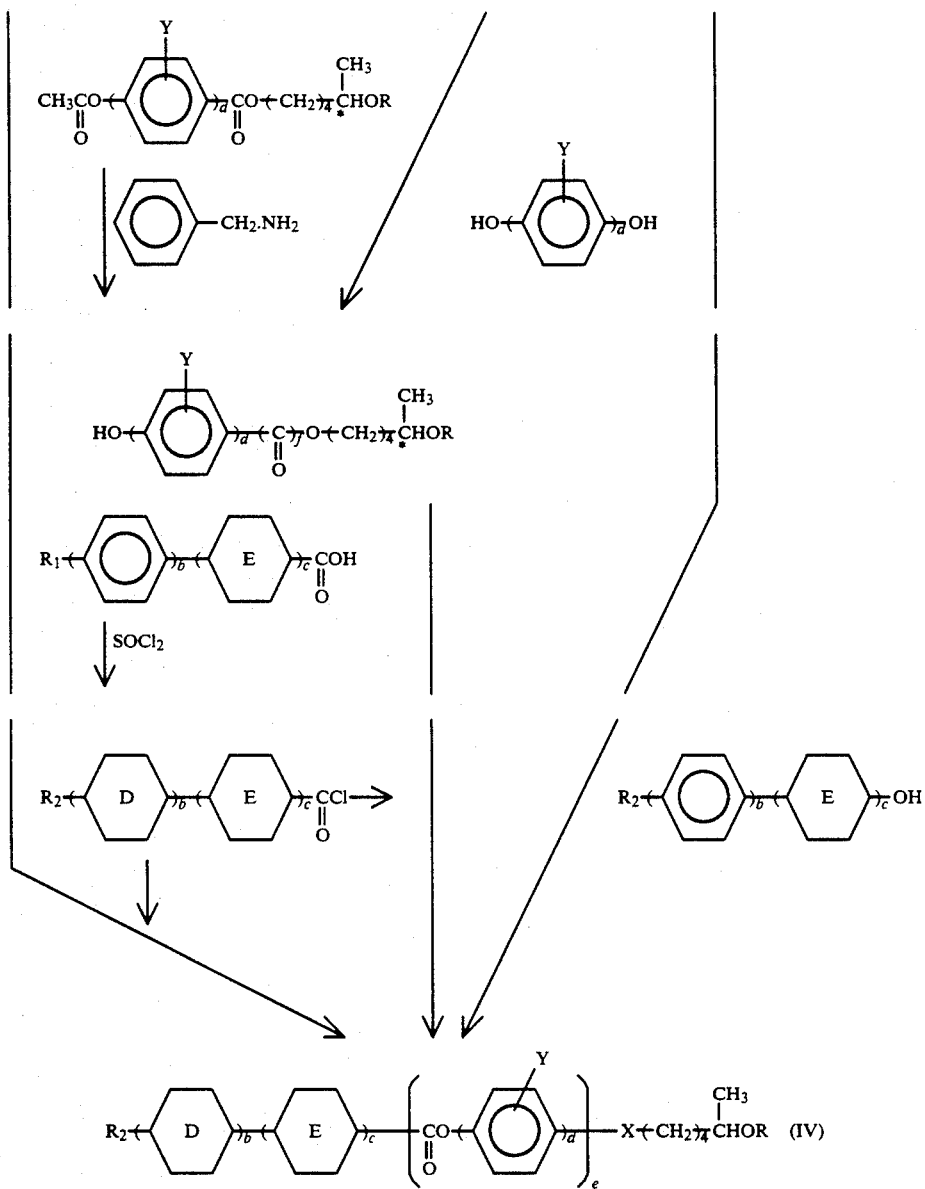

In the above reaction schemes, f is 0 or 1; and $R_2$, R, X, Y, b, c, d and e are the same as defined before.

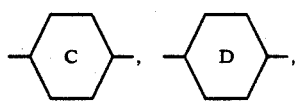

The liquid crystal composition of the present invention contains at least one of the optically active compounds or mesomorphic compounds represented by the formulas (II), (III) and (IV).

The liquid crystal composition of the present invention may preferably contain in addition to the compounds of the formulas (II)–(IV) a ferroelectric liquid crystal material represented by the following formulas (1)–(37) so that the resultant composition has an increased spontaneous polarization and a lower viscosity. In such a case, it is preferable to use an optically active compound of the formula (II) in a proportion of 0.1–30 wt. % of the resultant composition. Further, it is also preferred to use a mesomorphic compound of the formula (III) in a proportion of 0.1–99 wt. %, particularly 1–90 wt. %, of the resultant composition.

Further, it is preferred to mix 1–500 wt. parts of a mesomorphic compound of the formula (IV) with 100 wt. parts of a ferroelectric liquid crystal material of the formulas (1)–(37). Further, in case where a mixture of two or more mesomorphic compounds of the formula (IV) or a mixture of mesomorphic compounds of the formula (III) and (IV) is used, it is preferred to mix 1–500 wt. parts of such a mixture further with 100 wt. parts of a ferroelectric liquid crystal material of the formulas (1)–(37).

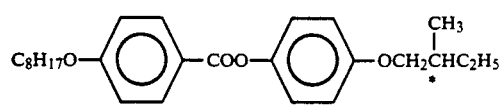 (1)
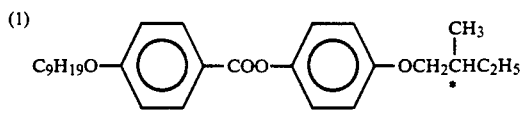 (2)
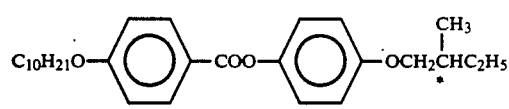 (3)
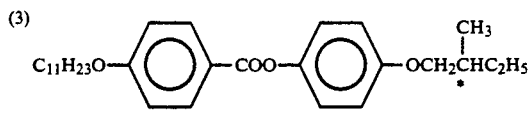 (4)
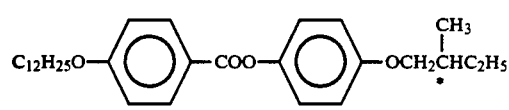 (5)
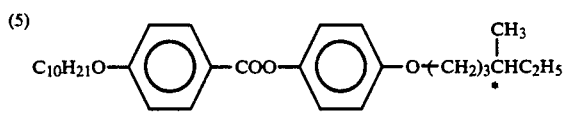 (6)
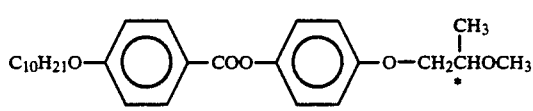 (7)
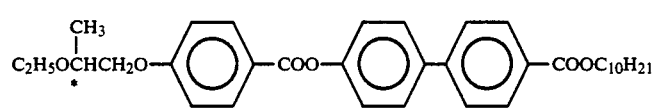 (8)
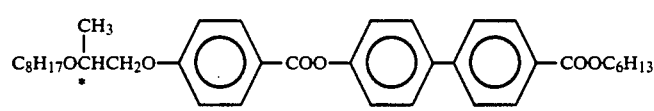 (9)
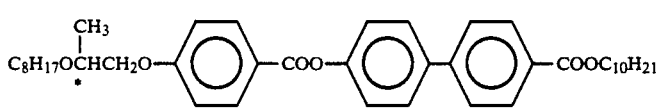 (10)
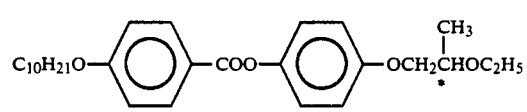 (11)
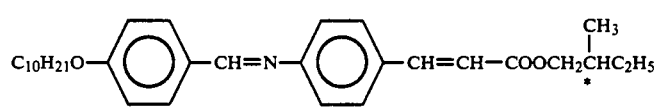 (12)
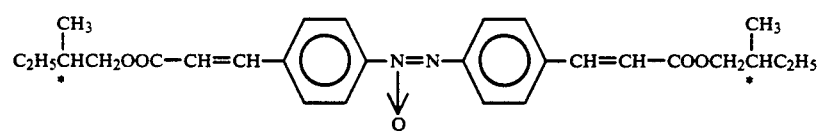 (13)
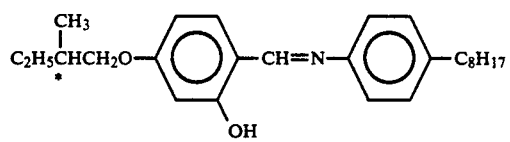 (14)
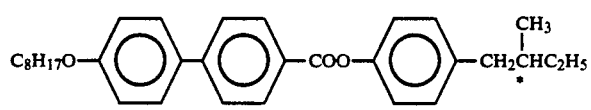 (15)
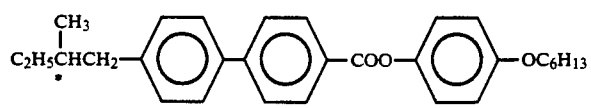 (16)

-continued
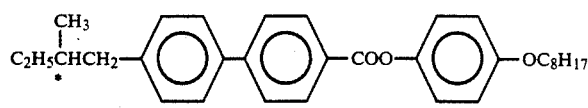 (17)
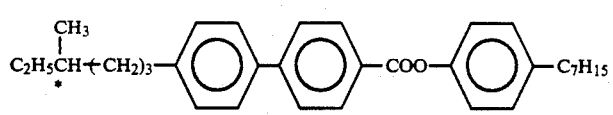 (18)
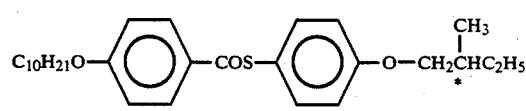 (19)
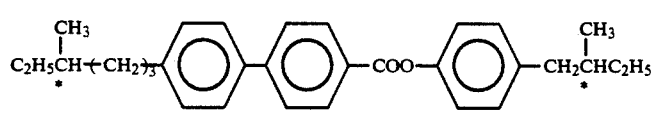 (20)
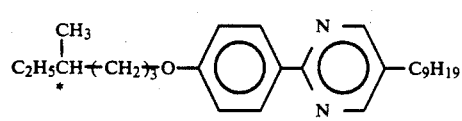 (21)  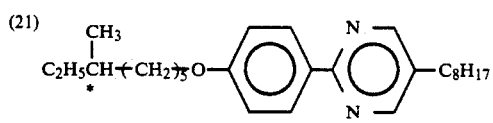 (22)
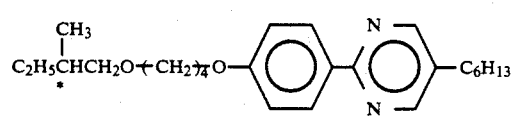 (23)
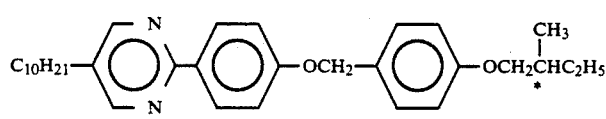 (24)
 (25)  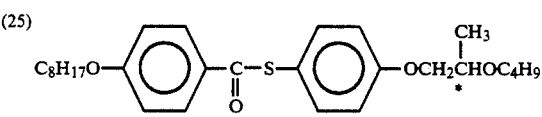 (26)
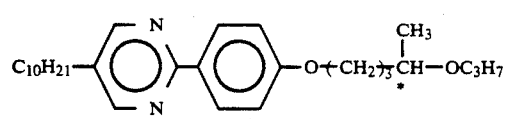 (27)  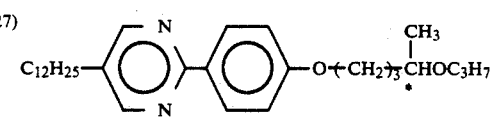 (28)
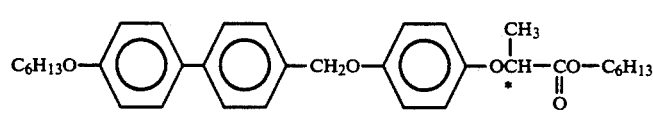 (29)
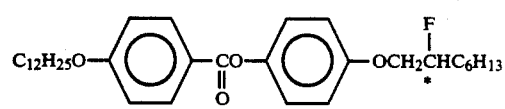 (30)  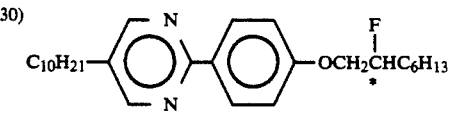 (31)
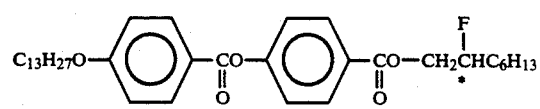 (32)
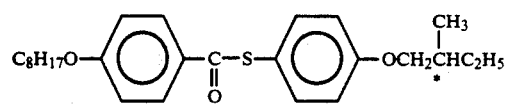 (33)  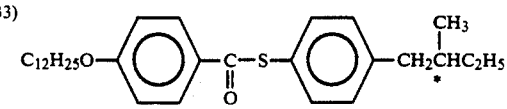 (34)

-continued

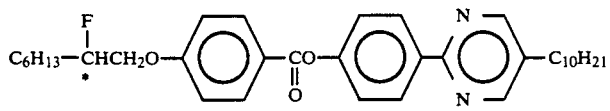
(35)

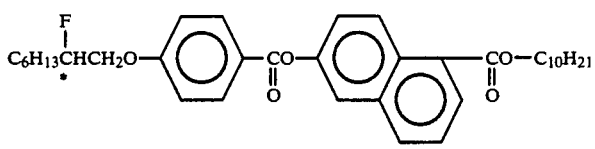
(36)

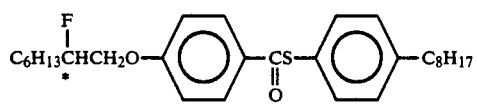
(37)

Further, it is also possible to mix an optically active or mesomorphic compound according to the present invention with a smectic liquid crystal which per se is not chiral as represented by the following formulas 1)–5) to obtain a composition utilizable as ferroelectric liquid crystal.

In such a case, the optically active compound represented by the formula (II) can be used in a proportion of 0.1 to 90 wt. %. Also, the mesomorphic compound of the present invention represented by the formula (III) or (IV) can be used in a proportion of 0.1 to 99 wt. %.

1)

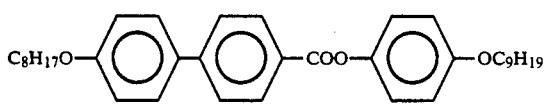

(4-nonyloxyphenyl)-4'-octyloxybiphenyl-4-carboxylate

Cryst. $\underset{74}{\overset{107}{\rightleftarrows}}$ SmB $\overset{117}{\rightleftarrows}$ SmC $\overset{160}{\rightleftarrows}$ SmA $\overset{195}{\rightleftarrows}$ Iso.

2)

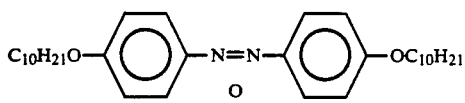

4,4'-decyloxyazoxybenzene

Cryst. $\overset{77}{\rightarrow}$ SmC $\overset{120}{\rightleftarrows}$ N $\overset{123}{\rightleftarrows}$ Iso.

3)

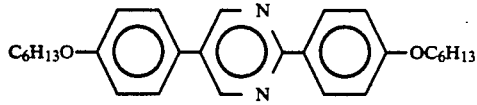

2-(4'-hexyloxyphenyl)-4-(4'-hexyloxyphenyl)pyrimidine

Cryst. $\overset{120}{\rightarrow}$ SmC $\overset{189}{\rightarrow}$ SmA $\overset{216}{\rightarrow}$ Iso.

4)

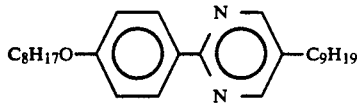

2-(4'-octyloxyphenyl)-5-nonylpyrimidine

Cryst. $\overset{33}{\rightarrow}$ SmC $\overset{60}{\rightarrow}$ SmA $\overset{75}{\rightarrow}$ Iso.

5)

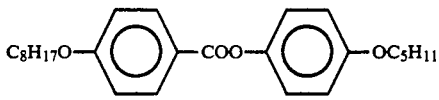

4'-pentyloxyphenyl-4-octyloxybenzoate

Cryst. $\overset{58}{\rightarrow}$ SmC $\overset{64}{\rightarrow}$ SmA $\overset{66}{\rightarrow}$ N $\overset{85}{\rightarrow}$ Iso.

Further, an optically active mesomorphic compound of the formula (III) or (IV) may be effectively added to a nematic liquid crystal in order to prevent the occurrence of a reverse domain in a TN-type cell. In this case, it is preferred to use the mesomorphic compound in a proportion of 0.01–50 wt. % of the resultant composition.

Further, it is possible to add the mesomorphic compound to a nematic liquid crystal or chiral nematic liquid crystal to obtain a chiral nematic liquid crystal composition which may be used in a phase transition-type liquid crystal device or a White-Taylor type guest-host liquid crystal device.

When a device is constituted by using these materials, the device may be supported with a block of copper, etc., in which a heater is embedded in order to realize a temperature condition where the liquid crystal composition assumes, for example, SmC* phase or SmH* phase.

Referring to FIG. 1, there is schematically shown an example of a ferroelectric liquid crystal cell for explanation of the operation thereof. Reference numerals 11a and 11b denote base plates (glass plates) on which a transparent electrode of, e.g., $In_2O_3$, $SnO_2$, ITO (Indium-Tin-Oxide), etc., is disposed respectively. A liquid crystal of a chiral smectic phase such as SmC* or SmH* in which liquid crystal molecular layers 12 are oriented perpendicular to surfaces of the glass plates is hermetically disposed therebetween. A full line 13 shows liquid crystal molecules. Each liquid crystal molecule 13 has a dipole moment (P⊥) 14 in a direction perpendicular to the axis thereof. When a voltage higher than a certain threshold level is applied between electrodes formed on the base plates 11a and 11b, a helical structure of the liquid crystal molecule 13 is released or unwound to change the alignment direction of respective liquid crystal molecules 13 so that the dipole moments ($P\perp$) 14 are all directed in the direction of the electric field. The liquid crystal molecules 13 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 2:
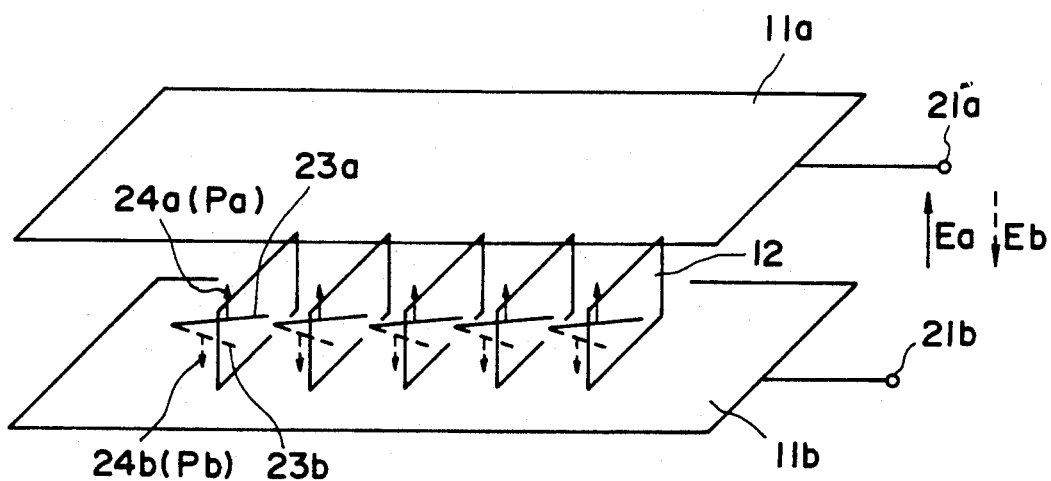

The liquid crystal layer in the liquid crystal device of the present invention may be rendered sufficiently thin in thickness (e.g., less than 10 $\mu$). As the thickness of the liquid crystal layer is decreased, the helical structure of the liquid crystal molecules is unwound even in the absence of an electric field whereby the dipole moment assumes either of the two states, i.e., Pa in an upper direction 24a or Pb in a lower direction 24b as shown in FIG. 2. When electric field Ea or Eb higher than a certain threshold level and different from each other in polarity as shown in FIG. 2 is applied to a cell having the above mentioned characteristics, the dipole moment is directed either in the upper direction 24a or in the lower direction 24b depending on the vector of the electric field Ea or Eb. In correspondence with this, the liquid crystal molecules are oriented to either a first stable state 23a or a second stable state 23b.

When the above-mentioned ferroelectric liquid crystal is used as an optical modulation element, it is possible to obtain two advantages as briefly mentioned hereinbefore. First is that the response speed is quite fast. Second is that the orientation of the liquid crystal shows bistability. The second advantage will be further explained, e.g., with reference to FIG. 2. When the electric field Ea is applied to the liquid crystal molecules, they are oriented to the first stable state 23a. This state is retained stably even if the electric field is removed. On the other hand, when the electric field Eb of which direction is opposite to that of the electric field Ea is applied thereto, the liquid crystal molecules are oriented to the second stable state 23b, whereby the directions of molecules are changed. This state is similarly retained stably even if the electric field is removed. Further, as long as the magnitude of the electric field Ea or Eb being applied is not above a certain threshold value, the liquid crystal molecules are placed in the respective orientation states. In order to effectively realize high response speed and bistability, it is preferable that the thickness of the cell is as thin as possible, generally 0.5 to 20 $\mu$, particularly 1 to 5 $\mu$.

Next, an example of the method for driving a ferroelectric liquid crystal is explained with reference to FIGS. 3-5.

Figure 3:
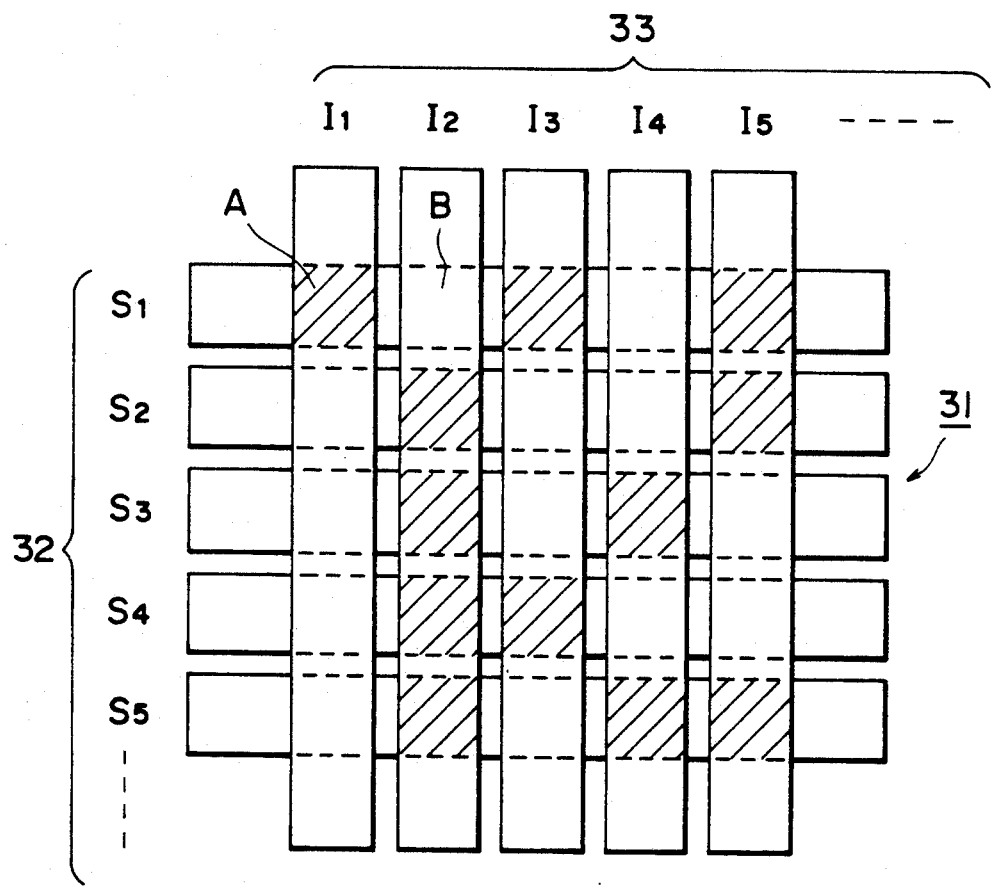
FIG. 3 is a plan view of the matrix electrode structure to be used in the present invention.
Figure 4A:
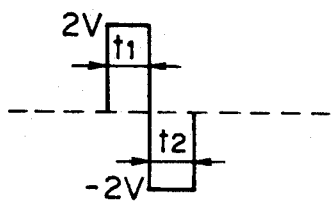
FIGS. 4A–4D illustrate signals to be applied on the matrix electrode.
Figure 4B:
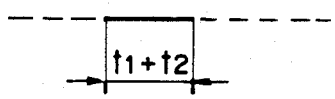
Figure 4C:
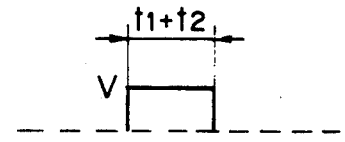
Figure 4D:
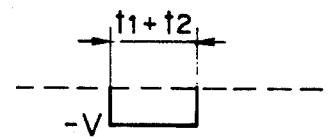

Referring to FIG. 3, there is schematically shown an example of a cell 31 having a matrix electrode arrangement in which a ferroelectric liquid crystal material (not shown) is interposed between a pair of groups of electrodes oppositely spaced from each other. Reference numerals 32 and 33 respectively denote a group of scanning electrodes to which scanning signals are applied and a group of signal electrodes to which information signals are applied. Referring to FIGS. 4A and 4B, there are respectively shown electric signals applied to a selected scanning electrode $S_1$ and electric signals applied to the other scanning electrodes (non-selected scanning electrodes) $S_2$, $S_3$, $S_4$, . . . On the other hand, FIGS. 4C and 4D show electric signals applied to the selected signal electrode $I_1$, $I_3$, $I_5$ and electric signals applied to the non-selected signal electrodes $I_2$, $I_4$, respectively. In FIGS. 4A to 4D and 5A to 5D, the abscissa and the ordinate represent a time and a voltage, respectively. For instance, when displaying a motion picture, the group of scanning electrodes 32 are sequentially and periodically selected. If a threshold voltage for giving a first stable state of the liquid crystal having bistability is referred to as $-V_{th1}$ and a threshold voltage for giving a second state thereof as $+V_{th2}$, an electric signal applied to the selected scanning electrode 32 ($S_1$) is an alternating voltage showing 2 V at a phase (time) $t_1$ and $-2$ V at a phase (time) $t_2$, as shown in FIG. 4A. When such an electric signal having plural phases of mutually different voltages is applied to a selected scanning electrode, an important effect can be obtained that conversion between the first and second stable states corresponding to optically "bright" and "dark" states, respectively, can be quickly caused.

Figure 5A:
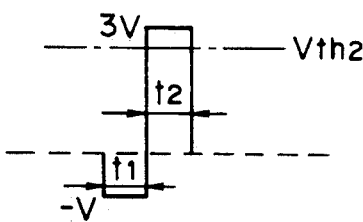
FIGS. 5A to 5D illustrate waveforms of voltage applied between the matrix electrodes.
Figure 5B:
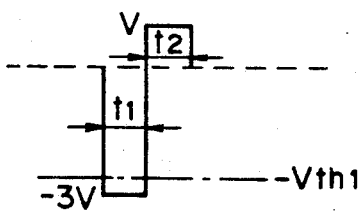

On the other hand, the other scanning electrodes $S_2$-$S_5$ . . . are grounded as shown in FIG. 4B. Accordingly, the electric signals appearing thereon show zero volt. On the other hand, an electric signal applied to the selected signal electrode $I_1$, $I_3$, $I_5$ shows V as indicated in FIG. 4C while an electric signal applied to the non-selected signal electrode $I_2$, $I_4$ shows $-V$ as indicated in FIG. 4D. In this instance, the voltage V is set to a desired value which satisfies $V<V_{th2}<3V$ and $-3V<-V_{th1}<-V$. Voltage waveforms applied to picture elements A and B, for example, among the picture elements shown in FIG. 3 when such electric signals are given are shown in FIGS. 5A and 5B, respectively. Namely, as seen from FIG. 5A, a voltage of 3 V above the threshold level $V_{th2}$ is applied to the ferroelectric liquid crystal at the picture element A on the selected scanning line at a phase $t_2$. Further, a voltage of $-3$ V exceeding the threshold level $-V_{th1}$ is applied to the ferroelectric liquid crystal at the picture element B on the same scanning line at a phase $t_1$. Accordingly, depending upon whether a signal electrode is selected or not on a selected scanning electrode line, the orientation of liquid crystal molecules changes. Thus, when a certain signal electrode is selected, the liquid crystal molecules are oriented to the first stable state, while when not selected, oriented to the second stable state.

Figure 5C:
Figure 5D:
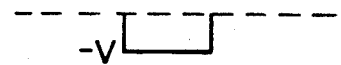

On the other hand, as shown in FIG. 5C and 5D, the voltage applied to all the picture elements on the non-selected scanning lines is $+V$ or $-V$, each not exceeding the threshold level. Accordingly, the ferroelectric liquid crystal molecules electrically connected to the respective picture elements on the non-selected scanning lines are placed in the orientations corresponding to signal states produced when they have been last scanned without change in orientation. Namely, when a certain scanning electrode is selected, signals corresponding to one line are written and thus writing of signals corresponding to one frame is completed. The signal state of each picture element can be maintained until the line is subsequently selected. Accordingly, even if the number of scanning lines increases, the duty ratio does not substantially change, resulting in no possibility of lowering in contrast.

Then, a possible problem which can occur when a device as described above is actually driven as a display device, is considered. Referring to FIG. 3, it is assumed that, among the picture elements formed at intersections of the scanning electrodes $S_1$-$S_5$ . . . and the signal electrodes I$_1$-I$_5$, the picture elements with hatching are in the "bright" state and picture elements drawn in white are in the "dark" state. When display states on a signal electrode I$_1$ in FIG. 3 are noted, a picture element (A) on a scanning electrode S$_1$ is in the "bright" state, and the other picture elements (B) are all in the "dark" state. As a driving mode for obtaining such a display state, FIG. 6 shows an example of the scanning signals, an information signal applied to a signal electrode I$_1$ and a voltage applied to the picture element A in time series.

Figure 6:
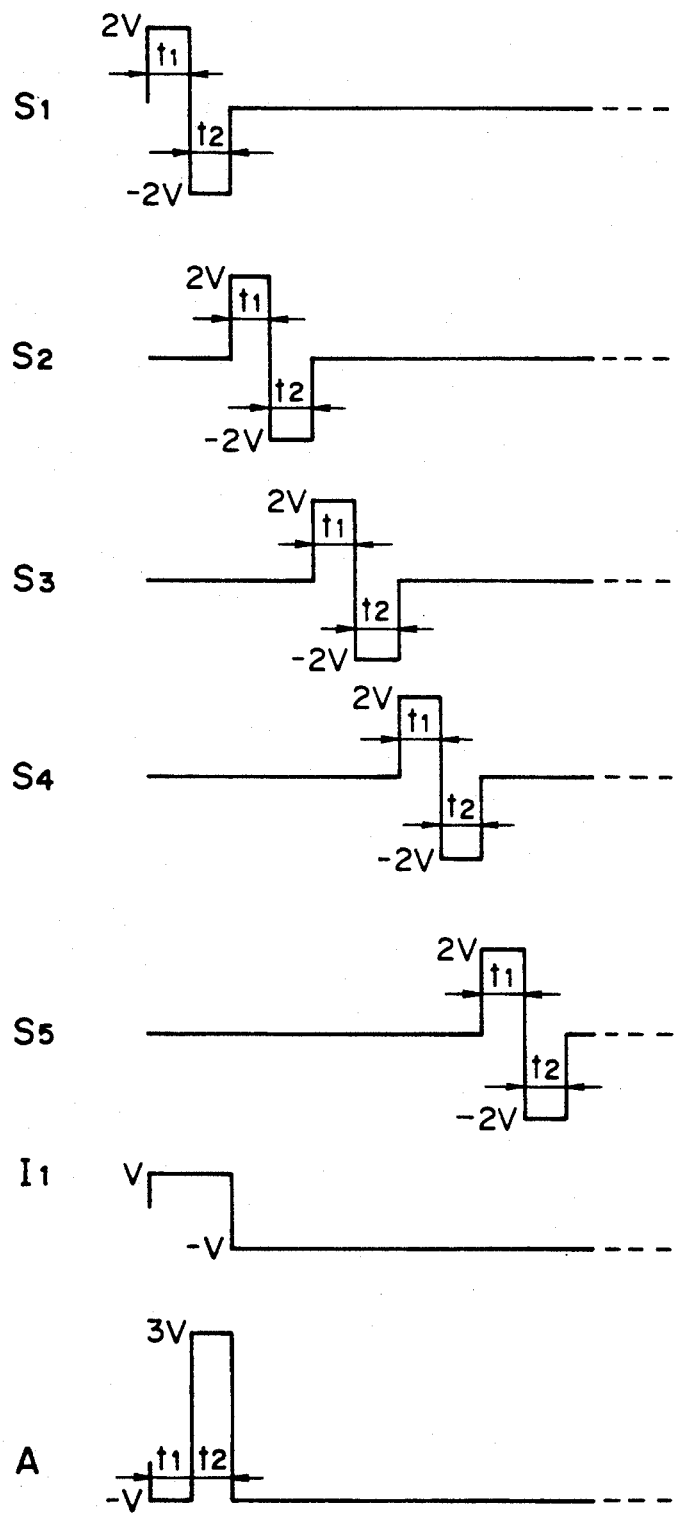
FIG. 6 illustrates a time chart representing an example of voltage signals to be applied on the liquid crystal device of the present invention.

In the driving mode shown in FIG. 6, when a scanning electrode S$_1$ is scanned, a voltage of 3 V exceeding the threshold voltage V$_{th2}$ is applied to the picture element A at time t$_2$, so that the picture element A is oriented or switched to one stable state, i.e., the bright state, regardless of its previous state. After that, during the period when a scanning electrodes S$_2$-S$_5$ . . . are scanned, a voltage of −V is continually applied and the picture element A is expected to keep its "bright" state as the voltage −V does not exceed the threshold voltage −V$_{th1}$. As a matter of actual problem, however, when one direction of signal (one for providing "dark" state in this case) is continually applied to one signal electrode, a reversal of display states can occur especially in a case where a very large number of scanning lines are used and a high speed driving is pursued. Such a reversal phenomenon can be effectively prevented by using the above mentioned specific mesomorphic or liquid crystal compound or a liquid crystal composition containing the same.

Further, in the present invention, for prevention of the reversal phenomenon as mentioned above, it is preferable to form an insulating film formed of an insulating substance on at least one electrode of the opposed electrodes constituting the liquid crystal cell.

The insulating substance to be used in this case is not particularly limited, but it is possible to use inorganic insulating substances such as silicon nitrides, silicon nitrides containing hydrogen, silicon carbides, silicon carbides containing hydrogen, silicon oxides, boron nitrides, boron nitrides containing hydrogen, cerium oxides, aluminum oxides, zirconium oxides, titanium oxides or magnesium fluoride, or organic insulating substances such as polyvinyl alcohol, polyimide, polyamideimide, polyesterimide, polyparaxylene, polyester, polycarbonate, polyvinylacetal, polyvinyl chloride, polyvinyl acetate, polyamide, polystyrene, cellulose resin, melamine resin, urea resin, acrylic resin or photoresist resin as the insulating film. These insulating films may have a thickness of 5000 Å or less, preferably 30 Å to 5000 Å, particularly 50 Å to 3000 Å.

The optically active compound of the formula (I) or (II) according to the present invention can be combined with an intermediate of a functional material having an appropriate intermolecular force and shape without impairing an optical activity and allows arbitrary molecular design. Particularly, by selecting the length of the alkyl group, it is possible to control the kind of and the temperature range for a liquid crystal phase in its mesomorphic state. Further, the liquid crystal composition containing at least one of the optically active (mesomorphic) compound according to the formulas (II)—(IV) of the present invention can be used as the chiral nematic liquid crystal, or chiral smectic liquid crystal to effectively improve the performances such as improvement in low-temperature operation characteristic, response speed, prevention of generation of reverse domain through increased spontaneous polarization, control of viscosity, etc.

The present invention is described in more detail about the optically active compound, mesomorphic compound and liquid crystal compositions by way of examples.

EXAMPLE 1

(R)-3-pentyloxybutanol was prepared in the following manner.

92.1 g of methyl R-(−)-3-hydroxybutyrate and 389 g of pentyl iodide were charged in a flask and mixed under an N$_2$ stream. Freshly prepared Ag$_2$O in an amount of 271 g was added thereto and the mixture was stirred at 60°-65° C. for 26 hours, followed by further addition of 54.2 g of Ag$_2$O and stirring at 60°-65° C. for 58 hours. After the filtration, the product was washed sufficiently with ether, and after the distillation of the ether, subjected to vacuum distillation to obtain 64.6 g of methyl 3-penyloxybutyrate as a fraction at 112°-131° C./59 mmHg.

Then, 9.4 g of LiAlH$_4$ was added to 310 ml of ether, and further thereto, a solution of 63.6 g of methyl 3-pentyloxybutyrate in 61 ml of ether was added dropwise in 2 hours at below 10° C. After the addition, the mixture was stirred at 20°-25° C. for 2.5 hours and then allowed to stand for 15 hours.

Then the mixture was made acidic to pH 1 by addition of aqueous hydrochloric acid solution and subjected to extraction with ether. The ether layer was washed successively with water, 5%-aqueous solution of NaHCO$_3$ and water and dried with MgSO$_4$. After filtration, the product was distilled in vacuo to obtain 34.2 g of 3-pentyloxybutanol as a fraction of 127°-131° C./50 mmHg. The product showed the following IR (infrared absorption) data.

IR (cm$^{-1}$): 3360, 2970-2870, 1370, 1090.

EXAMPLE 2

In a similar manner as in Example 1, (S)-3-propyloxybutanol was obtained:

IR (cm$^{-1}$) 3360, 2970-2870, 1370, 1090.

EXAMPLE 3

(S)-3-dodecyloxybutanol was obtained in a similar manner as in Example 1.

IR (cm$^{-1}$): 3360, 2970-2860, 1370, 1090.

EXAMPLE 4

(S)-4-octyloxypentanol was prepared in the following manner.

98 g of ethyl lactate, 380 g of octyl iodide and 245 g of silver oxide were stirred at 60° C. for 16 hours. After removal of the insoluble matter by filtration, the mixture was distilled in vacuo to obtain 77 g of ethyl 2-octyloxypropionate as a fraction of 110°-130° C./3 mmHg.

Then, 7.5 g of LiAlH$_4$ was added to 250 ml of diethyl ether, followed by stirring for a little while. Then, a solution of 56 g of the above ester in 50 ml of diethyl ether was added dropwise in 2 hours at below 5° C. After the addition, the mixture was stirred at room temperature for 2 hours and allowed to stand for 15 hours. After the reaction, 30 ml of 5% hydrochloric acid was added, and 6N-hydrochloric acid was added to provide a pH of about 1, followed by extraction with ether. The product was washed with water, dried and subjected to removal of the solvent by distillation, followed by vacuum distillation to obtain 39.5 g of 2-octyloxypropanol as a fraction of 107° C./3 mmHg.

Then, to 70 g of the alcohol was added 230 ml of pyridine, and 85 g of tosyl chloride was added under stirring at below 10° C. in 30 minutes. After 15 min. of stirring at that temperature, the mixture was raised in temperature to 20°-24° C. and stirred for 3.5 hours. The product was poured into cold water, extracted with benzene, and washed successively with 5%-hydrochloric acid and water, followed further by drying and distilling-off of benzene to obtain 127 g of 2-octyloxypropyl p-toluenesulfonate (tosylate).

Into 220 ml of ethanol, 26.7 g of 95% sodium ethoxide was added, and under stirring, 73.1 g of 98%-diethyl malonate was added at 36°-38° C. in 50 min. After further 30 min. of stirring, 127 g of the above tosylate was added dropwise at 36°-38° C. in 1 hour. After further 15 min of stirring, the mixture was heated and refluxed for 18 hours. After the reaction, ice-water was poured, and the product was extracted with benzene, followed by washing and drying. By distilling the solvent off, 149 g of ethyl 4-octyloxy-2-thoxycarbonylvalerate (ester) was obtained.

Then, 88.5 g of 85%-KOH was dissolved in 90 ml of water and 149 g of the above ester was added thereto at 20°-25° C. in 50 min., followed by 30 min. of stirring and 2 hours of refluxing. After cooling, the mixture was held below 15° C., and a solution of 153 g of conc. sulfuric acid in 196 ml of water was added dropwise thereto in 1 hour, followed by 30 min. of stirring and 3 hours of refluxing. After cooling to room temperature, the product was extracted with benzene, and the benzene layer was washed with 5% NaOH aqueous solution and added to the aqueous layer. The aqueous layer was acidified to pH 1 with 6N-hydrochloric acid, followed by extraction with benzene, washing with water and drying with anhydrous $MgSO_4$. By distilling off the solvent, 54 g of 4-octyloxyvaleric acid was obtained.

Into 210 ml of dry ether, 10 g of $LiAlH_4$ was added, and under stirring, a solution of the above carboxylic acid in 70 ml of ether was added dropwise in 70 min. while keeping a temperature of 2°-6° C. after the addition, the mixture was raised in temperature to 23° C. and stirred for 3 hours. After standing for 12 hours, 5% hydrochloric acid was added to acidify the mixture while keeping a temperature of below 15° C., and the product was extracted with ether and washed successively with water, 5% NaOH aqueous solution and water, followed by drying with anhydrous $MgSO_4$. By distilling off the solvent and effecting vacuum distillation, 10 g of (S)-4-octyloxypentanol was obtained as a fraction at 150° C./5 mmHg. The product showed the following IR data.

IR ($cm^{-1}$): 3360, 2970-2860, 1460, 1370, 1340, 1080.

EXAMPLES 5 AND 6

In a similar manner as in Example 4, the following products were obtained.

(S)-4-propoxypentanol

IR ($cm^{-1}$): 3370, 2970-2870, 1460, 1370, 1340, 1080.

(S)-4-pentyloxypentanol

IR ($cm^{-1}$): 3360, 2970-2870, 1460, 1370, 1340, 1080.

EXAMPLE 7

Production of (R)-4-propoxypentanol 160 g of methyl D-lactate and 524 g of 1-iodopropane were mixed in a four-necked flask, and 471 g of freshly prepared $Ag_2O$ was gradually added. Then, the mixture was stirred at 60°-65° C. for 1 hour and subjected to filtration. The filtrated product was washed with ether and the ether was distilled off from the filtrate, which was then distilled in vacuo to obtain 161 g of methyl 2-propoxypropionate.

Then, 35.3 g of $LiAlH_4$ was added to 750 ml of ether, followed by 3 hours of stirring, and to the mixture held below 10° C., a solution of 161 g of the above obtained methyl 2-propoxypropionate in 150 ml of ether was added dropwise in 3.5 hours. After the addition, the mixture was stirred at 17°-20° C. for 2.5 hours and allowed to stand for 12 hours at room temperature. The mixture was acidified to pH 1 with 5%-hydrochloric acid aqueous solution and subjected to extraction with ether. The ether layer was washed successively with water, 5% $NaHCO_3$ aqueous solution and water, followed by drying with anhydrous magnesium sulfate and vacuum distillation to obtain 72 g of 2-propoxypropanol as a fraction at 95°-103° C./150 mmHg.

Then, 70 g of 2-propoxypropanol, 114 ml of pyridine and 228 ml of benzene were stirred while being kept below 10° C., and 81.5 g of methanesulfonyl chloride was added in 1 hour. The mixture was raised in temperature to 25°-30° C. and stirred for 3.5 hours. The product was poured into cold water and extracted with ether, followed by successive washing with 5%-hydrochloric acid and water, drying with anhydrous magnesium sulfate, and distillation of ether to obtain 114 g of 2-propoxypropylmethane sulfonate.

Into 345 ml of ethanol, 43.4 g of 95%-sodium ethoxide was added, and under stirring, 114 g of diethyl malonate was added dropwise at 33°-36° C. in 55 min. After further 30 min. of stirring, 114 g of the above 2-propoxypropylmethane sulfonate was added at 34°-38° C. in 1 hour. The mixture was heated and refluxed at 80°-82° C. for 18 hours. After the completion, the product was poured in cold water and extracted with benzene, followed by washing with water, removed by distillation of benzene, and vacuum distillation to obtain 100 g of ethyl 4-propoxy-2-ethoxycarbonylvalerate (75°-115° C./5 mmHg).

Then, 87 g of 85% KOH was dissolved in 87 ml of water, and 100 g of the above ethyl 4-propoxy-2-ethoxycarbonylvalerate was added at 15°-25° C. in 45 min. The mixture was stirred at 90°-96° C. for 2 hours, and then cooled. While keeping the temperature below 20° C., a solution of 138 g of conc. sulfuric acid in 194 ml of water was added dropwise in 30 min. The mixture was stirred at 90°-95° C. for 3 hours, cooled to room temperature and then subjected to extraction with ether. The ether layer was washed with saturated saline water and then ether was distilled off, followed by vacuum distillation to obtain 47 g of a fraction of 100°-130° C./5 mmHg. Benzene was added to the fraction, and the mixture was washed with 5% NaOH aqueous solution. The aqueous layer was acidified to pH 1 with 6N-hydrochloric acid and subjected to extraction with ether. The ether extract was washed with saturated saline water, and ether was distilled off to obtain 38 g of 4-propoxyvaleric acid.

Then, 10.1 g of LiAlH$_4$ was added to 217 ml of dry ether, and under stirring, a solution of the above 4-propoxyvaleric acid in 44 ml of ether was added dropwise at below 10° C. in 3.5 hours. After the addition, the mixture was raised in temperature to 20°-25° C., stirred for 3 hours and then leftstanding for 12 hours. An aqueous 5%-hydrochloric acid solution was added to acidify the mixture (pH 1), which was then subjected to extraction with ether. The ether layer was washed successively with 5%-NaOH aqueous solution and saturated saline water, followed by drying with anhydrous magnesium sulfate, distilling-off of ether and vacuum distillation to obtain 26 g of (R)-4-propoxypentanol as a fraction at 109°-117° C./35 mmHg.

EXAMPLE 8

Production of 5-methoxy-1-hexanol

To 100 g of 3-methoxy-1-butanol, 187 ml of pyridine and 374 ml of benzene were added, and under stirring, 132 g of methanesulfonyl chloride was added below 10° C. in 60 min. After 15 min. of stirring at that temperature, the mixture was raised in temperature to 15°-21° C. and stirred for 3 hours. The mixture was poured into cold water and extracted with benzene. The benzene extract was washed with 5%-hydrochloric acid and water, dried and subjected to distillation of benzene to obtain 173 g of a pale yellow liquid.

Then, 59.4 g of 95% sodium methoxide was added to 220 ml of ethanol, and under stirring, 243 g of diethyl malonate was added thereto at 25°-30° C. in 60 min. After further, 30 min. of stirring, 173 g of the above pale yellow liquid was dropped at 30°-36° C. in 60 min. The mixture was further stirred for 18 hours with refluxing at 80°-82° C. After the reaction, ice-water was poured, and the product was extracted with benzene, washed with water and dried. By distilling off the solvent and effecting vacuum distillation to obtain 190 g of ethyl 5-methoxy-2-ethoxycarbonylcaprylate.

Then, 180 g of 85% KOH was dissolved in 180 ml of water, and 190 g of the above ethyl 5-methoxy-2-ethoxycarbonylcaprylate was dropped at 20°-30° C. in 60 min., followed by 30 min. of stirring and 2 hours of refluxing. After cooling, the mixture was held below 20° C., and a solution of 288 g of conc. sulfuric acid in 406 g of water was dropped in 90 min., followed by 30 min of stirring and 3 hours of refluxing at 90°-95° C. After being cooled to room temperature, the product was extracted with ether. The ether layer was washed with 5%-NaOH aqueous solution and added to the aqueous layer. The aqueous layer was acidified with 6N-hydrochloric acid and extracted with ether, followed by washing with saturated saline water, distilling-off of the ether and vacuum distillation to obtain 53 g of 5-methoxycaprylic acid in the form of a colorless clear liquid.

15.3 g of LiAlH$_4$ was added to 330 ml of dry ether, and under stirring, a solution of 53 g of the above 5-methoxycaprylic acid in 60 ml of dry ether was dropped at below 10° C. in 2 hours. After the dropping, the mixture was raised in temperature for 2 hours of stirring at 15°-20° C. After standing for 12 hours, 5%-hydrochloric acid was added to the mixture for acidification while keeping the temperature below 15° C. The mixture was then subjected to extraction with ether. The ether extract was washed successively with water, 5%-NaOH aqueous solution and water, followed by drying with anhydrous MgSO$_4$, distilling-off of the solvent and vacuum distillation to obtain 24.5 g of 5-methoxy-1-hexanol which provided the following IR data:

IR (cm$^{-1}$): 3370, 2970, 2930, 2860, 2830, 1460, 1373, 1135, 1085.

EXAMPLE 9

Production of 6-pentyloxyheptanol 98 g of ethyl L-lactate, 313 g of 1-iodopentane and 245 g of freshly prepared Ag$_2$O were stirred at 60°-65° C. for 16 hours, and diluted with ether, followed by removal of insoluble matter by filtration. After distilling off the ether, the reaction liquid was distilled in vacuo to obtain 68 g of ethyl 2-pentyloxypropionate.

7.5 g of LiAlH$_4$ was added to 250 ml of ether, and under stirring below 10° C., 46 g of the above ester was dropped in 2 hours. After the addition, the mixture was stirred for 2 hours and left standing overnight. The mixture was acidified to pH 1 with 5%-hydrochloric acid and extracted with ether. The ether layer, after being separated, was dried with anhydrous MgSO$_4$, followd by distilling-off of the ether to obtain 31 g of 2-pentyloxypropanol.

103 g of 2-pentyloxypropanol prepared in a manner as described above was dissolved in 444 ml of pyridine, and at below 10° C., 160 g of p-toluenesulfonyl chloride was added in 50 min. After the addition, the mixture was raised in temperature to 20°-25° C. and stirred for 3 hours. After the reaction, the mixture was poured into cold water, extracted with benzene, and the benzene layer was successively washed with 5% hydrochloric acid and water, followed by drying with anhydrous MgSO$_4$ and distilling-off of benzene to obtain a brown liquid. The liquid was distilled in vacuo to obtain 112 g of ethyl 4-pentyloxy-2-ethoxycarbonylpentanoate (diester) as a fraction of 130°-142° C./5 mmHg.

Then, 88.3 ml of water was added to 88.3 g of 85% KOH, and 112 g of the above diester was dropped in 1.5 hours. After the addition, the mixture was raised in temperature and stirred at 90°-95° C. for 2 hours. A solution of 139 of conc. sulfuric acid in 196 ml of water was dropped in 1 hour at below 20° C. After the addition, the mixture was raised in temperature and stirred at 90°-93° C. for 3 hours. The reaction liquid was extracted with benzene, followed by washing with saturated saline water. After distilling off the benzene, 87 g of a pale yellow liquid was obtained. The liquid was distilled to obtain 57 g of a fraction at 130°-145° C./5 mmHg, which was then made alkalline to pH 11 with 5% NaOH aqueous solution and extracted with benzene. The benzene layer was washed with 5% NaOH aqueous solution, and the washing liquid was added to the aqueous layer, which was then acidified to pH 1 with 6N-hydrochloric acid and subjected to extraction with benzene. The benzene layer was the washed with saturated NaCl aqueous solution and the benzene was removed therefrom by distillation to obtain 49 g of 4-pentyloxypentanoic acid.

Then, 237 ml of ether was added to 11 g of LiAlH$_4$, and under stirring, a solution of 49 g of the above acid in 48 ml of ether was dropped in 2 hours at below 10° C. After the addition, the mixture was raised in temperature to 20°-25° C., stirred for 3 hours and allowed to stand overnight. Below 10° C., the mixture was acidified to pH 1 with 5% hydrochloric acid and extracted with ether, followed by successive washing with water, 5% NaOH aqueous solution and water, drying, and distilling-off of the ether to obtain a pale yellow liquid.

It was distilled in vacuo to obtain 39 g of 4-pentyloxypentanol at 148°–152° C./32 mmHg.

To 32 g of the alcohol was added 113 ml of pyridine, and 42 g of p-toluenesulfonyl chloride was added in 30 min. at below 10° C. After the addition, the mixture was raised in temperature and stirred for 3 hours at 20°–25° C. The reaction liquid was poured in cold water, extracted with benzene, washed successively with 5% hydrochloric acid and water, and dried, followed further by distilling-off of the benzene to obtain 49.5 g of 4-pentyloxypentyl p-toluenesulfonate (tosylate).

Then, 190 ml of ethanol was added to 10.9 g of 95% sodium ethoxide, and 29.8 g of diethyl malonate was dropped at 32°–35° C. in 1 hour. After further 15 min. of stirring at the temperature, 49.5 g of the above tosylate was dropped in 35 min. After the addition, the mixture was raised in temperature and refluxed for 18 hours. After the reaction, the mixture was poured in cold water, extracted with benzene, washed with water and dried, followed further by distilling-off of the benzene and vacuum distillation to obtain 25.8 g of ethyl 6-pentyloxy-2-ethoxycarbonylheptanoate (diester) as a fraction at 153°–163° C./5 mmHg.

Then, 18.6 g of water was added to 18.6 g of 85% KOH, and under stirring, 25.8 g of the above diester was dropped in 30 min. at 20°–23° C. After the addition, the mixture was stirred for 4 hours at the temperature and extracted with benzene. The benzene layer was washed with 5% NaOH aqueous solution and added to the aqueous layer. The aqueous layer was acidified to pH 1 with 6N-hydrochloric acid and extracted with ether. The ether layer was washed with saturated NaCl aqueous solution and dried, followed by distilling-off of the ether to obtain 21.1 g of a slightly yellowish liquid. The liquid was stirred for 3 hours at 160°–170° C., and after cooling, water was added thereto, followed by extraction with benzene. The benzene layer was washed with 5% NaOH aqueous solution and added to the aqueous layer. The aqueous layer was acidified to pH 1 and extracted with ether, followed by washing with saturated NaCl aqueous solution, drying and distilling-off of the solvent to obtain 14.9 g of 6-pentyloxyheptanoic acid in the form of a yellow liquid.

3.0 g of LiAlH$_4$ was added to 62 ml of ether, and at below 10° C. under stirring, a solution of 14.9 g of the above acid in 12 ml of ether was dropped in 1 hour. After the addition, the mixture was raised in temperature to 20°–25° C., stirred for 6 hours and left standing overnight. Then mixture was acidified to pH 1 with addition of 5% hydrochloric acid and extracted with ether. The ether layer was washed successively with water, 5% NaOH aqueous solution and water, followed further by drying and distilling-off of the solvent to obtain 14 g of a liquid, which was then distilled in vacuo to obtain 11.5 g of 6-pentyloxyheptanol as a fraction at 129°–131° C./5 mmHg. The product showed the following IR data.

IR (neat) (cm$^{-1}$): 3380, 2970–2860, 1460, 1370, 1340, 1080.

EXAMPLE 10

4-(3-pentyloxybutoxy)phenol was prepared in the following manner.

75 ml of dry pyridine and 19 g of 3-pentyloxybutanol obtained in the above Example 1 were charged in a flask and cooled with ice under stirring, into which 27 g of p-toluenesulfonyl chloride was added little by little. After 2 hours of stirring, the mixture was restored to room temperature and was reacted for 4 hours. After 15 hours of standing, the reaction mixture was added to ice-cooled 5% HCl aqueous solution, and after stirring, the mixture was subjected to extraction with benzene, followed by drying with anhydrous Na$_2$SO$_4$. Then, the benzene was distilled off to obtain 36.5 g of oily 3-pentyloxybutyl p-toluenesulfonate.

19.2 g of hydroquinone and 8 g of 85% KOH were added to a mixture of 31 ml of methanol and 156 ml of ethanol, followed by stirring. Thereto, a solution of 36.5 g of 3-pentyloxybutyl p-toluenesulfonate obtained by the above reaction in 20 ml of ethanol was added, and the mixture was stirred for 2 hours at 60°–70° C., followed by heat-refluxing for 7 hours. Then, the product was poured into cold water and extracted with hexane. The hexane layer was washed with 5% NaOH aqueous solution, and the NaOH aqueous solution layer was added to the previous aqueous layer. The resultant aqueous layer was acidified to a pH of about 1 with hydrochloric acid and subjected to extraction with ether. The ether layer was washed with water and dried with anhydrous MgSO$_4$, followed by distilling-off of the ether. The remaining liquid was purified by silica gel column chromatography with the use of a 1:1 mixture of hexane and ether as a eluent to obtain 10 g of 4-(3-pentyloxybutoxy)phenol, which provided the following IR data.

IR (cm$^{-1}$): 3350, 2960–2870, 1510, 1450, 1230, 1100, 825.

EXAMPLE 11

4-(3-propyloxybutoxy)phenol was prepared in a similar manner as in Example 10.

IR (cm$^{-1}$): 3340, 2970–2870, 1510, 1450, 1230, 1100, 825.

EXAMPLE 12

Production of 4-(3-pentyloxybutoxycarbonyl)phenol 10 g of p-acetyloxybenzoic acid was added to 45 ml of benzene, and 11.8 g of PCl$_5$ was added little by little under stirring at room temperature. After 8.5 hours of heat-refluxing thereafter, the solvent was distilled off to obtain 11.5 g of p-acetyloxybenzoic acid chloride.

Separately, 9.0 g of 3-pentyloxybutanol and 6.82 g of N,N-dimethylaniline were added to 20 ml of ether, and under stirring at room temperature, 11.5 g p-acetyloxybenzoic acid chloride was added thereto dropwise. Then, the mixture was heat-refluxed for 3.5 hours. The crystal was dissolved by adding 50 ml of water and extracted with ether. The ether layer was washed successively with 10% H$_2$SO$_4$ aqueous solution and water and dried with anhydrous Na$_2$SO$_4$, followed by distilling-off of the solvent to obtain 17.5 g of 4-(3-pentyloxybutoxycarbonyl)phenyl acetate.

The acetate ester was dissolved by 50 ml of methanol, and a 1:1 mixture of methanol and 28% ammoniacal aqueous solution was added thereto under stirring. After distilling off the solvent, the product was charged in 150 ml of water and extracted with ether. The ether layer was washed with water and dried with anhydrous Na$_2$SO$_4$, followed by distilling off the solvent to obtain 13.6 g of an oily product. It was purified by silica gel column chromatography by using a mixture of n-hexane:isopropyl ether in a proportion ranging from 10:1 to 1:1 (gradient) as an eluent, thereby to obtain 12.5 of 4-(3-pentyloxybutoxycarbonyl)phenol.

IR (cm$^{-1}$): 3350, 2970–2870, 1710, 1610, 1290, 1170.

EXAMPLE 13

4-(4'-pentyloxypentyloxy)phenol was prepared in the following manner.

17 g of 4-pentyloxypentanol was dissolved in 60 ml of pyridine, and under stirring, 22.4 g of tosyl chloride was added at below 10° C. in 40 min. The mixture was raised to 25° C. and stirred for 3 hours. After the reaction, cold water was added, and the product was extracted with ether, followed by successive washing with 5% hydrochloric acid and water and drying with anhydrous MgSO$_4$. The solvent was distilled off to obtain 31.9 g of 4-pentyloxypentyl p-toluenesulfonate.

Then, 16.1 g of hydroquinone, 6.6 g of 85% KOH, 30 ml of methanol and 120 ml of ethanol were dissolved together, and at 50°–55° C., a solution of 31.9 g of the above tosylate in ethanol was dropped in 40 min. After the addition, the mixture was raised to 65° C. and stirred for further 2 hours. The mixture was refluxed for 7 hours and, after cooling, poured into cold water. The product was extracted with hexane, washed with 5% NaOH aqueous solution and added to the aqueous layer. The aqueous layer was acidified to pH 1 with 6N-hydrochloric acid, extracted with hexane, washed with water and dried with anhydrous MgSO$_4$. The solvent was distilled off to obtain 10 g of a brown liquid, which was then purified by silica gel column chromatography by using a developer of ether:hexane=3:1 to obtain 8.5 g of 4-(4'-pentyloxypentyloxy)phenol. The product showed the following IR data:

IR (cm$^{-1}$): 3350, 2960–2870, 1510, 1450, 1380, 1230, 1100, 820.

EXAMPLE 14

4-(4'-propyloxypentyloxycarbonyl)phenol was prepared in the following manner.

In a solution of 19.7 g of p-acetoxybenzoic acid in 120 ml of benzene, 23.4 g of phosphorus pentachloride was added little by little under stirring at room temperature. Thereafter, the mixture was heat-refluxed for 4 hours, and the solvent was distilled off to obtain 21.5 g of an acid chloride.

Then, 16.0 g of 4-propoxypentanol and 13.3 g of N,N-dimethylaniline were dissolved in 32 ml of ether, and under stirring at room temperature, 21.5 g of the above acid chloride was dropped in 40 min. After the addition, 2.5 hours of heat-refluxing was effected. After the reaction, the crystal was dissolved by adding 80 ml of water and extracted with ether. The ether layer was washed successively with 10% sulfuric acid and water and dried with anhydrous Na$_2$SO$_4$, followed by distilling-off of the solvent to obtain 33.9 g of an oily product, which was then purified by silica gel column chromatography with a mixture of hexane and isopropyl ether in a proportion ranging from 2:1 to 1:1 (gradient), whereby 23.9 g of an ester was obtained.

Then, 23.9 g of the above ester was dissolved in 80 ml of methanol, and a 1:1 mixture of methanol and 28% ammoniacal aqueous solution was added thereto under stirring. After the reaction, the product was extracted with ether, washed with water and dried with anhydrous Na$_2$SO$_4$. The solvent was distilled off to obtain 18 g of 4-(4'-propyloxypentyloxycarbonyl)phenol, which showed the following IR data.

IR (cm$^{-1}$): 3350, 2970–2870, 1720, 1615, 1590, 1520, 1280, 1170, 1100.

EXAMPLE 15

4'-(3-pentyloxybutoxy)phenyl 4-hexyloxybenzoate

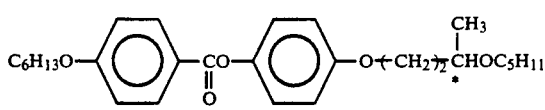

The above mesomorphic compound was produced in the following manner.

7.1 ml of thionyl chloride was added to 2 g of 4-hexyloxybenzoic acid, and the mixture was refluxed for two hours, followed by removal of excessive thionyl chloride by distillation to obtain an acid chloride.

Then, 2.2 g of 4-(3-pentyloxybutoxy)phenol was dissolved in 11 ml of pyridine, and at below 94° C., a solution of the acid chloride obtained through the above reaction in 8 ml of toluene was added dropwise. Then, the mixture was stirred for 15 hours at room temperature. After the reaction, the reaction mixture was poured into cold water and extracted with ether.

The ether layer was washed successively with 5% hydrochloric acid aqueous solution, water, 5%-NaOH aqueous solution and water and dried with anhydrous Na$_2$SO$_4$, followed by distilling-off of the solvent to obtain 3.7 g of a crude product. The product was purified by silica gel column chromatography (chloroform:hexane=2:1) to obtain 1.8 g of 4'-(3-pentyloxybutoxy)phenyl 4-hexyloxybenzoate.

IR (cm$^{-1}$): 2960–2870, 1730, 1600, 1500, 1250, 1195, 1165.

EXAMPLE 16

4'-(3-pentyloxybutoxy)phenyl 4-octyloxybenzoate

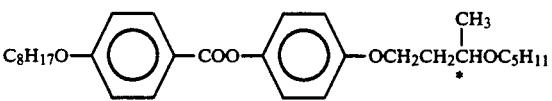

The above mesomorphic compound was prepared in a similar manner as in Example 15 and provided the following IR data.

IR (cm$^{-1}$): 2960–2850, 1730, 1600, 1500, 1250, 1190, 1160, 1070.

EXAMPLE 17

5-nonyl-2-[4'-(3''-pentyloxybutoxy)phenyl]pyrimidine

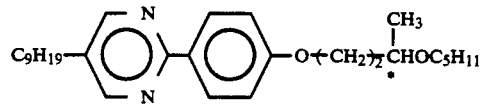

5.0 g of 3-pentyloxybutanol, 3.98 g of p-toluenesulfonyl chloride, 1.65 g of pyridine, and 8 ml of benzene were charged in a 30 ml-reaction vessel and, under N$_2$ stream, stirred for 23 hours at room temperature. Then, into the reaction mixture, 6.3 ml of hot conc. NaOH aqueous solution was added and stirred for 5 min. The mixture was poured in 280 ml of cold 10%-hydrochloric acid solution and extracted with hexane. The hexane layer was washed successively with cold 5%-hydrochloric acid solution, saturated NaCO$_3$ aqueous solution and water and dried with anhydrous MgSO$_4$, followed by distilling-off of the solvent to 6.0 g of a crude product, which was purified by alumina column chromatography (hexane) to obtain 2.3 g of 3-pentyloxybutyl p-toluenesulfonate.

Separately, 2.27 g of 5-nonyl-2-(4'-hydroxyphenyl)-pyrimidine, 0.5 g of KOH and 15 ml of DMF (dimethylformamide) were stirred under heating at 100° C. for 3 hours. Then, 3.0 g of the above tosylate was added, and the mixture was stirred for further 3 hours at 100° C. After the reaction, the reaction mixture was poured in 400 ml of cold water and extracted with benzene. The benzene layer was dried with anhydrous MgSO$_4$ and the benzene was distilled off. The residue was treated with alumina column by using hexane as eluent to obtain 3.0 g of a crude product, which was purified by silica gel column chromatography (hexane: isopropyl ether=10:1) to obtain 1.3 g of a liquid. The liquid was recrystallized from ethanol at a low temperature to obtain 0.86 g of 5-nonyl-2-[4'-(3''-pentyloxybutoxy)-phenyl]pyrimidine, which provided the following IR and NMR data:

IR (cm$^{-1}$): 2970–2870, 1620, 1590, 1440, 1260.

NMR (ppm, CDCl$_3$): 8.7–6.8 (6H), 4.4–2.3 (7H), 2.1–0.7 (31H).

EXAMPLE 18

5-octyl-2-[4'-(3''-dodecyloxybutoxy)phenyl]pyrimidine

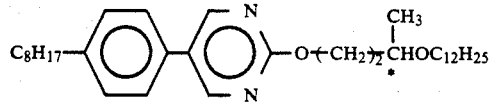

The above mesomorphic compound was prepared in a similar manner as in Example 17 and provided the following data.

IR (cm$^{-1}$): 2970–2850, 1615, 1590, 1430, 1260.

NMR (ppm, CDCl$_3$): 8.7–6.8 (6H), 4.4–2.3 (7H), 2.1–0.7 (43H).

EXAMPLE 19

3-dodecyloxybutyl 4-(4'-dodecyloxyphenyl)benzoate

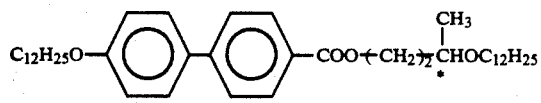

In a solution of 2.97 g of 4-(4'-dodecyloxyphenyl)benzoic acid in 10 ml of benzene, 1.65 g of PCl$_5$ was added little by little under stirring at room temperature. Thereafter, the mixture was heat-refluxed for 5 hours, and the solvent was distilled off to obtain 5.5 g of an acid chloride.

Then, 1.88 g of 3-dodecyloxybutanol was dissolved in 16 ml of pyridine, and at 5° C., a solution of 3.3 g of the above acid chloride in 10 ml of toluene was dropped, followed by 23 hours of stirring at room temperature. After the reaction, the reaction mixture was poured on ice and acidified with 6N-hydrochloric acid, and the resultant precipitate was filtered out. The organic layer was washed successively with water, 2N-NaOH aqueous solution and water and dried with anhydrous MgSO$_4$, followed by distilling-off of the solvent to obtain 4.1 g of a crude product. The product was purified by silica gel chromatography (hexane:isopropyl ether=5:1) and recrystallized from ethanol to obtain 1.2 g of 3-dodecyloxybutyl 4-(4'-dodecyloxyphenyl)benzoate.

IR (cm$^{-1}$): 2970, 2850, 1720, 1615, 1475, 1290.

NMR (ppm, CDCl$_3$) 8.2–6.8 (4H), 4.6–3.1 (7H), 2.2–0.7 (51H).

EXAMPLE 20

4-(3-pentyloxybutoxycarbonyl)phenyl 4-(4'-decyloxyphenyl)benzoate

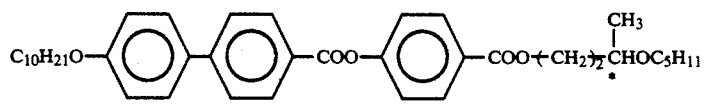

Into a solution of 3.5 g of 4-(4'-decyloxyphenyl)benzoic acid in 10 ml of benzene, 2.1 g of PCl$_5$ was added little by little under stirring at room temperature. Thereafter, the mixture was heat-refluxed for 3.5 hours, and the solvent was distilled off to obtain 3.8 g of an acid chloride.

Then, 2.77 g of 4-(3-pentyloxybutoxycarbonyl)-phenol was dissolved in 16 ml of pyridine, and at 5° C., a solution of 3.8 g of the above acid chloride in 10 ml of toluene was dropped. The mixture was then stirred for 7.5 hours at room temperature. After the reaction, the reaction mixture was poured on ice and acidified with 6N-HCl solution, and the resultant precipitate was filtered out. The organic layer was washed successively with water, 2N-NaOH aqueous solution and water and dried with anhydrous Na$_2$SO$_4$, followed by distilling-off of the solvent to obtain 5.8 g of a crude product. The product was purified by silica gel chromatography (chloroform) and recrystallized from ethyl acetate to obtain 1.06 g of 4-(3-pentyloxybutoxycarbonyl)phenyl 4-(4'-decyloxyphenyl)benzoate.

IR (cm$^{-1}$): 2970–2860, 1740, 1725, 1605, 1290, 1270.

NMR (ppm, δ): 8.4–6.9 (12H), 4.7–3.1 (7H), 2.2–0.7 (33H).

EXAMPLE 21

4-(3-pentyloxybutoxycarbonyl)phenyl 4-dodecyloxybenzoate

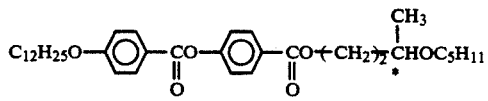

Into a solution of 3.5 g of 4-dodecyloxybenzoic acid in 10 ml of benzene, 2.43 g of PCl$_5$ was added little by little under stirring at room temperature. Thereafter, the mixture was heat-refluxed for 3.5 hours, and the solvent was distilled off to obtain 3.8 g of an acid chloride.

Then, 3.20 g of 4-(3-pentyloxybutoxycarbonyl)-phenol was dissolved in 16 ml of pyridine, and at 2° C., a solution of 3.8 g of the above acid chloride in 10 ml of toluene was dropped. The mixture was then stirred for 7.5 hours at room temperature. After the reaction, the reaction mixture was poured on ice and acidified with 6N-HCl solution, and the resultant precipitate was filtered out. The organic layer was washed successively with water, 2N-NaOH aqueous solution and water and dried with anhydrous $Na_2SO_4$, followed by distilling-off of the solvent to obtain 6.3 g of a crude product. The product was purified by silica gel chromatography (chloroform) to obtain 2.0 g of a crystal. It was further recrystallized from ethyl acetate to obtain 1.4 g of 4-(3-pentyloxybutoxycarbonyl)phenyl 4-dodecyloxybenzoate.

IR ($cm^{-1}$): 2970–2860, 1735, 1730, 1620, 1280.

NMR (ppm, $CDCl_3$): 8.3–6.8 (8H), 4.6–3.1 (7H), 2.1–0.6 (37H).

EXAMPLE 22

A liquid crystal composition was prepared by mixing 80 wt. % of

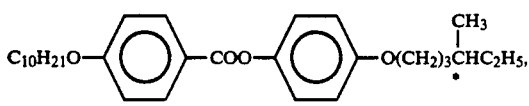

and 20 wt. % of the mesomorphic compound obtained by the above Example 20. The liquid crystal composition showed SmC* phase in the range of 60°–44° C. in the course of cooling.

EXAMPLE 23

4"-(3-pentyloxybutyloxycarbonyl)phenyl t-4-(4'-n-octylphenyl)cyclohexylcarboxylate

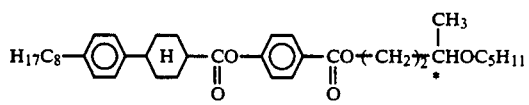

The above compound was prepared in the following manner.

2.0 g of t-(4-(4'-n-octylphenyl)cyclohexylcarboxylic acid was heat-refluxed together with 5 ml of thionyl chloride for 2.5 hours, and thereafter, nonreacted thionyl chloride was distilled off under vacuum to obtain an acid chloride.

Separately, 1.84 g of 3-pentyloxybutanol was dissolved in 5.4 ml of pyridine and 10 ml of toluene, and under stirring at 0°–4° C., a solution of the above acid chloride in 5 ml of toluene was dropped in 40 min, followed further by 2 hours of stirring at room temperature. The reaction mixture was poured into ice-water and extracted with ethyl acetate. The extract was washed successively with 6N-hydrochloric acid, water, 6%-sodium bicarbonate aqueous solution and water, followed by drying with anhydrous sodium sulfate and distilling-off of the solvent to obtain a crude product. The product was further purified by silica gel column chromatography (n-hexane: ethyl acetate=10:2) and recrystallized from ethyl acetate-ethanol to obtain 1.45 g of the objective product in the form of a white viscous substance.

IR ($cm^{-1}$): 2930, 2850, 1760, 1720, 1614, 1270, 1202, 1160, 1110, 1004.

Phase transition temperature:

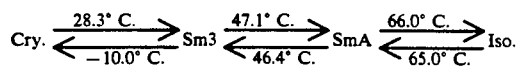

EXAMPLE 24

5-octyl-2-[4-(4'-octyloxypentyloxy)phenyl]pyrimidine was prepared in the following manner.

7 g of 4-octyloxypentanol, 4.34 g of p-toluenesulfonyl chloride, 1.8 g of pyridine and 10 ml of benzene were stirred under $N_2$ stream at room temperature for 22 hours. Thereafter, 6.5 ml of hot conc. NaOH aqueous solution was added to the reaction mixture and stirred for 5 min. Then, the mixture was poured into cold 10%-hydrochloric acid and extracted with hexane. The hexane layer was washed successively with cold 5%-hydrochloric acid, saturated $NaHCO_3$ aqueous solution and water and dried with anhydrous $MgSO_4$. After removing the solvent by distillation, the product was treated with alumina column (hexane) to obtain 6.6 g of 4-octyloxypentyl p-toluenesulfonate.

Separately, 5.75 g of 5-octyl-2-(4-hydroxyphenyl)-pyrimidine, 1.007 g of KOH and 28 ml of DMF were stirred for 50 min. at 100° C., and 6.0 g of the above tosylate was added thereto, followed by further 2.5 hours of stirring at 100° C. After the reaction, the mixture was poured into 500 ml of cold water and extracted with benzene. The benzene layer was dried with anhydrous $MgSO_4$ and the solvent was distilled off. The product was treated with alumina column (hexane) to obtain 3.1 g of a crystal, which was then recrystallized from ethanol to obtain 1.62 g of 5-octyl-2-[4-(4'-octyloxypentyloxy)phenyl]pyrimidine. The product showed the following IR data and NMR data:

IR ($cm^{-1}$): 2970–2860, 1610, 1590, 1440, 1260.

NMR ($CDCl_3$) δ: 8.5–6.8 (6H), 4.2–2.3 (7H), 2.1–0.6 (37H) ppm.

EXAMPLES 25–26

The following compounds were obtained in a similar manner as in Example 24 and provided the following IR and NMR data respectively.

·5-decyl-2-[4-(4'-propoxypentyloxy)phenyl]pyrimidine

IR ($cm^{-1}$): 2970–2860, 1610, 1590, 1440, 1260.

NMR ($CDCl_3$) δ: 8.6–6.8 (6H), 4.2–2.3 (7H), 2.1–0.6 (31H).

·5-nonyl-2-[4-(4'-pentyloxypentyloxy)phenylpyrimidine

IR ($cm^{-1}$): 2970–2860, 1610, 1590, 1440, 1260.

NMR ($CDCl_3$) δ: 8.6–6.8 (6H), 4.2–2.3 (7H), 2.1–0.6 (33H).

EXAMPLE 27

4-octyloxypentyl 4-(4'-decyloxyphenyl)benzoate was prepared in the following manner.

Into a solution of 3.28 g of 4-(4'-decyloxyphenyl)benzoic acid in 10 ml of benzene, 1.97 g of $PCl_5$ was added little by little under stirring at room temperature. Thereafter, the mixture was heat-refluxed for 6 hours, and the solvent was distilled off to obtain 3.6 g of an acid chloride.

Then, 2.0 g of 4-octyloxypentanol was dissolved in 16 ml of pyridine, and at 2° C., a solution of the above acid chloride in 10 ml of toluene was dropped. The mixture was then stirred for 7 hours at room temperature. After the reaction, the reaction mixture was poured in ice-water and acidified with 6N-HCl solution, and the resultant precipitate was filtered out. The organic layer was washed successively with water, 2N-NaOH aqueous solution and water and dried with anhydrous $MgSO_4$, followed by distilling-off of the solvent and purification by silica gel column chromatography (hexane:ethyl acetate=20:1) to obtain 2.7 g of crystal, which was then recrystallized from ethanol to obtain 1.2 g of 4-octyloxypentyl 4-(4'-decyloxyphenyl)benzoate. The product showed the following IR and NMR data:

IR (cm$^{-1}$): 2970–2860, 1720, 1610, 1290, 1200 1120.

NMR (CDCl$_3$) δ: 8.3–6.9 (8H), 4.6–3.2 (7H), 2.2–0.7 (41H).

EXAMPLE 28

4-(4'-pentyloxypentyloxy)phenyl 4-octyloxybenzoate was prepared in the following manner.

8 ml of thionyl chloride was added to 2.5 g of 4-octyloxybenzoic acid, and the mixture was refluxed for 2 hours. Excessive thionyl chloride was distilled off to obtain an acid chloride.

Then, the acid chloride dissolved in toluene was dropped into a solution of 2.6 g of 4-(4'-pentyloxypentyloxy)phenol in 12 ml of pyridine at below 10° C. in 15 min. After the addition, the mixture was stirred at room temperature for 15 hours. After the reaction, the mixture was poured into cold water and extracted with ether. The ether layer was washed successively with 5%-hydrochloric acid, water, 5%-NaOH aqueous solution and water and dried with anhydrous Na$_2$SO$_4$. After distilling off the solvent, the product was recrystallized from ethanol to obtain 4.4 g of 4-(4'-pentyloxypentyloxy)phenyl 4-octyloxybenzoate.

IR (cm$^{-1}$): 2960–2860, 1730, 1600, 1510, 1470, 1250, 1190, 1070, 760.

EXAMPLES 29-30

The following compounds were obtained in a similar manner as in Example 28 and provided the following IR data:

4-(4'-pentyloxypentyloxy)phenyl 4-decyloxybenzoate

IR (cm$^{-1}$): 2970–2850, 1730, 1600, 1510, 1470, 1250, 1190, 1070, 760.

4-(4'-pentyloxypentyloxyphenyl) 4-(4'-dodecyloxyphenyl)benzoate.

IR (cm$^{-1}$): 2970–2850, 1730, 1600, 1510, 1470, 1250, 1190, 1070, 760.

EXAMPLE 31

4-(4'-propoxypentyloxycarbonyl)phenyl 4-octyloxybenzoate was prepared in the following manner.

Into a solution of 4.0 g of 4-octyloxybenzoic acid in 13 ml of benzene, 3.40 g of PCl$_5$ was added little by little under stirring at room temperature. Thereafter, the mixture was heat-refluxed for 4 hours, and the solvent was distilled off to obtain 4.6 g of an acid chloride.

Then, 4.26 g of 4-(4'-propoxypentyloxycarbonyl)phenol was dissolved in 20 ml of pyridine, and at 3° C., a solution of 4.6 g of the above acid chloride in 13 ml of toluene was dropped. The mixture was then stirred for 18 hours at room temperature. After the reaction, the reaction mixture was poured into ice-water and acidified with 6N-HCl solution; and the resultant precipitate was filtered out. The organic layer was washed successively with water, 2N-NaOH aqueous solution and water and dried with anhydrous Na$_2$SO$_4$, followed by distilling-off of the solvent to obtain 5.8 g of a crude product. The product was purified by silica gel chromatography (chloroform) and recrystallized from ethanol to obtain 1.16 g of 4-(4'-propoxypentyloxycarbonyl)phenyl 4-octyloxybenzoate.

IR (cm$^{-1}$): 2970–2860, 1730, 1720, 1610, 1270.

NMR (CDCl$_3$) δ: 8.3–6.8 (8H), 4.5–3.1 (7H), 2.2–0.7 (27H) ppm.

EXAMPLES 32-33

The following compounds were obtained in a similar manner as in Example 31 and provided the following IR and NMR data respectively:

4-(4'-propoxypentyloxycarbonyl)phenyl 4-dodecyloxybenzoate

IR (cm$^{-1}$): 2970–2860, 1730, 1720, 1610, 1270.

NMR (CDCl$_3$) δ: 8.3–6.8 (8H), 4.5–3.1 (7H), 2.2–0.7 (35H) ppm.

4-(4'-propoxypentyloxycarbonyl)phenyl 4-(4'-octyloxyphenyl)benzoate

IR (cm$^{-1}$): 2970–2860, 1730, 1720, 1610, 1270.

NMR (CDCl$_3$) δ: 8.3–6.8 (12H), 4.5–3.1 (7H), 2.2–0.7 (27H) ppm.

EXAMPLE 34

Production of 5-dodecyl-2-[4-(4-propoxypropyloxy)phenyl]pyrimidine 15 g of (R)-4-propoxypentanol was dissolved in 50 ml of pyridine, and 21.3 g of p-toluenesulfonyl chloride was added thereto while keeping the temperature below 15° C. by ice-cooling. Then, the mixture was raised to room temperature and stirred for 15 hours. Thereafter, the reaction mixture was poured into 500 ml of ice-water under stirring, acidified to pH 1–2 by the addition of 5% hydrochloric acid, and extracted with methylene chloride. The methylene chloride layer was washed with water and dried with anhydrous magnesium sulfate, followed by distilling-off of the solvent to obtain 14.4 g of (R)-4-propoxypropyl p-toluenesulfonate.

Separately, 2.5 g of 5-dodecyl-2-(4-hydroxyphenyl)pyrimidine, 0.49 g of 85% KOH and 20 ml of N,N-dimethylformamide were mixed and stirred for 1 hour at 100° C. Then, 2.0 g of the above tosylate was added thereto and stirred for 5 hours at 100° C. After the reaction, the mixture was poured into 250 ml of cold water and extracted with isopropyl ether. The isopropyl ether layer was washed with water, dried with anhydrous magnesium sulfate, and the solvent was distilled off. The product was treated by silica gel column chromatography (developer: n-hexane/ethylacetate=10/2) and recrystallized from n-hexane to obtain 1.77 g of 5-dodecyl-2-[4-(4-propoxypropyl)phenyl]pyrimidine.

Phase transition temperature (°C.):

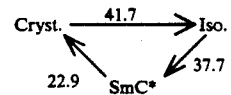

EXAMPLE 35

Production of 4-(4-pentyloxy)pentyloxyphenyl p-(t-4-n-octylcyclohexyl)benzoate 6 ml of thionyl chloride was added to 1.55 g of p(t-4-n-octylcyclohexyl)benzoic acid, and the mixture was heat-refluxed for 4 hours. Excessive thionyl chloride was distilled off in vacuo to obtain p-(t-4-n-octylcyclohexyl)benzoic acid chloride.

1.29 g of 4-(4-amyloxy)-amyloxyphenol was dissolved in 10 ml of toluene and 7 ml of pyridine and cooled with ice. A solution of the p-(t-4-n-octylcyclohexyl)benzoic acid chloride dissolved in 20 ml of toluene was added dropwise to the above mixture at below 5° C. in 30 min. Then, the mixture was stirred for 15 hours at room temperature.

The reaction mixture was charged into 100 ml of ice-water, and the organic layer was washed successively with 6N-HCl aqueous solution, water, 5% NaHCO$_3$ aqueous solution and water, followed by drying with anhydrous magnesium sulfate and distilling-off of the solvent to obtain 3.22 g of a cream-colored crystal.

The crystal was purified by silica gel column chromatography (n-hexane/ethyl acetate=10:1) and recrystallized from a mixture solvent of ethanol/ethyl acetate=5:1 to obtain 0.61 g of 4-(4-amyloxy)-amyloxyphenyl p-(t-4-n-octylcyclohexyl)benzoate.

IR (cm$^{-1}$): 2924, 2852, 1728, 1612, 1506, 1470, 1274, 1248, 1192, 1178, 1072.

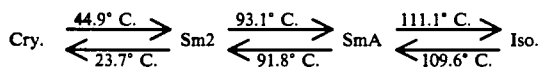

EXAMPLE 36

Synthesis of 5-n-decyl-2-4-(6-pentyloxyheptyloxy)-phenyl]pyrimidine 2.04 g of 6-pentyloxyheptanol was dissolved in 8 ml of pyridine and cooled with ice. Then, 2.26 g of tosyl chloride dissolved in 5 ml of pyridine was gradually dropped in 7 min. at below 5° C. The mixture was then stirred for 5 hours at room temperature.

The above reaction mixture was poured in 150 ml of ice-water and acidified to a pH of about 3 with 6N-hydrochloric acid aqueous solution, followed by extraction with ethyl acetate. The extract was washed with water and dried with anhydrous magnesium sulfate, followed by distilling-off of the solvent to obtain 2.98 g of 6-pentyloxyheptyl p-toluenesulfonate.

3.12 g of 5-n-decyl-2-(4-hydroxyphenyl)pyrimidine and 0.53 g of potassium hydroxide were dissolved in 14 ml of dimethylformamide, and the mixture was stirred for 3 hours, under heating at 100° C. Then 2.98 g of 6-pentyloxyheptyl p-toluenesulfonate was added and stirred for 5 hours under heating at 100° C. The reaction mixture was poured in 200 ml of ice-water and acidified to a pH of about 3, followed by extraction with benzene. The extract was washed with water and dried with anhydrous magnesium sulfate, followed by distilling-off of the solvent to obtain 4.71 g of a crude product. The product was purified by silica gel column chromatography (n-hexane/ethyl acetate=10/2) and recrystallized from hexane to obtain 1.56 g of 5-n-decyl-2-[4-(6-pentyloxyheptyloxy)phenyl-pyrimidine.

IR (cm$^{-1}$: 2924, 2852, 1610, 1586, 1472, 1436, 1254, 1168, 1096, 798.

Phase transition temperature (°C.):

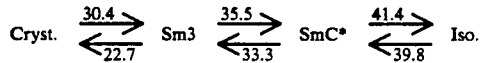

In a similar manner, the following compounds are synthesized:
5-n-octyl-2-[4-(6-pentyloxyheptyloxy)phenyl]pyrimidine; 5-n-octyl-2-[4-(6-ethoxyheptyloxy)phenyl]pyrimidine; 5-n-decyl-2-[4-(6-octyloxyheptyloxy)phenyl]pyrimidine; 5-n-dodecyl-2-4-(6-pentyloxyheptyloxy)-phenyl]pyrimidine; 5-n-decyl-2-[4-(6-ethoxyheptyloxy)-phenyl]pyrimidine; 5-n-decyl-2-[4-(6-butoxyheptyloxy)-phenyl]pyrimidine; 5-n-octyl-2-4-(6-butoxyheptyloxy)-phenyl]pyrimidine; and 5-n-decyl-2-4-(6-dodecyloxyheptyloxy)phenyl]pyrimidine.

EXAMPLE 37

4'-(6-pentyloxyheptyloxy)phenyl 4-n-dodecyloxybenzoate was synthesized through the following two steps.

Step 1

Synthesis of 4-(6-pentyloxyheptyloxy)phenol

In a solution of 3 g of 6-pentyloxyheptanol in 10 ml of pyridine, 3.4 g of p-toluenesulfonyl chloride was added in 30 min. at 0°–5° C. After the addition, the mixture was stirred for 5 hours at an increased temperature of 20°–25° C. After the reaction, the mixture was poured in cold water, acidified with 6N-hydrochloric acid and extracted with ethyl acetate. The extract was washed with water and dried with anhydrous MgSO$_4$, followed by distilling-off of the ethyl acetate to obtain 4.36 g of 6-pentyloxyheptyl p-toluenesulfonate.

2.3 g of hydroquinone, 0.94 g of 85% KOH, 4 ml of methanol and 20 ml of ethanol were stirred at 50°–53° C., and 4.36 g of the above tosylate was dropped in 1 hour. After the addition, the mixture was stirred for 2 hours at 60°–65° C. and for 5 hours at 76°–78° C. After the reaction, the mixture was poured into cold water, acidified to pH 1 with 6N-hydrochloric acid and extracted with hexane. After being washed with water, the extract was dried with anhydrous MgSO$_4$, and the solvent was distilled off. The product was further purified by silica gel column chromatography (hexane/ethyl acetate=10/3) to obtain 2.05 g of 4-(6-pentyloxyheptyloxy)phenol.

IR (cm$^{-1}$): 3350, 2980–2870, 1520, 1460, 1240, 1100, 830.

Step 2

Synthesis of 4'-(6-pentyloxyheptyloxy)phenyl 4-n-dodecyloxybenzoate 7 ml of thionyl chloride was added to 2.14 g of 4-n-dodecyloxybenzoic acid, and the mixture was refluxed for 2 hours. Excessive thionyl chloride was distilled off under vacuum to obtain an acid chloride.

2 g of the phenol derivative synthesized in the above Step 1 was dissolved in 8 ml of pyridine, and under stirring at below 5° C., a solution of the above acid chloride in 10 ml of toluene was dropped in 30 min. After the addition, the mixture was stirred for 20 hours at room temperature, acidified to pH 1 with 6N-hydrochloric acid and extracted with hexane, followed further by washing with water and drying. After distilling off the solvent, the product was purified by silica gel column chromatography (hexane/ethyl acetate=20/1) to obtain 1 g of 4'-(6-pentyloxyheptyloxy)phenyl 4-n-dodecyloxybenzoate.

IR (cm$^{-1}$): 3000–2860, 1730, 1615, 1520, 1475, 1280, 1200, 1170, 1080, 870, 855, 830, 770.

Phase transition temperature (°C.):

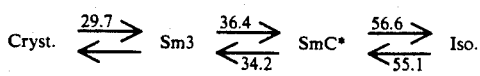

The following compounds are synthesized in a similar manner.

4'-(6-pentyloxyheptyloxy)phenyl 4-n-octyloxybenzoate, 4'-(6-ethoxyheptyloxy)phenyl 4-n-octyloxybenzoate, 4'-(6-butoxyheptyloxy)phenyl 4-n-octyloxybenzoate, 4'-(6-octyloxyheptyloxy)phenyl 4-n-octyloxybenzoate, 4'-(6-pentyloxyheptyloxy)phenyl 4-n-decyloxybenzoate, 4'-(6-ethoxyheptyloxy)phenyl 4-n-decyloxybenzoate, 4'-(6-octyloxyheptyloxy)phenyl 4-n-decyloxybenzoate, 4'-(6-octyloxyheptyloxy)phenyl 4-n-dodecyloxybenzoate, and 4'-(6-ethoxyheptyloxy)phenyl 4-n-dodecyloxybenzoate.

EXAMPLE 38

4'-(6-pentyloxyheptyloxycarbonyl)phenyl 4-ndodecyloxybenzoate was synthesized through the following reaction steps (1), (2) and (3).

Step 1

Synthesis of 6-pentyloxyheptyl p-acetoxybenzoate 2.70 g of p-acetoxybenzoate and 7 ml of thionyl chloride were heat-refluxed together for 4.5 hours, followed by distilling-off of excessive thionyl chloride to obtain an acid chloride. Then, 3.0 g of 6-pentyloxyheptanol was dissolved in 6 ml of pyridine and 16 ml of toluene, and under stirring at 2°-5° C., a solution of the above acid chloride in 6 ml of toluene was dropped in 45 min. The mixture was further stirred for 17 hours at room temperature.

The reaction mixture was poured in ice-water and extracted with ethyl acetate. The organic layer was washed successively with 6N-hydrochloric acid, water, 6%-sodium bicarbonate aqueous solution and water, followed by drying with anhydrous sodium sulfate and distilling-off of the solvent. The resultant pale yellow liquid was purified by silica gel column chromatography (develop: n-hexane/ethyl acetate=10/2) to obtain 4.5 g of 6-pentyloxyheptyl p-acetoxybenzoate (diester).

IR (cm$^{-1}$): 2930, 2850, 1772, 1725, 1608, 1372, 1274, 1198, 1160, 1116, 1102.

Step 2

Synthesis of 6-pentyloxyheptyl p-hydroxybenzoate 4.3 g of the diester obtained in the above step (1) was dissolved in 10 ml of isopropyl ether, 0.86 g of butylamine was added thereto, and the mixture was leftstanding overnight.

The mixture was then washed with water and dried with anhydrous magnesium sulfate, followed by distilling-off of the solvent. The resultant red liquid was purified by silica gel column chromatography (developer: methylene chloride/ethyl acetate=9/1) to obtain 3.56 g of 6-pentyloxyheptyl p-hydroxybenzoate.

IR (cm$^{-1}$): 3350, 2930, 2850, 1712, 1680, 1608, 1594, 1312, 1274, 1160, 1102, 852, 771.

Step 3

4'-(6-pentyloxyheptyloxycarbonyl)phenyl 4-n-dodecyloxybenzoate 9 ml of thionyl chloride was added to 3.4 g of 4-n-dodecyloxybenzoic acid, and the mixture was heat-refluxed for 4.5 hours, followed by distilling-off of excessive thionyl chloride under vacuum to obtain an acid chloride. Then, 3.3 g of 6-pentyloxyheptyl p-hydroxybenzoate was dissolved in 8 ml of pyridine and 17 ml of toluene, and under stirring at 2°-5° C., a solution of the above acid chloride in 8 ml of toluene was dropped in 45 min., followed by standing overnight at room temperature. The reaction mixture was poured in ice-water, extracted with ethyl acetate, and the organic layer was successively washed with 6N-hydrochloric acid, water and 6%-NaHCO$_3$ aqueous solution and water. After drying with anhydrous magnesium sulfate and distilling-off of the solvent, a yellow solid was purified by silica gel column chromatography (hexane/ethyl acetate=10/1) to obtain 2.3 g of 4'-(6-pentyloxyheptyloxycarbonyl)phenyl 4-n-dodecyloxybenzoate.

IR (cm$^{-1}$): 3480, 2940, 2860, 1730, 1722, 1608, 1280, 1216, 1170, 1072, 762.

Phase transition temperature (°C.):

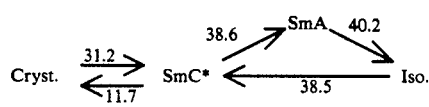

The following compounds are synthesized in a similar manner.

4'-(6-pentyloxyheptyloxycarbonyl)phenyl 4-n-octyloxybenzoate, 4'-(6-ethoxyheptyloxycarbonyl)phenyl 4-n-octyloxybenzoate, 4'-(6-octyloxyheptyloxycarbonyl)phenyl 4-n-octyloxybenzoate, 4'-(6-pentyloxyheptyloxycarbonyl)phenyl 4-n-decyloxybenzoate, 4'-(6-ethoxyheptyloxycarbonyl)phenyl 4-n-decyloxybenzoate, 4'-(6-octyloxyheptyloxycarbonyl)phenyl 4-n-decyloxybenzoate, 4'-(6-ethoxyheptyloxycarbonyl)phenyl 4-n-dodecyloxybenzoate, and 4'-(6-octyloxyheptyloxycarbonyl)phenyl 4-n-dodecyloxybenzoate.

EXAMPLE 39

On the respective opposed ITO matrix electrodes in the form of cross stripes were provided polyimide films having 1000 Å film thickness (formed by coating 5 wt. % N-methylpyrrolidone solution of a polyamic acid resin comprising a condensation product of pyromellitic anhydride and 4,4'-diaminodiphenyl ether and subjecting it to heating ring closure reaction at 250° C.), and the surfaces of the polyimide films were subjected to rubbing so that they were parallel to each other to prepare a cell with a cell thickness of 1 μ.

Subsequently, the following composition A was injected into the above cell according to the vacuum injection method and the cell was sealed. Then, the cell was cooled gradually (1° C./hour) to prepare a liquid crystal cell of SmC*.

Liquid crystal composition A

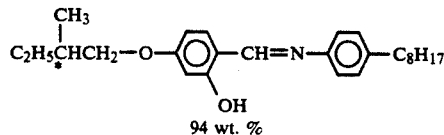

94 wt. %

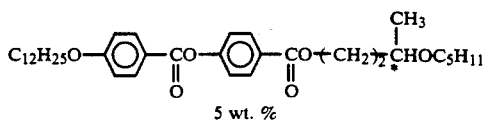

5 wt. %

-continued

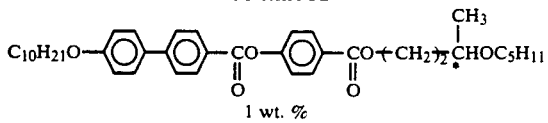

1 wt. %

With a polarizer and an analyzer of crossed nicols being arranged on both sides of the liquid crystal cell, the signals with the waveforms as shown in FIG. 4 and FIG. 5 were applied between the opposed matrix electrodes. During this operation, the scanning signal was one having an alternating waveform of +8 volts and −8 volts as shown in FIG. 4A, while the writing signals were 4 volts and −4 volts, respectively. Also, one frame period was made 30 msec.

As the result, even when this liquid crystal device was subjected to the memory driving type multiplexing driving as described above, a normal motion display could be obtained without any reversal of the writing state at all.

EXAMPLE 40

A liquid crystal device was prepared in the same manner as in Example 39 except that the following liquid crystal composition B was used instead of the liquid crystal composition A, and applied to a motion picture display in the same manner as in Example 39, whereby no reversal phenomenon in the written picture was observed.

Liquid crystal composition B

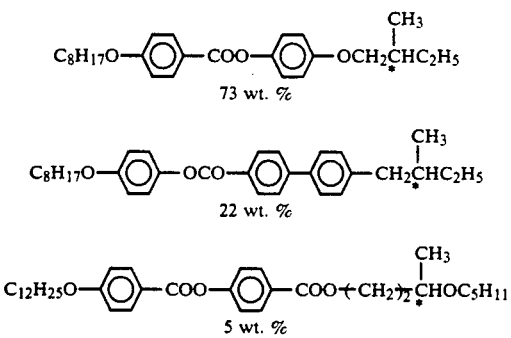

EXAMPLE 41

A liquid crystal device was prepared in the same manner as in Example 39 except that the following liquid crystal composition C was used instead of the liquid crystal composition A, and applied to a driving in the same manner as in Example 39.

Liquid crystal composition C

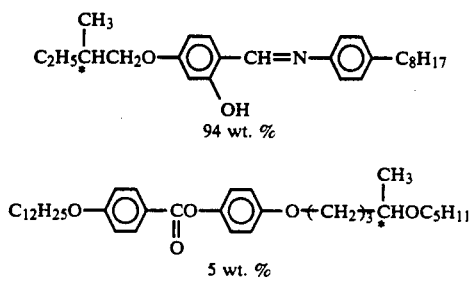

-continued

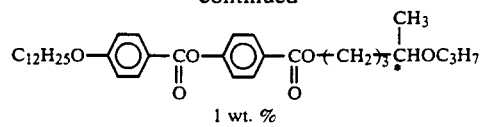

1 wt. %

As the result, even when this liquid crystal device was subjected to the memory driving type multiplexing driving as described above, a normal motion picture display could be obtained without any reversal of the writing state at all.

EXAMPLE 42

A liquid crystal device was prepared in the same manner as in Example 39 except that the following liquid crystal composition D was used intead of the liquid crystal composition A, and applied to a motion picture display in the same manner as in Example 39, whereby no reversal phenomenon in the written picture was observed.

Liquid crystal composition D

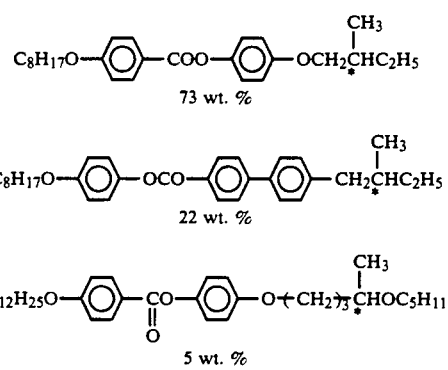

EXAMPLE 43

A liquid crystal device was prepared in the same manner as in Example 39 except that the following liquid crystal composition E was used instead of the liquid crystal composition A, and applied to a driving in the same manner as in Example 39.

Liquid crystal composition E

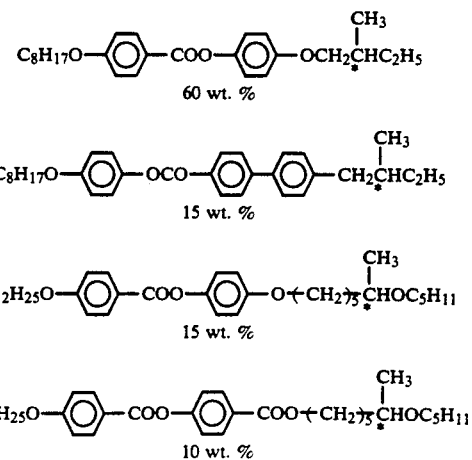

As the result, even when this liquid crystal device was subjected to the memory driving type multiplexing driving as described above, a normal motion picture display could be obtained without any reversal of the writing state at all.

COMPARATIVE EXAMPLE 1

A liquid crystal device was made by preparing a liquid crystal B for comparative purpose as shown below, in which the mesomorphic compound represented by the above formula (III) was omitted from the liquid crystal composition A used in making the liquid crystal device of Example 39. When the liquid crystal device was driven in the same manner as described above, normal motion display could not be effected due to occurrence of reversal phenomenon.

Liquid crystal F for comparison

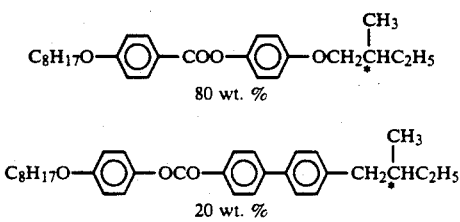

EXAMPLE 44

A twisted nematic (TN) cell prepared by using a liquid crystal mixture comprising 2 wt. parts of 4-(3-pentyloxybutoxycarbonyl)phenyl 4-(4'-decyloxyphenyl)benzoate added to 98 wt. parts of p,p'-pentylazoxybenzene was observed to provide a nematic phase with greatly reduced reverse domain as compared with a TN cell prepared without addition of the former compound.

EXAMPLE 45

A TN cell prepared by using a liquid crystal mixture comprising 1 wt. part of 4-(3-pentyloxybutoxycarbonyl)phenyl 4-(4'-decyloxyphenyl)benzoate added to 99 parts by weight of Lixon GR-63 (biphenyl liquid crystal mixture produced by Chisso K.K.) was observed to provide a nematic phase with greatly reduced reverse domain as compared with a TN cell prepared without addition of the former compound.

EXAMPLE 46

A twisted nematic (TN) cell prepared by using a liquid crystal mixture comprising 2 wt. parts of 4-(4'-pentyloxypentyloxy)phenyl 4-dodecyloxybenzoate added to 98 wt. parts of p,p'-pentylazoxybenzene was observed to provide a nematic phase with greatly reduced reverse domain as compared with a TN cell prepared without addition of the former compound.

EXAMPLE 47

A TN cell prepared by using a liquid crystal mixture comprising 1 wt. part of 4-(4'-pentyloxypentyloxy)phenyl 4-dodecyloxybenzoate added to 99 parts by weight of Lixon GR-63 (biphenyl liquid crystal mixture produced by Chisso K.K.) was observed to provide a nematic phase with greatly reduced reverse domain as compared with a TN cell prepared without addition of the former compound.

EXAMPLE 48

A TN cell prepared by using a liquid crystal mixture comprising 1 wt. part of 4'-(6-pentyloxyheptyloxy)phenyl 4-n-dodecyloxybenzoate added to 99 parts by weight of Lixon GR-63 (biphenyl liquid crystal mixture produced by Chisso K.K.) was observed to provide a nematic phase with greatly reduced reverse domain as compared with a TN cell prepared without addition of the former compound.

EXAMPLE 49

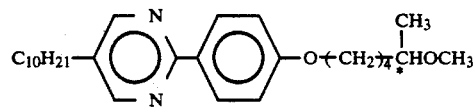

The above compound (Compound Ex. 21 shows before) classified under the general formula (IV) was prepared in the following manner.

In a solution of 1.06 g (8.0 mmol) of 5-methoxyhexanol dissolved in 5 ml of pyridine, 1.83 g (9.6 mmol) of p-toluenesulfonyl chloride dissolved in 5 ml of pyridine was dropped at below 5° C. on an ice-water bath. The mixture was stirred for 6 hours at room temperature and then poured into 100 ml of cold water. The mixture was then acidified by 6N-hydrochloric acid and extracted with isopropyl ether. The organic layer was washed with water and dried with anhydrous magnesium sulfate, followed by distilling off the solvent to obtain 5-methoxyhexyl p-toluenesulfonate.

2.0 g (6.41 mmol) of 5-decyl-2-(p-hydroxyphenyl)-pyrimidine and 0.61 g of potassium chloride were added to 10 ml of dimethylformamide, and the mixture was stirred for 40 min. at 80° C. Into the mixture, the above-obtained 5-methoxyhexyl p-toluenesulfonate was added and stirred under heating at 100° C. for 4 hours. After the reaction, the reaction mixture was poured into 100 ml of cold water and extracted with benzene, followed by washing with water, drying with anhydrous magnesium sulfate, and distilling-off of the solvent to obtain a pale yellow oily product. The product was purified by silica gel column chromatography (ethyl acetate/benzene=1/9) and recrystallized from hexane to obtain 1.35 g of 5-decyl-2-[4-(5'-methoxyhexyloxy)phenyl pyrimidine of the above formula.

Phase transition temperature (°C.):

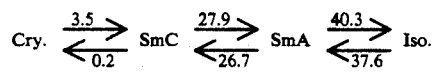

EXAMPLE 50

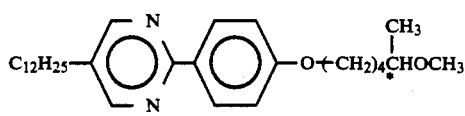

5-dodecyl-2-[4-(5'-methoxyhexyloxy)phenyl]pyrimidine of the above formula (Compound Ex. 21 shown before) classified under the general formula (IV) was prepared in the same manner as in Example 45 except that 5-dodecyl-2-(p-hydroxyphenyl)pyrimidine was used instead of 5-decyl-2-(p-hydroxhphenyl)pyrimidine.

Phase transition temperature (°C.):

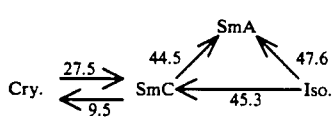

EXAMPLE 51

Two 0.7 mm-thick glass plates were respectively coated with an ITO film to form an electrode for voltage application and further with an SiO$_2$ film vapor-deposited thereon. The glass plates were further coated with a 0.2% solution of a silane coupling agent (KBM-602, mfd. by Shinetsu Kagaku K.K.) in isopropyl alcohol by a spinner coater rotating at a speed of 2000 r.p.m. for 15 seconds and subjected to a heat-drying treatment at 120° C. for 20 minutes.

The thus treated glass plates with ITO films were further coated with a 2% solution of a polyimide precursor (SP-510, mfd. by Toray K.K.) in dimethylacetamide by a spinner coater rotating at a speed of 2000 r.p.m. for 15 seconds, followed by 60 minutes of heating at 300° C. for condensation and curing to obtain an about 700 Å-thick film. The films were rubbed with acetate fiber-planted cloth and washed with isopropyl alcohol. Alumina beads with an average particle size of 2 μm were dispersed one of the thus treated glass plates and the other plate was superposed thereon so that their rubbing axes were in parallel with each other. The two plates were then bonded to each other with a bonding sealant (Lixon Bond, mfd. by Chisso K.K.), followed by heating at 100° C. for 60 min. to prepare a blank cell. The cell gap was measured to be about 2 μ by means of a Berek phase plate.

Then, the following composition including the compound produced in the above Example 49 heated into isotropic phase was injected into the blank cell under vacuum and cooled at a rate of 5° C./hour to 25° C. to prepare a ferroelectric liquid crystal device.

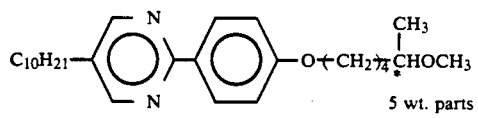

5 wt. parts (5-decyl-2-[4-(5'-methoxyhexyloxy)phenyl]pyrimidine)

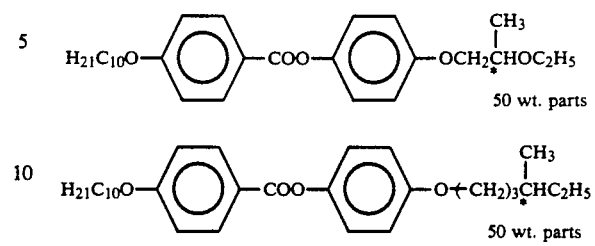

50 wt. parts 50 wt. parts

The ferroelectric liquid crystal device was used in combination with right angle cross nicol polarizers to measure an optical response time in terms of a period in which the transmittance changes from 0 to 90% under the application of a peak-to-peak voltage of 20 volts (hereinafter simply referred to as "optical response time"). The results are shown below:

| 20° C. | 30° C. | 40° C. |
|---|---|---|
| 385 μsec | 330 μsec | 285 μsec |

COMPARATIVE EXAMPLE 2

A ferroelectric liquid crystal device was prepared and the otpical response time thereof was measured in the same manner as in Example 51 except that a composition obtained by omitting the first compound (5-decyl-2-[4-(4'-methoxyhexyloxy)phenyl]pyrimidine) from the composition of Example 51 was used. The results are shown below.

| 20° C. | 30° C. | 40° C. |
|---|---|---|
| 420 μsec | 380 μsec | 325 μsec |

EXAMPLE 52

A ferroelectric liquid crystal device was prepared and the optical response time thereof was measured in the same manner as in Example 51 except that the following composition was used:

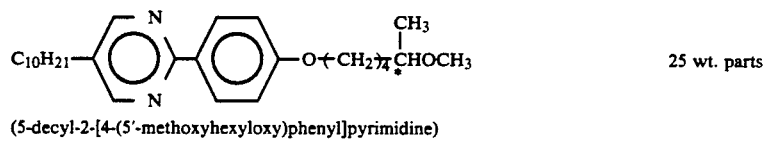

25 wt. parts (5-decyl-2-[4-(5'-methoxyhexyloxy)phenyl]pyrimidine)

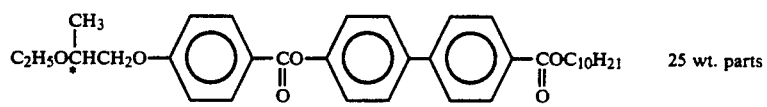

25 wt. parts

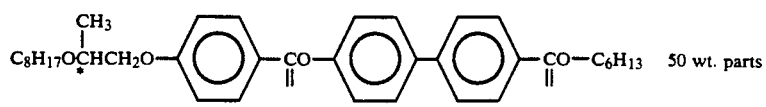

50 wt. parts

-continued

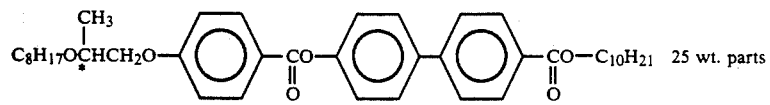 25 wt. parts

The results are as follows.

| 25° C. | 35° C. | 50° C. |
|---|---|---|
| 560 μsec | 360 μsec | 180 μsec |

| 25° C. | 35° C. | 45° C. |
|---|---|---|
| 2300 μsec | 1750 μsec | 1350 μsec |

COMPARATIVE EXAMPLE 3

A ferroelectric liquid crystal device was prepared and the optical response time thereof was measured in the same manner as in Example 52 except that a composition obtained by omitting the first compound (5-decyl-2-[4-(5'-methoxyhexyloxy)phenyl]pyrimidine from the composition of Example 52 was used. The results are shown below.

COMPARATIVE EXAMPLE 4

A ferroelectric liquid crystal device was prepared and the optical response time thereof was measured in the same manner as in Example 53 excpet that a composition obtained by omitting the first compound (5-decyl-2-[4-(5'-methoxyhexyloxy)phenyl]pyrimidine from the composition of Example 53 was used. The results are shown below.

| 20° C. | 25° C. | 35° C. | 50° C. | 60° C. | 80° C. |
|---|---|---|---|---|---|
| 1100 μsec | 730 μsec | 510 μsec | 230 μsec | 170 μsec | 100 μsec |

| 20° C. | 25° C. | 35° C. | 45° C. |
|---|---|---|---|
| 5400 μsec | 3600 μsec | 2900 μsec | 1800 μsec |

EXAMPLE 53

A ferroelectric liquid crystal device was prepared and the optical response time thereof was measured in the same manner as in Example 51 except that the following composition was used:

EXAMPLE 54

A ferroelectric liquid crystal device was prepared and the optical response time thereof was measured in the same manner as in Example 51 except that the following composition was used:

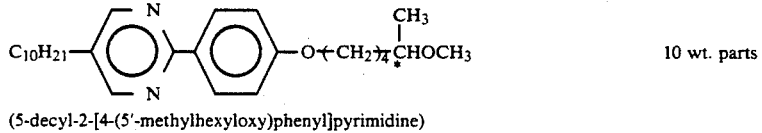 10 wt. parts (5-decyl-2-[4-(5'-methylhexyloxy)phenyl]pyrimidine)

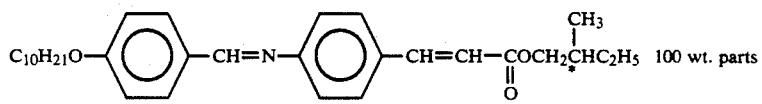 100 wt. parts

The results are as follows.

| 65° C. | 75° C. |
|---|---|
| 115 μsec | 85 μsec |

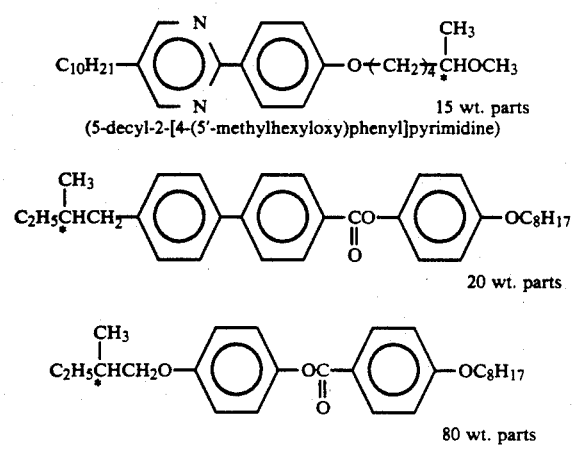

COMPARATIVE EXAMPLE 5

A ferroelectric liquid crystal device was prepared and the optical response time thereof was measured in the same manner as in Example 54 except that a composition obtained by omitting the first compound (5-decyl-2-[4-(5'-methoxyhexyloxy)phenyl]pyrimidine from the composition of Example 54 was used. The results are shown below.

75° C.: 100 μsec

EXAMPLE 55

A ferroelectric liquid crystal device was prepared and the optical response time thereof was measured in the same manner as in Example 51 except that the following composition was used:

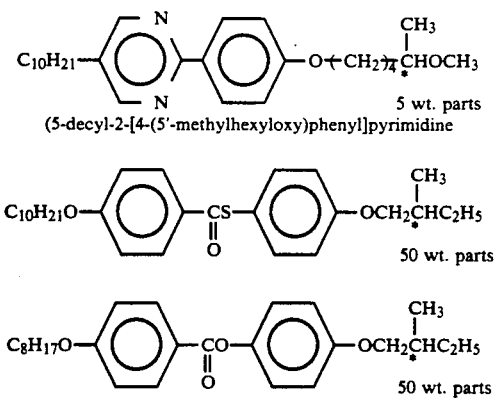

5 wt. parts
(5-decyl-2-[4-(5'-methylhexyloxy)phenyl]pyrimidine 50 wt. parts 50 wt. parts The results are as follows.

| 35° C. | 45° C. | 50° C. |
|---|---|---|
| 1200 μsec | 890 μsec | 760 μsec |

COMPARATIVE EXAMPLE 6

A ferroelectric liquid crystal device was prepared and the optical response time thereof was measured in the same manner as in Example 55 except that a composition obtained by omitting the first compound (5-decyl-2-[4-(5'-methoxyhexyloxy)phenyl]pyrimidine from the composition of Example 55 was used. The results are shown below.

| 35° C. | 45° C. | 50° C. |
|---|---|---|
| 1500 μsec | 1000 μsec | 800 μsec |

EXAMPLE 56

A ferroelectric liquid crystal device was prepared and the optical response time thereof was measured in the same manner as in Example 51 except that the following composition was used:

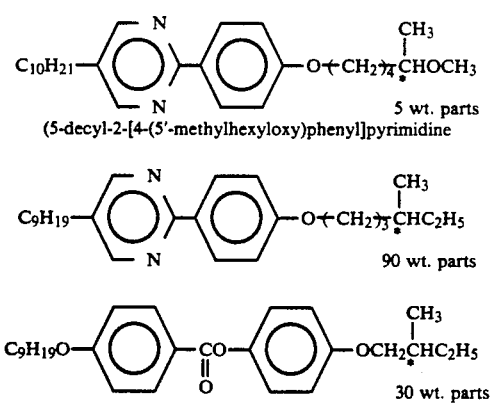

5 wt. parts
(5-decyl-2-[4-(5'-methylhexyloxy)phenyl]pyrimidine 90 wt. parts 30 wt. parts The results are as follows.

| 20° C. | 35° C. |
|---|---|
| 540 μsec | 430 μsec |

COMPARATIVE EXAMPLE 7

A ferroelectric liquid crystal device was prepared and the optical response time thereof was measured in the same manner as in Example 56 except that a composition obtained by omitting the first compound (5-decyl-2-[4-(5'-methoxyhexyloxy)phenyl]pyrimidine from the composition of Example 56 was used. The results are shown below.

| 5° C. | 20° C. | 35° C. |
|---|---|---|
| 900 μsec | 560 μsec | 480 μsec |

EXAMPLE 55

A ferroelectric liquid crystal device was prepared and the optical response time thereof was measured in the same manner as in Example 51 except that a 2%-aqueous solution of polyvinyl alcohol resin (PVA-117, mfd. by Kuraray K.K.) was used instead of the 2% solution of polyimide precursor.

| 20° C. | 30° C. | 40° C. |
|---|---|---|
| 390 μsec | 345 μsec | 295 μsec |

EXAMPLE 56

A ferroelectric liquid crystal device was prepared and the optical response time thereof was measured in the same manner as in Example 51 except that an insulating alignment control layer was formed only by the polyimide resin without using $SiO_2$.

The results are as follows.

| 20° C. | 30° C. | 40° C. |
|---|---|---|
| 370 μsec | 340 μsec | 285 μsec |

EXAMPLES 59-67

Ferroelectric liquid crystal devices were prepared and the optical response times thereof were measured in the same manner as in Example 52 except that 5-decyl-2-[4-(5'-methoxyhexyloxy)phenyl]pyrimidine was replaced by those shown in the following Table 3, respectively.

TABLE 3

| Example | Example compounds of Formula (IV) | wt. parts | 25° C. (μsec) | 35° C. (μsec) | 50° C. (μsec) |
|---|---|---|---|---|---|
| 59 | Ex. 1 | 20 | 680 | 480 | 230 |
| 60 | Ex. 4 | 15 | 700 | 475 | 200 |
| 61 | Ex. 5 | 5 | 710 | 500 | 220 |
| 62 | Ex. 12 | 7 | 670 | 450 | 195 |
| 63 | Ex. 13 | 10 | 630 | 420 | 185 |
| 64 | Ex. 19 | 20 | 650 | 440 | 205 |
| 65 | Ex. 25 | 25 | 580 | 385 | 190 |
| 66 | Ex. 28 | 10 | 680 | 465 | 210 |
| 67 | Ex. 37 | 5 | 710 | 490 | 200 |

What is claimed is:

1. A mesomorphic compound represented by the following formula (III):

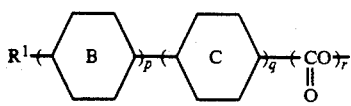

(III)

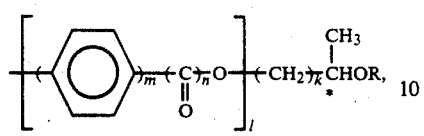

wherein R represents a linear alkyl group having 1-18 carbon atoms, C* represents an asymmetric carbon atom, k is an integer of from 2 to 5, l is 0 or 1, and l is 1, m is 0, 1 or 2 and n is 0 or 1; $R^1$ represents an alkyl or alkoxy group having 1-18 carbon atoms;

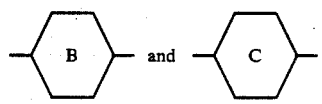

respectively denote

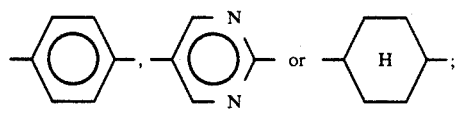

p, q and r are respectively 0 or 1, p and q satisfying the relation of p+q[+r]≧1 with the proviso that (i)

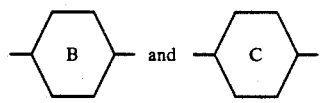

cannot both be

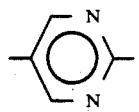

simultaneously; (ii) p+q=2 and r is 1 when l is 0; (iii) m is 1 or 2, n is 0 or 1 and r is 1 when l=1 and p+q=1; (iv) r and n are respectively 0 when l is 1, p+q=2 and m=0; and (v) r and n are respectively 0 or 1 when l is 1, p+q=2 and m is 1.

2. A liquid crystal composition containing at least one mesomorphic compound represented by the following formula (III):

(III)

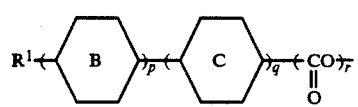

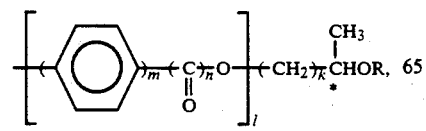

wherein R represents a linear alkyl group having 1-18 carbon atoms, C* represents an asymmetric carbon atom, k is an integer of from 2 to 5, l is 0 or 1, and when l is 1, m is 0, 1 or 2 and n is 0 or 1; $R^1$ represents an alkyl or alkoxy group having 1-18 carbon atoms;

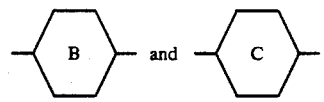

respectively denote

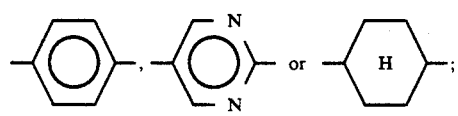

p, q and r are respectively 0 or 1, p and q satisfying the relation of p+q≧1 with the proviso that (i)

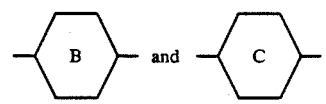

cannot both be

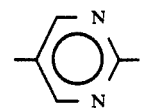

simultaneously (ii) p+q=2 and r is 1 when l is 0; (iii) m is 1 or 2, n is 0 or 1 and r is 1 when l=1 and p+q=1; (iv) r and n are respectively 0 when l is 1, p+q=2 and m=0; and (v) r and n are respectively 0 or 1 when l is 1, p+q=2 and m is 1.

3. A composition according to claim 2, which contains the mesomorphic compound represented by the formula (III) in addition to a ferroelectric liquid crystal.

4. A composition according to claim 3, which contains the mesomorphic compound represented by the formula (III) in a proportion of 0.1-99 wt. %.

5. A composition according to claim 3, which contains the mesomorphic compound represented by the formula (III) in a proportion of 1-90 wt. %.

6. A composition according to claim 2, which contains the mesomorphic compound represented by the formula (III) in addition to a non-chiral smectic liquid crystal.

7. A composition according to claim 6, which contains the mesomorphic compound represented by the formula (III) in a proportion of 0.1-99 wt. %.

8. A composition according to claim 2, which contains the mesomorphic compound represented by the formula (III) in addition to a nematic liquid crystal.

9. A composition according to claim 6, which contains the mesomorphic compound represented by the formula (III) in a proportion of 0.01-50 wt. %.

10. A liquid crystal device comprising: a pair of substrates and a liquid crystal composition disposed therebetween containing at least one compound represented by the following formula (III):

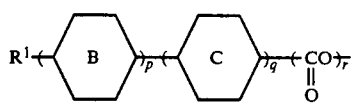
(III)

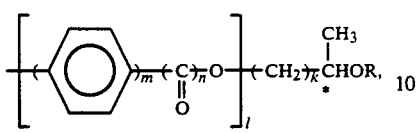

wherein R represents a linear alkyl group having 1-18 carbon atoms, C* represents an asymmetric carbon atom, k is an integer of from 2 to 5 l is 0 or 1, and when l is 1, m is 0, 1 or 2 and n is 0 or 1; $R^1$ represents an alkyl or alkoxy group having 1-18 carbon atoms;

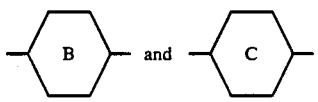

respectively denote

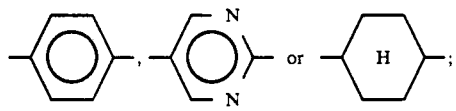

p, q and r are respectively 0 or 1, p and q satisfying the relation of $p+q \geq 1$ with the proviso that (i)

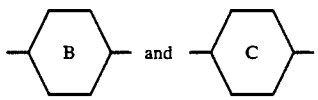

cannot both be

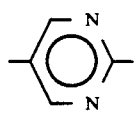

simultaneously; (ii) $p+q=2$ and r is 1 when l is 0; (iii) m is 1 or 2, n is 0 or 1 and r is 1 when $l=1$ and $p+q=1$; (iv) r and n are respectively 0 when l is 1, $p+q=2$ and $m=0$; and (v) r and n are respectively 0 or 1 when l is 1, $p+q=2$ and m is 1.

11. A compound according to claim 1, which is in a liquid crystal state.

12. A compound according to claim 11, which is in a smectic phase.

13. A compound according to claim 12, which is in a chiral smectic phase.

14. A compound according to claim 1, which is

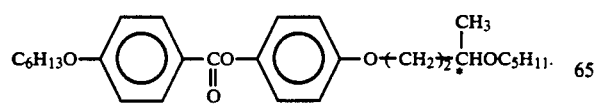

15. A compound according to claim 1, which is

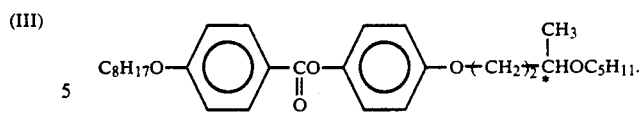

16. A compound according to claim 1, which is

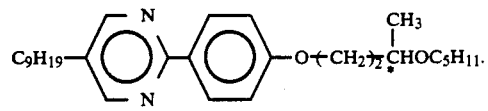

17. A compound according to claim 1, which is

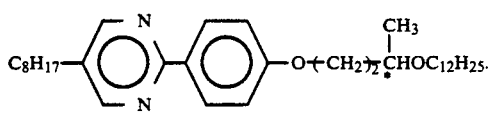

18. A compound according to claim 1, which is

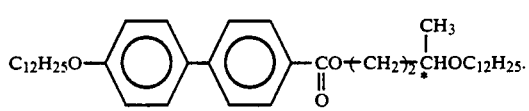

19. A compound according to claim 1, which is

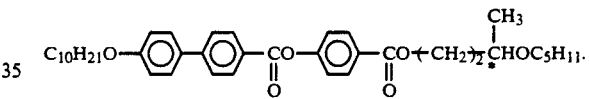

20. A compound according to claim 1, which is

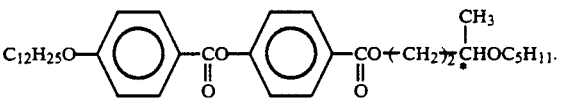

21. A compound according to claim 1, which is

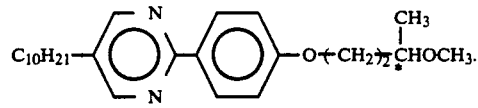

22. A compound according to claim 1, which is

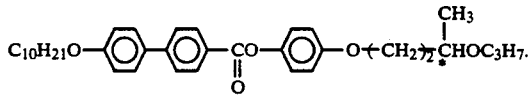

23. A compound according to claim 1, which is

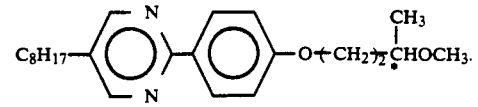

24. A compound according to claim 1, which is

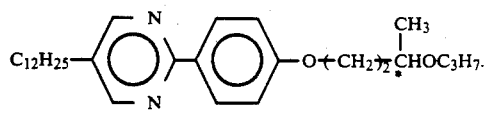

25. A compound according to claim 1, which is

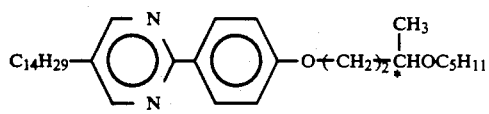

26. A compound according to claim 1, which is

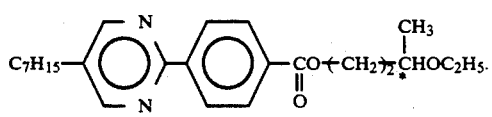

27. A compound according to claim 1, which is

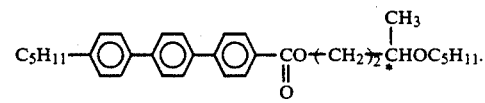

28. A compound according to claim 1, which is

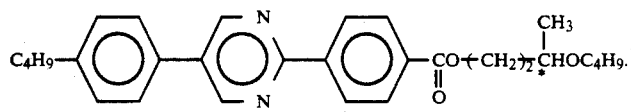

29. A compound according to claim 1, which is

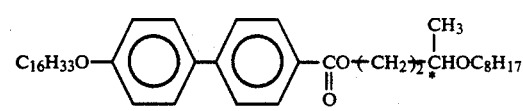

30. A compound according to claim 1, which is

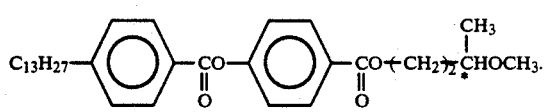

31. A compound according to claim 1, which is

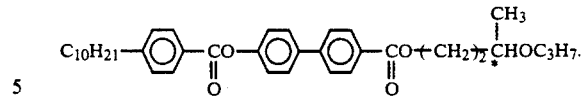

32. A compound according to claim 1, which is

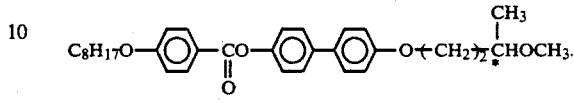

33. A compound according to claim 1, which is

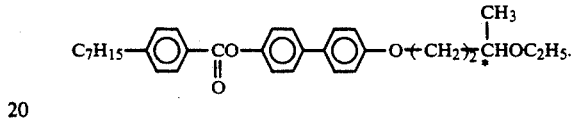

34. A compound according to claim 1, which is

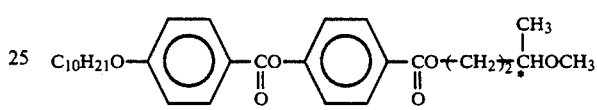

35. A compound according to claim 1, which is

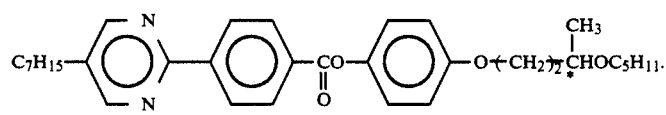

36. A compound according to claim 1, which is

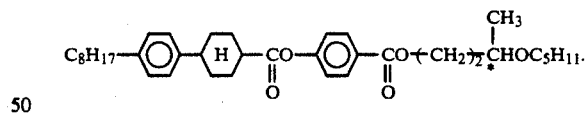

37. A compound according to claim 1, which is

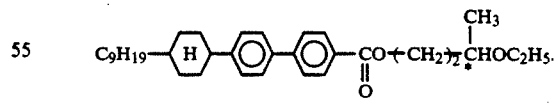

38. A compound according to claim 1, which is

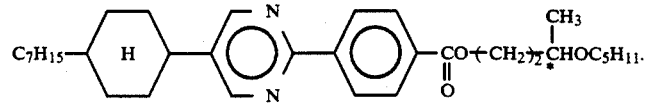

39. A compound according to claim 1, which is

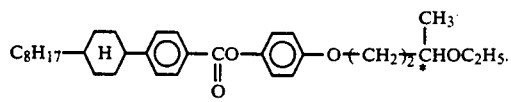

40. A compound according to claim 1, which is

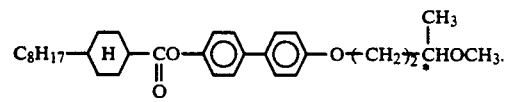

41. A compound according to claim 1, which is

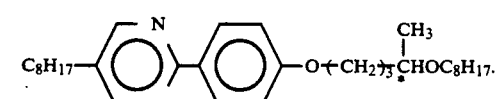

42. A compound according to claim 1, which is

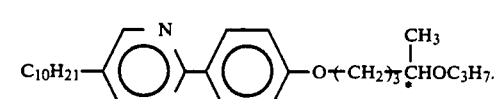

43. A compound according to claim 1, which is

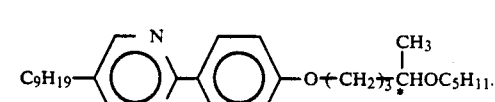

44. A compound according to claim 1, which is

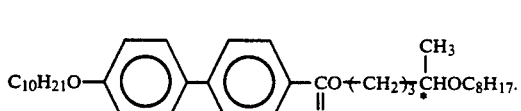

45. A compound according to claim 1, which is

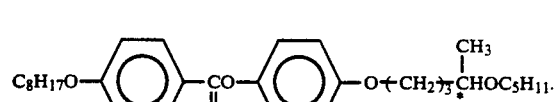

46. A compound according to claim 1, which is

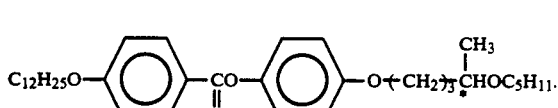

47. A compound according to claim 1, which is

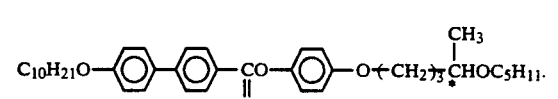

48. A compound according to claim 1, which is

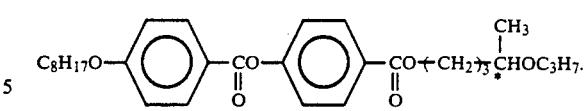

49. A compound according to claim 1, which is

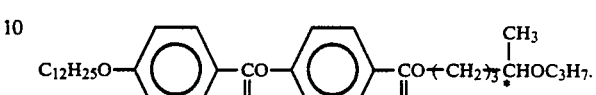

50. A compound according to claim 1, which is

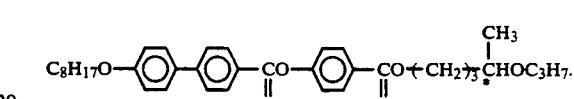

51. A compound according to claim 1, which is

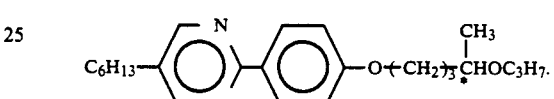

52. A compound according to claim 1, which is

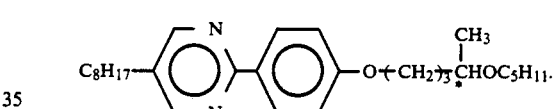

53. A compound according to claim 1, which is

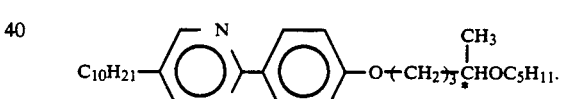

54. A compound according to claim 1, which is

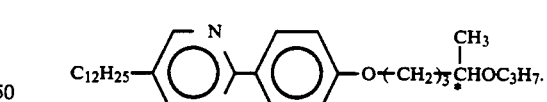

55. A compound according to claim 1, which is

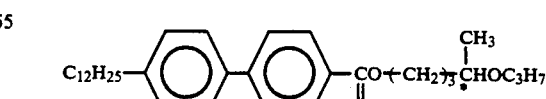

56. A compound according to claim 1, which is

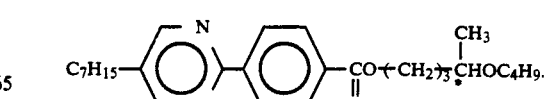

57. A compound according to claim 1, which is

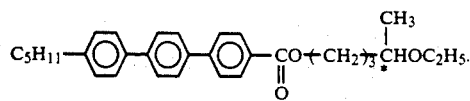

58. A compound according to claim 1, which is

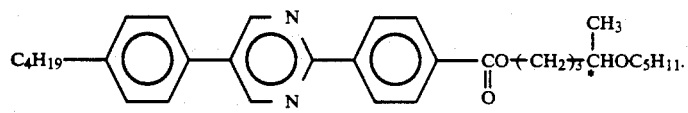

59. A compound according to claim 1, which is

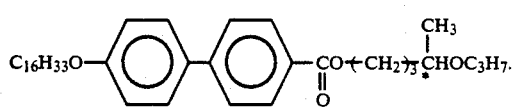

60. A compound according to claim 1, which is

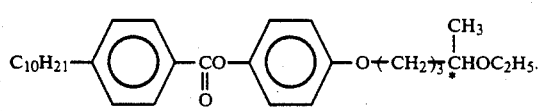

61. A compound according to claim 1, which is

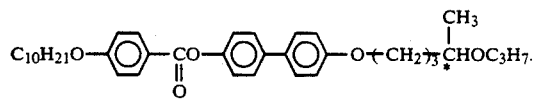

62. A compound according to claim 1, which is

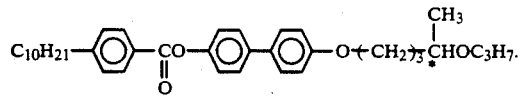

63. A compound according to claim 1, which is

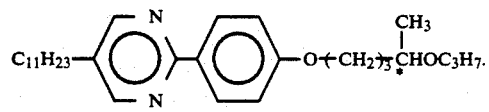

64. A compound according to claim 1, which is

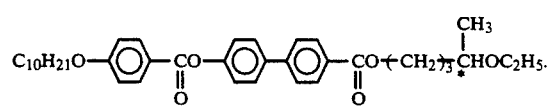

65. A compound according to claim 1, which is

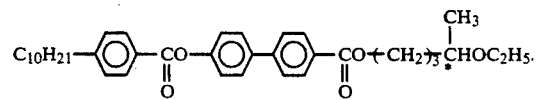

66. A compound according to claim 1, which is

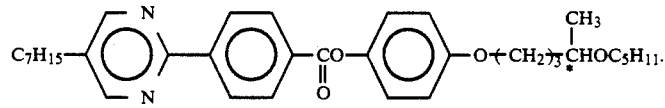

67. A compound according to claim 1, which is

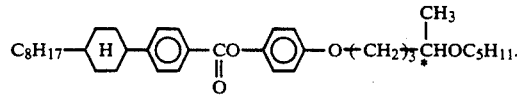

68. A compound according to claim 1, which is

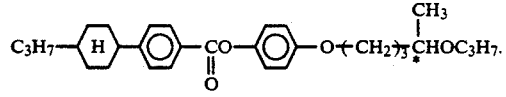

69. A compound according to claim 1, which is

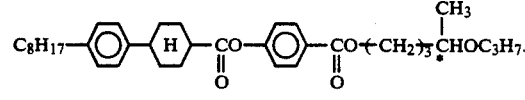

70. A compound according to claim 1, which is

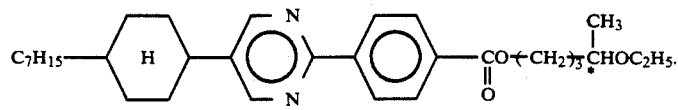

71. A compound according to claim 1, which is

72. A compound according to claim 1, which is

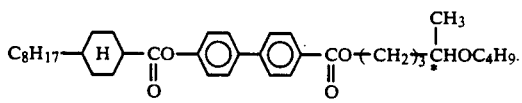

73. A compound according to claim 1, which is

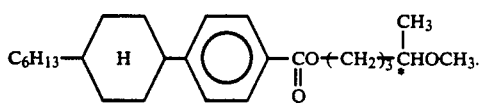

74. A compound according to claim 1, which is

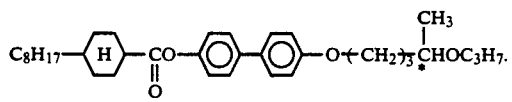

75. A compound according to claim 1, which is

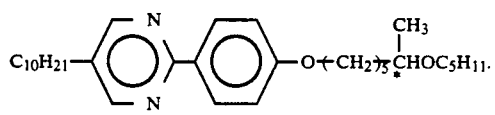

76. A compound according to claim 1, which is

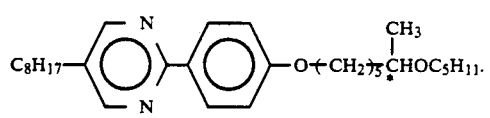

77. A compound according to claim 1, which is

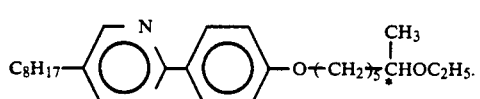

78. A compound according to claim 1, which is

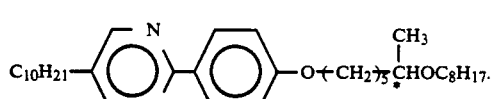

79. A compound according to claim 1, which is

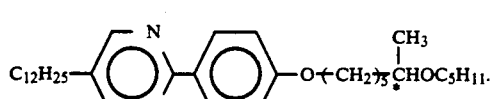

80. A compound according to claim 1, which is

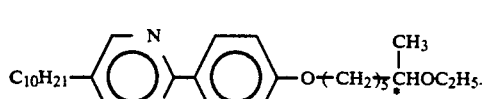

81. A compound according to claim 1, which is

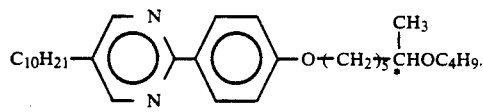

82. A compound according to claim 1, which is

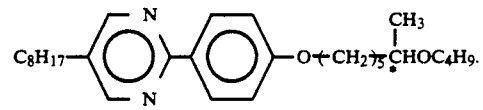

83. A compound according to claim 1, which is

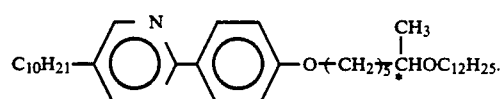

84. A compound according to claim 1, which is

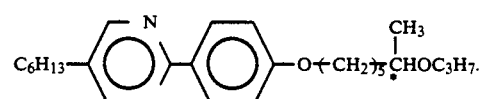

85. A compound according to claim 1, which is

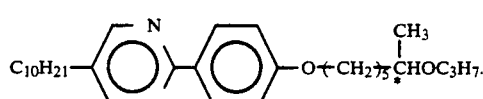

86. A compound according to claim 1, which is

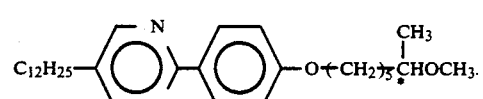

87. A compound according to claim 1, which is

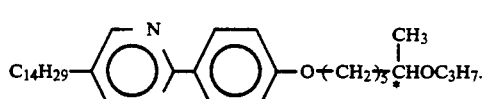

88. A compound according to claim 1, which is

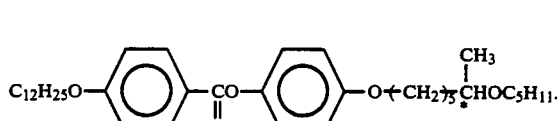

89. A compound according to claim 1, which is

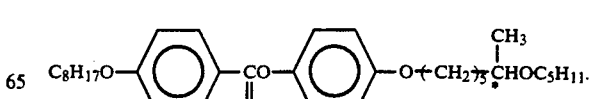

90. A compound according to claim 1, which is

91. A compound according to claim 1, which is

C₈H₁₇O—⟨benzene⟩—C(O)O—⟨benzene⟩—O(CH₂)₅*CH(CH₃)OC₂H₅.

92. A compound according to claim 1, which is

C₈H₁₇O—⟨benzene⟩—C(O)O—⟨benzene⟩—O(CH₂)₅*CH(CH₃)OC₄H₉.

93. A compound according to claim 1, which is

C₈H₁₇O—⟨benzene⟩—C(O)O—⟨benzene⟩—O(CH₂)₅*CH(CH₃)OC₈H₁₇.

94. A compound according to claim 1, which is

C₁₀H₂₁O—⟨benzene⟩—C(O)O—⟨benzene⟩—O(CH₂)₅*CH(CH₃)OC₅H₁₁.

95. A compound according to claim 1, which is

C₁₀H₂₁O—⟨benzene⟩—C(O)O—⟨benzene⟩—O(CH₂)₅*CH(CH₃)OC₂H₅.

96. A compound according to claim 1, which is

C₁₀H₂₁O—⟨benzene⟩—C(O)O—⟨benzene⟩—O(CH₂)₅*CH(CH₃)OC₈H₁₇.

97. A compound according to claim 1, which is

C₁₂H₂₅O—⟨benzene⟩—C(O)O—⟨benzene⟩—O(CH₂)₅*CH(CH₃)OC₈H₁₇.

98. A compound according to claim 1, which is

C₁₂H₂₅O—⟨benzene⟩—C(O)O—⟨benzene⟩—O(CH₂)₅*CH(CH₃)OC₂H₅.

99. A compound according to claim 1, which is

C₇H₁₅—⟨benzene⟩—C(O)O—⟨benzene⟩—O(CH₂)₅*CH(CH₃)OC₃H₇.

100. A compound according to claim 1, which is

C₁₄H₂₉O—⟨benzene⟩—C(O)O—⟨benzene⟩—O(CH₂)₅*CH(CH₃)OC₄H₉.

101. A compound according to claim 1, which is

C₁₂H₂₅O—⟨benzene⟩—C(O)O—⟨benzene⟩—C(O)O(CH₂)₅*CH(CH₃)OC₅H₁₁.

102. A compound according to claim 1, which is

C₈H₁₇O—⟨benzene⟩—C(O)O—⟨benzene⟩—C(O)O(CH₂)₅*CH(CH₃)OC₅H₁₁.

103. A compound according to claim 1, which is

C₈H₁₇O—⟨benzene⟩—C(O)O—⟨benzene⟩—C(O)O(CH₂)₅*CH(CH₃)OC₂H₅.

104. A compound according to claim 1, which is

C₈H₁₇O—⟨benzene⟩—C(O)O—⟨benzene⟩—C(O)O(CH₂)₅*CH(CH₃)OC₈H₁₇.

105. A compound according to claim 1, which is

C₁₀H₂₁O—⟨benzene⟩—C(O)O—⟨benzene⟩—C(O)O(CH₂)₅*CH(CH₃)OC₅H₁₁.

106. A compound according to claim 1, which is

C₁₀H₂₁O—⟨benzene⟩—C(O)O—⟨benzene⟩—C(O)O(CH₂)₅*CH(CH₃)OC₂H₅.

107. A compound according to claim 1, which is

C₁₀H₂₁O—⟨benzene⟩—C(O)O—⟨benzene⟩—C(O)O(CH₂)₅*CH(CH₃)OC₈H₁₇.

108. A compound according to claim 1, which is

C₁₂H₂₅O—⟨benzene⟩—C(O)O—⟨benzene⟩—C(O)O(CH₂)₅*CH(CH₃)OC₂H₅.

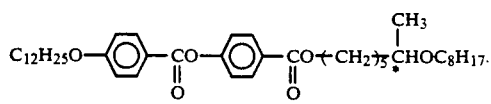

109. A compound according to claim 1, which is

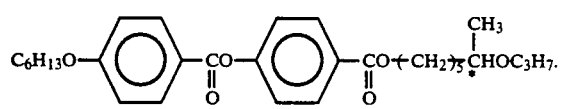

110. A compound according to claim 1, which is

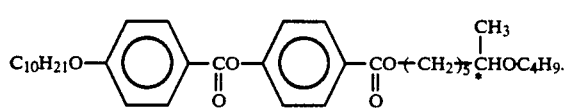

111. A compound according to claim 1, which is

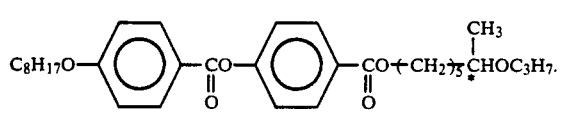

112. A compound according to claim 1, which is

113. A compound according to claim 1, which is

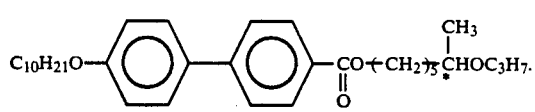

114. A compound according to claim 1, which is

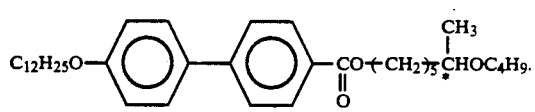

115. A compound according to claim 1, which is

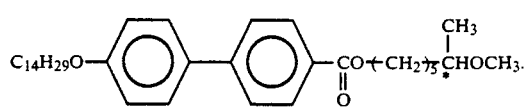

116. A compound according to claim 1, which is

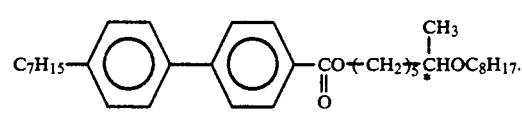

117. A compound according to claim 1, which is

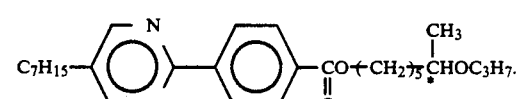

118. A compound according to claim 1, which is

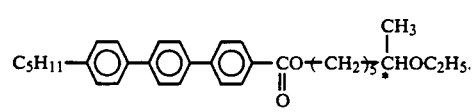

119. A compound according to claim 1, which is

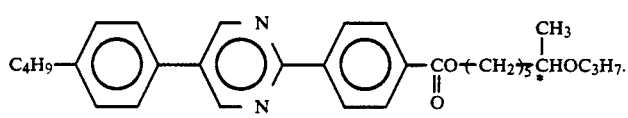

120. A compound according to claim 1, which is

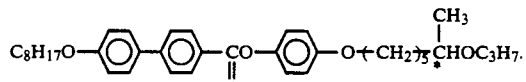

121. A compound according to claim 1, which is

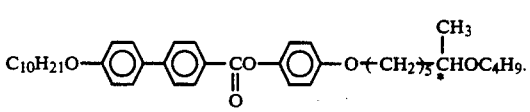

122. A compound according to claim 1, which is

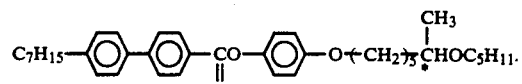

123. A compound according to claim 1, which is

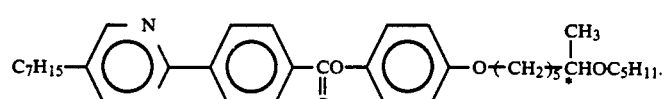

124. A compound according to claim 1, which is

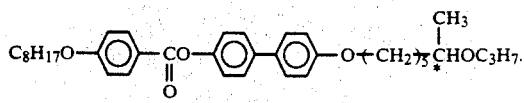

125. A compound according to claim 1, which is

126. A compound according to claim 1, which is

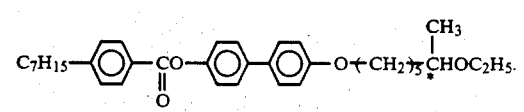

127. A compound according to claim 1, which is

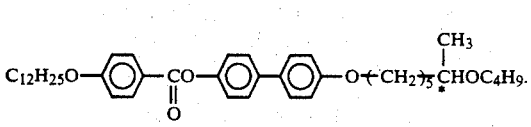

128. A compound according to claim 1, which is

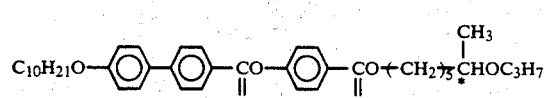

129. A compound according to claim 1, which is

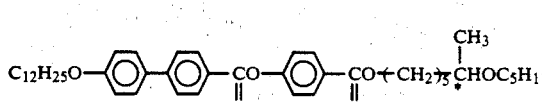

130. A compound according to claim 1, which is

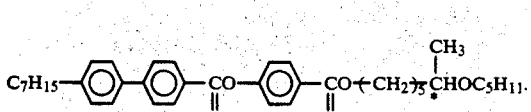

131. A compound according to claim 1, which is

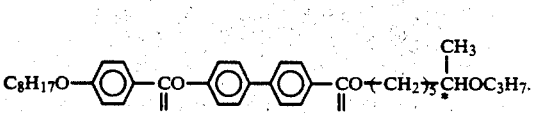

132. A compound according to claim 1, which is

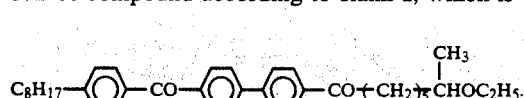

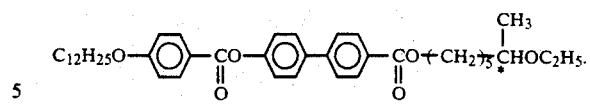

133. A compound according to claim 1, which is

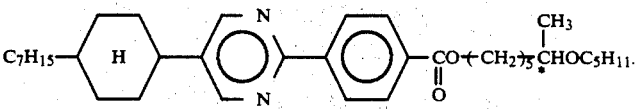

134. A compound according to claim 1, which is

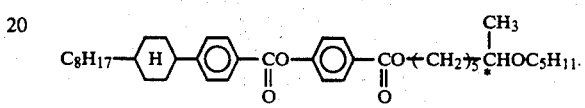

135. A compound according to claim 1, which is

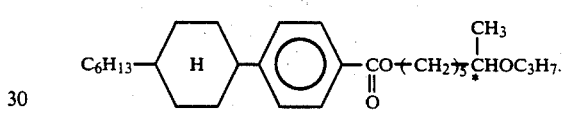

136. A compound according to claim 1, which is

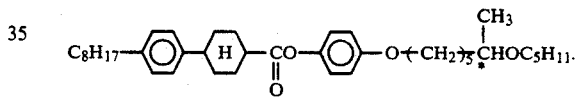

137. A compound according to claim 1, which is

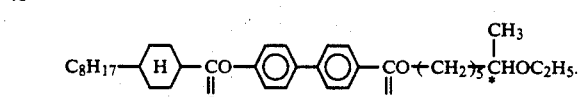

138. A compound according to claim 1, which is

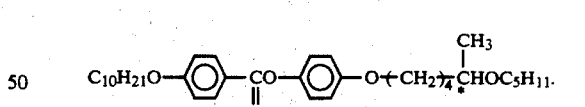

139. A compound according to claim 1, which is

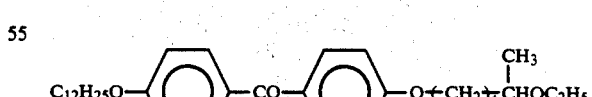

140. A compound according to claim 1, which is

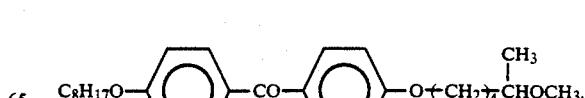

141. A compound according to claim 1, which is

142. A compound according to claim 1, which is

C₁₃H₂₇—⟨C₆H₄⟩—CO-O—⟨C₆H₄⟩—O-(CH₂)₄-*CH(CH₃)-OC₂H₅.

143. A compound according to claim 1, which is

C₁₀H₂₁O—⟨C₆H₄⟩—⟨C₆H₄⟩—CO-O—⟨C₆H₄⟩—O-(CH₂)₄-*CH(CH₃)-OC₄H₉.

144. A compound according to claim 1, which is

C₁₀H₂₁O—⟨C₆H₄⟩—CO-O—⟨C₆H₄⟩—⟨C₆H₄⟩—O-(CH₂)₄-*CH(CH₃)-OC₃H₇.

145. A compound according to claim 1, which is

C₇H₁₅—⟨C₆H₄⟩—CO-O—⟨C₆H₄⟩—⟨C₆H₄⟩—O-(CH₂)₄-*CH(CH₃)-OC₃H₇.

146. A compound according to claim 1, which is

C₇H₁₅—⟨pyrimidine⟩—⟨C₆H₄⟩—CO-O—⟨C₆H₄⟩—O-(CH₂)₄-*CH(CH₃)-OC₈H₁₇.

147. A compound according to claim 1, which is

C₈H₁₇O—⟨C₆H₄⟩—CO-O—⟨C₆H₄⟩—CO-O-(CH₂)₄-*CH(CH₃)-OC₂H₅.

148. A compound according to claim 1, which is

C₁₂H₂₅O—⟨C₆H₄⟩—CO-O—⟨C₆H₄⟩—CO-O-(CH₂)₄-*CH(CH₃)-OCH₃.

149. A compound according to claim 1, which is

C₁₀H₂₁O—⟨C₆H₄⟩—⟨C₆H₄⟩—CO-O—⟨C₆H₄⟩—CO-O-(CH₂)₄-*CH(CH₃)-OC₂H₅.

150. A compound according to claim 1, which is

C₁₃H₁₇—⟨C₆H₄⟩—CO-O—⟨C₆H₄⟩—CO-O-(CH₂)₄-*CH(CH₃)-OC₅H₁₁.

151. A compound according to claim 1, which is

C₁₀H₂₁O—⟨C₆H₄⟩—⟨C₆H₄⟩—CO-O-(CH₂)₄-*CH(CH₃)-OC₃H₇.

152. A compound according to claim 1, which is

C₁₄H₂₉O—⟨C₆H₄⟩—⟨C₆H₄⟩—CO-O-(CH₂)₄-*CH(CH₃)-OC₃H₇.

153. A compound according to claim 1, which is

C₇H₁₅—⟨C₆H₄⟩—⟨C₆H₄⟩—CO-O-(CH₂)₄-*CH(CH₃)-OC₅H₁₁.

154. A compound according to claim 1, which is

C₁₂H₂₅—⟨C₆H₄⟩—⟨C₆H₄⟩—CO-O-(CH₂)₄-*CH(CH₃)-OC₄H₉.

155. A compound according to claim 1, which is

C₇H₁₅—⟨pyrimidine⟩—⟨C₆H₄⟩—CO-O-(CH₂)₄-*CH(CH₃)-OC₃H₇.

156. A compound according to claim 1, which is

C₈H₁₇—⟨pyrimidine⟩—⟨C₆H₄⟩—O-(CH₂)₄-*CH(CH₃)-OC₃H₇.

157. A compound according to claim 1, which is

C₉H₁₉—⟨pyrimidine⟩—⟨C₆H₄⟩—O-(CH₂)₄-*CH(CH₃)-OCH₃.

158. A compound according to claim 1, which is

C₁₀H₂₁—⟨pyrimidine⟩—⟨C₆H₄⟩—O-(CH₂)₄-*CH(CH₃)-OC₃H₇.

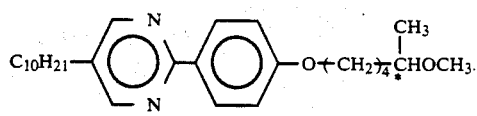
159. A compound according to claim 1, which is
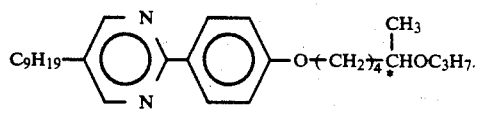
160. A compound according to claim 1, which is
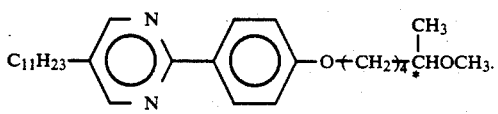
161. A compound according to claim 1, which is
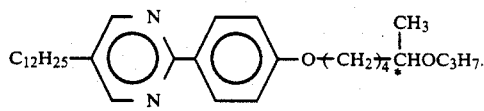
162. A compound according to claim 1, which is
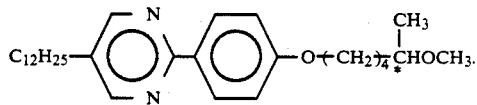
163. A compound according to claim 1, which is
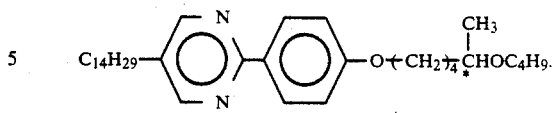
164. A compound according to claim 1, which is
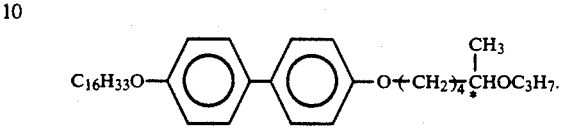
165. A compound according to claim 1, which is
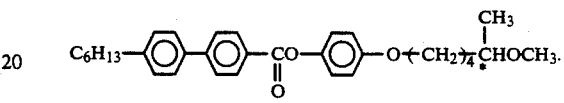
166. A compound according to claim 1, which is
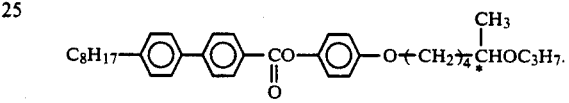
167. A compound according to claim 1, which is
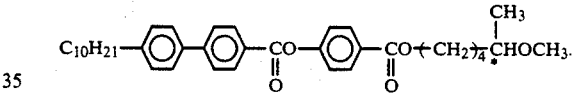
* * * * *

UNITED STATES PATENT AND TRADEMARK OFFICE
CERTIFICATE OF CORRECTION

PATENT NO. : 5,143,643
DATED : September 1, 1992
INVENTOR(S) : TAKASHI IWAKI, ET AL.

It is certified that error appears in the above-identified patent and that said Letters Patent is hereby corrected as shown below:

COLUMN 15

Line 5, "are the description" should be deleted.

COLUMN 39

Example 39, "$CHOC_3$" should read --$CHOC_3H_7$--.

COLUMN 81

Line 15, "and" should read --and when--.

Signed and Sealed this

Twenty-first Day of December, 1993

Attest:

BRUCE LEHMAN

Attesting Officer        Commissioner of Patents and Trademarks